(12) United States Patent
Wong et al.

(10) Patent No.: US 11,954,614 B2
(45) Date of Patent: *Apr. 9, 2024

(54) SYSTEMS AND METHODS FOR VISUALIZING A PATTERN IN A DATASET

(71) Applicant: 10X Genomics, Inc., Pleasanton, CA (US)

(72) Inventors: Alexander Y. Wong, San Francisco, CA (US); Jeffrey Mellen, Martinez, CA (US); Kevin J. Wu, San Francisco, CA (US); Paul Ryvkin, San Jose, CA (US); Preyas Shah, Pleasanton, CA (US); Patrick Marks, San Francisco, CA (US); Niranjan Srinivas, Dublin, CA (US)

(73) Assignee: 10X GENOMICS, INC., Pleasanton, CA (US)

(*) Notice: Subject to any disclaimer, the term of this patent is extended or adjusted under 35 U.S.C. 154(b) by 1331 days.

This patent is subject to a terminal disclaimer.

(21) Appl. No.: 16/442,800

(22) Filed: Jun. 17, 2019

(65) Prior Publication Data

US 2019/0332963 A1 Oct. 31, 2019

Related U.S. Application Data

(63) Continuation-in-part of application No. 15/891,607, filed on Feb. 8, 2018, now Pat. No. 10,347,365.
(Continued)

(51) Int. Cl.
*G06N 7/01* (2023.01)
*G06F 16/28* (2019.01)
(Continued)

(52) U.S. Cl.
CPC ............. *G06N 7/01* (2023.01); *G06F 16/285* (2019.01); *G06F 16/904* (2019.01); *G16B 25/10* (2019.02);
(Continued)

(58) Field of Classification Search
None
See application file for complete search history.

(56) References Cited

U.S. PATENT DOCUMENTS

| 2015/0376609 A1 | 12/2015 | Hindson et al. |
| 2018/0225416 A1 | 8/2018 | Wong et al. |
| 2018/0340169 A1 | 11/2018 | Belhocine et al. |

OTHER PUBLICATIONS

Packer et al. Single-Cell Multi-omics: An Engine for New Quantitative Models of Gene Regulation. Trends in Genetics Sep. 2018, vol. 34, No. 9, pp. 653-665 (Year: 2018).*
(Continued)

*Primary Examiner* — Olivia M. Wise
(74) *Attorney, Agent, or Firm* — MORGAN, LEWIS & BOCKIUS LLP

(57) ABSTRACT

A visualization system comprising a persistent memory, storing a dataset, and a non-persistent memory implements a pattern visualizing method. The dataset contains discrete attribute values for each first entity of a first type in a plurality of first entities of the first type and discrete attribute values for each first entity of a second type in a plurality of first entities of the second type for each second entity in a plurality of second entities. The dataset is compressed by blocked compression and represents discrete attribute values in both compressed sparse row and column formats. The discrete attribute values are clustered to assign each second entity to a cluster in a plurality of clusters.

22 Claims, 44 Drawing Sheets

Specification includes a Sequence Listing.

Related U.S. Application Data

(60) Provisional application No. 62/745,189, filed on Oct. 12, 2018, provisional application No. 62/572,544, filed on Oct. 15, 2017, provisional application No. 62/456,547, filed on Feb. 8, 2017.

(51) Int. Cl.
    *G06F 16/904*      (2019.01)
    *G16B 25/10*      (2019.01)
    *G16B 40/00*      (2019.01)
    *G16B 45/00*      (2019.01)
    *G16B 50/30*      (2019.01)

(52) U.S. Cl.
    CPC ............. *G16B 40/00* (2019.02); *G16B 45/00* (2019.02); *G16B 50/30* (2019.02)

(56) References Cited

OTHER PUBLICATIONS

Zhao et al. Dr.seq2: A quality control and analysis pipeline for parallel single cell transcriptome and epigenome data. Plos One 2017, 12(7): e0180583, pp. 1-14 (Year: 2017).*

Anders et al., "Differential expression analysis for sequence count data," Genome Biology, Nov. 10, 2010, 12 pgs.

Blondel et al., "Fast unfolding of communities in large networks," J. Stat. Mech., Jul. 25, 2008, 12 pgs.

Bluthmann et al., "T-cell-specific deletion of T-cell receptor transgenes allows functional rearrangement of endogenous α- and β-genes", Nature 334, 156-159 (1988).

Buenrostro et al., "ATAC-seq: A Method for Assaying Chromatin Accessibility Genome-Wide", Curr. Protoc. Mol. Biol. 109:21.29. 1-21.29.9.

Chen et al., "Clustering-based identification of clonally-related immunoglobulin gene sequence sets," Immunology Research, Sep. 27, 2010, 6(Suppl 1): S4. 7 pgs.

Duda et al., "Pattern Classification," 2010, pp. 115-116.

Ganusov et al., "Do most lymphocytes in humans really reside in the gut?" Trends in Immunology, vol. 28, Issue 12, p. 514-518, Dec. 1, 2007.

Goharian et al., "Comparative analysis of sparse matrix algorithms for information retrieval", Computer 2, 0.4, 2003.

Hastie et al., "The Elements of Statistical Learning", Springer, New York, pp. 55-57; 59-66; 59-64; ; 64-65, 69-72; 330-331.

Hershberg et al., "The analysis of clonal expansions in normal and autoimmune B cell repertoires," Philosophical Transactions B, Sep. 5, 2015, 16 pgs.

Li et al., "Utilization of Ig heavy chain variable, diversity, and joining gene segments in children with B-lineage acute lymphoblastic leukemia: implications for the mechanisms of VDJ recombination and for pathogenesis," Blood, Jun. 15, 2004, vol. 103, No. 12, pp. 4602-4609.

Li, "Tabix: fast retrieval of sequence features from generic TAB-delimited files", Bioinformatics. Mar. 1, 2011;27(5):718-9.

Matsuda et al., "The Complete Nucleotide Sequence of the Humabe Immunoglobulin Heavy Chain Variable Region Locus," J. Exp. Med., Dec. 7, 1998, vol. 188, No. 11, pp. 2151-2162.

Mostovoy et al., "A hybrid approach for de novo human genome sequence assembly and phasing", Nat Methods. Jul. 2016;13(7):587-90.

Narasimhan et al., "Health and population effects of rare gene knockouts in adult humans with related parents," Science 352, Apr. 22, 2016, 11 pgs.

Rudolph et al., "How TCRs Bind MHCs, Peptides, and Coreceptors", Annu Rev Immunol 24: pp. 419-466.

Uematsu et al., "In transgenic mice the introduced functional T cell receptor beta gene prevents expression of endogenous beta genes", Cell, Mar. 25, 1988;52(6):831-41.

Usoskin et al., "Unbiased classification of sensory neuron types by large-scale single-cell RNA Sequencing", Nature Neuroscience, vol. 18, No. 1, Jan. 2015.

Van der Maaten et al., "Visualizing Data using t-SNE," Journal of Machine Learning Research 9, Nov. 2008, pp. 2579-2605.

Vijayakumar et al., "Locally Weighted Projection Regression: An O(n) Algorithm for Incremental Real Time Learning in High Dimensional Space", Proc. of Seventeenth International Conference on Machine Learning (ICML2000) , pp. 1079-1086 (2000).

Yaari et al., "Practical guidelines for B-cell receptor repertoire sequencing analysis," Genomics Medicine, 2015, 7:121, 12 pgs.

Yassai et al., "A clonotype nomenclature for T cell receptors", Immunogenetics (2009) 61, pp. 493-502.

Yu et al., "Shrinkage estimation of dispersion in Negative Binomial models for RNA-seq experiments with small sample size," Bioinformatics, Apr. 14, 2013, vol. 29 No. 10 2013, pp. 1275-1282.

Zheng et al., "Halotyping germline and cancer genomes using high-throughput linked-read sequencing," Nat Biotechnol., Mar. 2016, 34(3): 303-311, 28 pgs.

"Chromium™ Single Cell 3' Reagent Kits v2 User Guide," 10X Genomics, 2017.

Multiplexed Sequencing with the Illumina Genome Analyzer System, Illumina Sequencing, 2008.

U.S. Appl. No. 62/508,947, filed May 19, 2017.

U.S. Appl. No. 62/629,602, filed Feb. 12, 2018.

* cited by examiner

SEQUENCE LISTING

<160> NUMBER OF SEQ ID NOS: 3

<210> SEQ ID NO 1
<211> LENGTH: 21
<212> TYPE: DNA
<213> ORGANISM: Artificial Sequence
<220> FEATURE:
<223> OTHER INFORMATION: Hypothetical sequence
<220> FEATURE:
<221> NAME/KEY: misc_feature
<222> LOCATION: (1)..(10)
<223> OTHER INFORMATION: n is a, c, g, or t
<220> FEATURE:
<221> NAME/KEY: misc_feature
<222> LOCATION: (13)..(21)
<223> OTHER INFORMATION: n is a, c, g, or t

<400> SEQUENCE: 1
nnnnnnnnnn bcnnnnnnnn n                                              21

<210> SEQ ID NO 2
<211> LENGTH: 15
<212> TYPE: DNA
<213> ORGANISM: Artificial Sequence
<220> FEATURE:
<223> OTHER INFORMATION: Hypothetical sequence

<400> SEQUENCE: 2
ctcattgtaa ctcct                                                     15

<210> SEQ ID NO 3
<211> LENGTH: 15

-continued

```
<212> TYPE: DNA
<213> ORGANISM: Artificial Sequence
<220> FEATURE:
<223> OTHER INFORMATION: Hypothetical sequence

<400> SEQUENCE: 3
gccggacgac attaa                                                    15
```

SYSTEMS AND METHODS FOR VISUALIZING A PATTERN IN A DATASET

CROSS REFERENCE TO RELATED APPLICATIONS

This application claims priority to U.S. patent application Ser. No. 15/891,607 entitled "Systems and Methods for Visualizing a Pattern in a Dataset," filed Feb. 8, 2018, which, in turn, claims priority to United States Provisional Patent Applications Nos. 62/572,544, entitled "Systems and Methods for Visualizing a Pattern in a Dataset," filed Oct. 2017 and 62/456,547, entitled "Systems and Methods for Visualizing a Pattern in a Dataset," filed Feb. 8, 2017 each of which is hereby incorporated by reference in its entirety. This application also claims priority to U.S. Provisional Patent Application No. 62/745,189, entitled "Systems and Methods for Visualizing a Pattern in a Dataset," filed Oct. 12, 2018, which is hereby incorporated by reference in its entirety.

SEQUENCE LISTING

The instant application contains a Sequence Listing which has been submitted electronically in ASCII format and is hereby incorporated by reference in its entirety. Said ASCII copy, created on Jul. 16, 2019, is named 104371-5019-US01_ST25.txt and is 2 kilobytes in size.

TECHNICAL FIELD

This specification describes technologies relating to visualizing patterns in datasets.

BACKGROUND

The discovery of patterns in a dataset facilitates a number of technical applications such as the discovery of changes in discrete attribute values in first entities between different classes (e.g., diseased state, non-diseased state, disease stage, etc.). For instance, in the biological arts, advances in RNA-extraction protocols and associated methodologies has led to the ability to perform whole transcriptome shotgun sequencing that quantifies gene expression in biological samples in counts of transcript reads mapped to genes. This has given rise to high throughput transcript identification and the quantification of gene expression for hundreds or even thousands of individual cells in a single dataset. Thus, in the art, datasets containing discrete attribute values (e.g., count of transcript reads mapped to individual genes in a particular cell) for each first entity in a plurality of first entities for each respective second entity in a plurality of second entities have been generated. While this is a significant advancement in the art, a number of technical problems need to be addressed to make such data more useful.

One drawback with such advances in the art is that the datasets tend to be large and thus are not easily loaded in their entirety into non-persistent memory (e.g., random access memory) of conventional computers used by workers in the field when visualizing the data. And, even if such datasets were loaded into non-persistent memory, the processing time needed to discern patterns in such datasets is unsatisfactory. Another drawback is that experiments are not performed in a high replicate manner, thereby impairing the ability to use simplistic statistical methods to account for experimental design and to therefore appropriately account for stochastic variation in the data (e.g., stochastic variation in the counts of transcript reads mapped to genes arising from the experimental design). Moreover, yet another drawback with such advances in the art are the unsatisfactory way in which conventional methods find patterns in such datasets. For instance, such patterns may relate to the discovery of unknown classes among the members of the dataset. For example, the discovery that a dataset of what was thought to be homogenous cells turns out to include cells of two different classes. Such patterns may also relate to the discovery of variables that are statistically associated with known classes. For instance, the discovery that the transcript abundance of a subset of mRNA mapping to a core set of genes discriminates between cells that are in a diseased state versus cells that are not in a diseased state. The discovery of such patterns (e.g., the discovery of genes whose mRNA expression discriminates classes or that define classes) in datasets that are very large, are not amendable to classical statistics because of limited replicate information, and for which such patterns in many instances relate to biological processes that are not well understood remains a technical challenge for which improved tools are needed in the art in order to adequately address such drawbacks.

SUMMARY

Technical solutions (e.g., computing systems, methods, and non-transitory computer readable storage mediums) for addressing the above identified problems with discovery patterns in datasets are provided in the present disclosure.

The following presents a summary of the invention in order to provide a basic understanding of some of the aspects of the invention. This summary is not an extensive overview of the invention. It is not intended to identify key/critical elements of the invention or to delineate the scope of the invention. Its sole purpose is to present some of the concepts of the invention in a simplified form as a prelude to the more detailed description that is presented later.

One aspect of the present disclosure provides a visualization system. The visualization system comprises one or more processing cores, a persistent memory and a non-persistent memory. The persistent memory and the non-persistent memory collectively store instructions for performing a method for visualizing a pattern in a dataset. The method comprises storing the dataset in persistent memory. The dataset comprises a corresponding discrete attribute value (e.g., mRNA count) for each first entity (e.g., mRNA that map to a particular gene) in a plurality of first entities for each respective second entity (e.g., a single cell) in a plurality of second entities. The dataset redundantly represents the corresponding discrete attribute value for each first entity in the plurality of first entities for each respective second entity in the plurality of second entities in both a compressed sparse row format and a compressed sparse column format in which, optionally, first entities for a respective second entity that have a null discrete attribute data value are discarded. The dataset is compressed in accordance with a blocked compression algorithm.

The method further comprises clustering the dataset using the discrete attribute value for each first entity in the plurality of first entities, or principal components derived therefrom, for each respective second entity in the plurality of second entities thereby assigning each respective second entity in the plurality of second entities to a corresponding cluster in a plurality of clusters. Each respective cluster in the plurality of clusters consists of a unique different subset of the second plurality of entities. The clustering loads less than the entirety of the dataset into the non-persistent memory at any given time during the clustering.

The method further comprise computing, for each respective first entity in the plurality of first entities for each respective cluster in the plurality of clusters, a difference in the discrete attribute value for the respective first entity across the respective subset of second entities in the respective cluster relative to the discrete attribute value for the respective first entity across the plurality of clusters other than the respective cluster. In this was a differential value is derived for each respective first entity in the plurality of first entities for each respective cluster in the plurality of clusters.

The method further comprises displaying in a first panel a heat map that comprises a representation of the differential value for each respective first entity in the plurality of first entities for each cluster in the plurality of clusters thereby visualizing the pattern in the dataset.

In some embodiments, the differential value for each respective first entity in the plurality of first entities for each respective cluster in the plurality of clusters is a fold change (e.g., $\log_2$ fold change, $\log_{10}$ fold change, etc.) in (i) a first measure of central tendency of the discrete attribute value for the first entity measured in each of the second entities in the plurality of second entities in the respective cluster and (ii) a second measure of central tendency of the discrete attribute value for the respective first entity measured in each of the second entities of all clusters other than the respective cluster.

In some embodiments, the method further comprises normalizing each discrete attribute value prior to computing the differential value for each respective first entity in the plurality of first entities for each respective cluster in the plurality of clusters. In some such embodiments, this normalizing comprises modeling the discrete attribute value of each first entity associated with each second entity in the plurality of entities with a negative binomial distribution having a consensus estimate of dispersion without loading the entire dataset into non-persistent memory.

In some embodiments, the method further comprises applying a dimension reduction technique to a respective plurality of principal component values of each second entity in the plurality of second entities, where each said respective plurality of principal component values is derived from the discrete attribute values of each first entity in a corresponding second entity in the plurality of entities, thereby determining a two dimensional data point for each second entity in the plurality of entities. In such embodiments, the method further comprises plotting each respective second entity in the plurality of entities in a second panel based upon the two-dimensional data point for the respective second entity. In some such embodiments, each cluster in the plurality of clusters is assigned a different graphic or color code, and each respective second entity in the plurality of entities is coded in the second panel with the different graphic or color code for the cluster the respective second entity has been assigned. In some embodiments, the dimension reduction technique is t-distributed stochastic neighbor embedding. In some embodiments, the dimension reduction technique is Sammon mapping, curvilinear components analysis, stochastic neighbor embedding, Isomap, maximum variance unfolding, locally linear embedding, or Laplacian Eigenmaps. In some embodiments, each of the respective plurality of principal component values is derived from the discrete attribute values of each first entity in a corresponding second entity in the plurality of entities by principal component analysis that is performed on a computer system remote from the visualization system prior to storing the dataset in persistent memory, and the dataset includes each of the respective plurality of principal component values.

In some embodiments, the clustering of the dataset is performed on a computer system remote from the visualization system prior to storing the dataset in persistent memory.

In some embodiments, the clustering of the dataset comprises hierarchical clustering, agglomerative clustering using a nearest-neighbor algorithm, agglomerative clustering using a farthest-neighbor algorithm, agglomerative clustering using an average linkage algorithm, agglomerative clustering using a centroid algorithm, or agglomerative clustering using a sum-of-squares algorithm.

In some embodiments, the clustering of the dataset comprises a Louvain modularity algorithm, k-means clustering, a fuzzy k-means clustering algorithm, or Jarvis-Patrick clustering.

In some embodiments, the clustering of the dataset comprises k-means clustering of the dataset into a predetermined number of clusters (e.g., between 2 and 50 clusters). In some embodiments, the clustering of the dataset comprises k-means clustering of the dataset into a number of clusters, where the number of clusters is provided by a use In some embodiments, each first entity in the plurality of first entities is a respective gene in a plurality of genes, each discrete attribute value is a count of transcript reads within the second entity that map to a respective gene in the plurality of genes, each second entity is a single cell, and the dataset represents a whole transcriptome shotgun sequencing experiment that quantifies gene expression from a single cell in counts of transcript reads mapped to the genes.

In some embodiments, each first entity in a particular second entity in the plurality of second entities is barcoded with a first barcode that is unique to the particular second entity.

In some embodiments, the discrete attribute value of each first entity in a particular second entity in the plurality of second entities is determined after the particular second entity has been separated from all the other second entities in the plurality of second entities into its own microfluidic partition.

Various embodiments of systems, methods and devices within the scope of the appended claims each have several aspects, no single one of which is solely responsible for the desirable attributes described herein. Without limiting the scope of the appended claims, some prominent features are described herein. After considering this discussion, and particularly after reading the section entitled "Detailed Description" one will understand how the features of various embodiments are used.

INCORPORATION BY REFERENCE

All publications, patents, and patent applications mentioned in this specification are herein incorporated by reference in their entireties to the same extent as if each individual publication, patent, or patent application was specifically and individually indicated to be incorporated by reference.

BRIEF DESCRIPTION OF THE DRAWINGS

The implementations disclosed herein are illustrated by way of example, and not by way of limitation, in the figures of the accompanying drawings. Like reference numerals refer to corresponding parts throughout the several views of the drawings.

DETAILED DESCRIPTION

Reference will now be made in detail to embodiments, examples of which are illustrated in the accompanying drawings. In the following detailed description, numerous specific details are set forth in order to provide a thorough understanding of the present disclosure. However, it will be apparent to one of ordinary skill in the art that the present disclosure may be practiced without these specific details. In other instances, well-known methods, procedures, components, circuits, and networks have not been described in detail so as not to unnecessarily obscure aspects of the embodiments.

The implementations described herein provide various technical solutions to detect a pattern in datasets. An example of such datasets are datasets arising from whole transcriptome shotgun sequencing pipelines that quantify gene expression in single cells in counts of transcript reads mapped to genes. Details of implementations are now described in conjunction with the Figures.

Figure 1A:
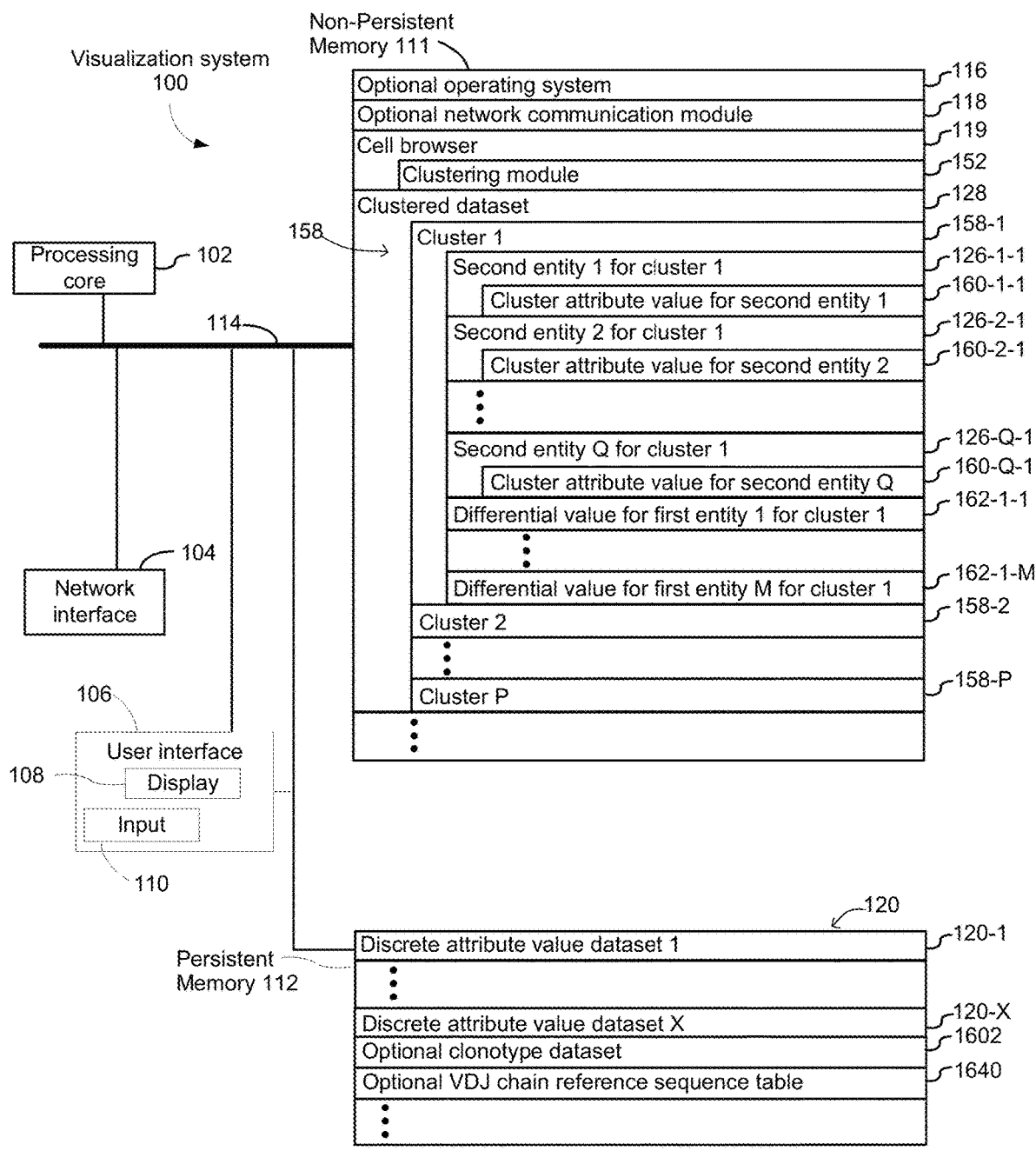
FIGS. 1A and 1B are an example block diagram illustrating a computing device in accordance with some implementations.

FIG. 1A is a block diagram illustrating a visualization system 100 in accordance with some implementations. The device 100 in some implementations includes one or more processing units CPU(s) 102 (also referred to as processors), one or more network interfaces 104, a user interface 106 comprising a display 108 and an input module 110, a non-persistent 111, a persistent memory 112, and one or more communication buses 114 for interconnecting these components. The one or more communication buses 114 optionally include circuitry (sometimes called a chipset) that interconnects and controls communications between system components. The non-persistent memory 111 typically includes high-speed random access memory, such as DRAM, SRAM, DDR RAM, ROM, EEPROM, flash memory, whereas the persistent memory 112 typically includes CD-ROM, digital versatile disks (DVD) or other optical storage, magnetic cassettes, magnetic tape, magnetic disk storage or other magnetic storage devices, magnetic disk storage devices, optical disk storage devices, flash memory devices, or other non-volatile solid state storage devices. The persistent memory 112 optionally includes one or more storage devices remotely located from the CPU(s) 102. The persistent memory 112, and the non-volatile memory device(s) within the non-persistent memory 112, comprise non-transitory computer readable storage medium. In some implementations, the non-persistent memory 111 or alternatively the non-transitory computer readable storage medium stores the following programs, modules and data structures, or a subset thereof, sometimes in conjunction with the persistent memory 112:

- an optional operating system 116, which includes procedures for handling various basic system services and for performing hardware dependent tasks;
- an optional network communication module (or instructions) 118 for connecting the visualization system 100 with other devices, or a communication network;
- a cell browser module 119 for selecting a discrete attribute value dataset 120 and optionally a clonotype dataset 1602A or 1602B from persistent memory and presenting information about the discrete attribute value dataset 120 and optionally the dataset 1602A or 1602B, where the discrete attribute value dataset 120 comprises a corresponding discrete attribute value 124 (e.g., count of transcript reads mapped to a single gene) for each first entity 122 (e.g., single gene) in a plurality of first entities (e.g., genome of a species) for each respective second entity 126 (e.g., single cell) in a plurality of second entities (e.g., population of cells) and the clonotype dataset 1602A or 1602B comprises clonotype information for a plurality of second entities;
- an optional clustering module 152 for clustering a discrete attribute value dataset 120 using the discrete attribute values 124 for each first entity 122 in the plurality of first entities for each respective second entity 126 in the plurality of second entities, or principal component values 164 derived therefrom, thereby assigning each respective second entity 126 in the plurality of second entities to a corresponding cluster 158 in a plurality of clusters in a clustered dataset 128; and
- optionally, all or a portion of a clustered dataset 128, the clustered dataset 128 comprising a plurality of clusters 158, each cluster 158 including a subset of second entities 126, and each respective cluster 158 including a differential value 162 for each first entity 122 across the second entities 126 of the subset of second entities for the respective cluster 158.

In some implementations, one or more of the above identified elements are stored in one or more of the previously mentioned memory devices, and correspond to a set of instructions for performing a function described above. The above identified modules, data, or programs (e.g., sets of instructions) need not be implemented as separate software programs, procedures, datasets, or modules, and thus various subsets of these modules and data may be combined or otherwise re-arranged in various implementations. In some implementations, the non-persistent memory 111 optionally stores a subset of the modules and data structures identified above. Furthermore, in some embodiments, the memory stores additional modules and data structures not described above. In some embodiments, one or more of the above identified elements is stored in a computer system, other than that of visualization system 100, that is addressable by visualization system 100 so that visualization system 100 may retrieve all or a portion of such data when needed.

FIG. 1A illustrates that the clustered dataset 128 includes a plurality of clusters 158 comprising cluster 1 (158-1), cluster 2 (158-2) and other clusters up to cluster P (158-P). Cluster 1 (158-1) is stored in association with second entity 1 for cluster 1 (126-1-1), second entity 2 for cluster 1 (126-2-1), and subsequent second entities up to second entity Q for cluster 1 (126-Q-1). As shown for cluster 1 (158-1), the cluster attribute value for second entity 1 (160-1-1) is stored in association with the second entity 1 for cluster 1 (126-1-1), the cluster attribute value for the second entity 2 (160-2-1) is stored in association with the second entity 2 for cluster 1 (126-2-1), and the cluster attribute value for the second entity Q (160-Q-1) is stored in association with the second entity Q for cluster 1 (126-Q-1). The clustered dataset 128 also includes differential value for first entity 1 for cluster 1 (162-1-1) and subsequent differential values up to differential value for first entity M for cluster 1 (162-1-M). Cluster 2 (158-2) and other clusters up to cluster P (158-P) in the clustered dataset 128 can include information similar to that in cluster 1 (158-1), and each cluster in the clustered dataset 128 is therefore not described in detail. A discrete attribute value dataset 120, which is store in the persistent memory 112, includes discrete attribute value dataset 120-1 and other discrete attribute value datasets up to discrete attribute value dataset 120-X.

Figure 1B:
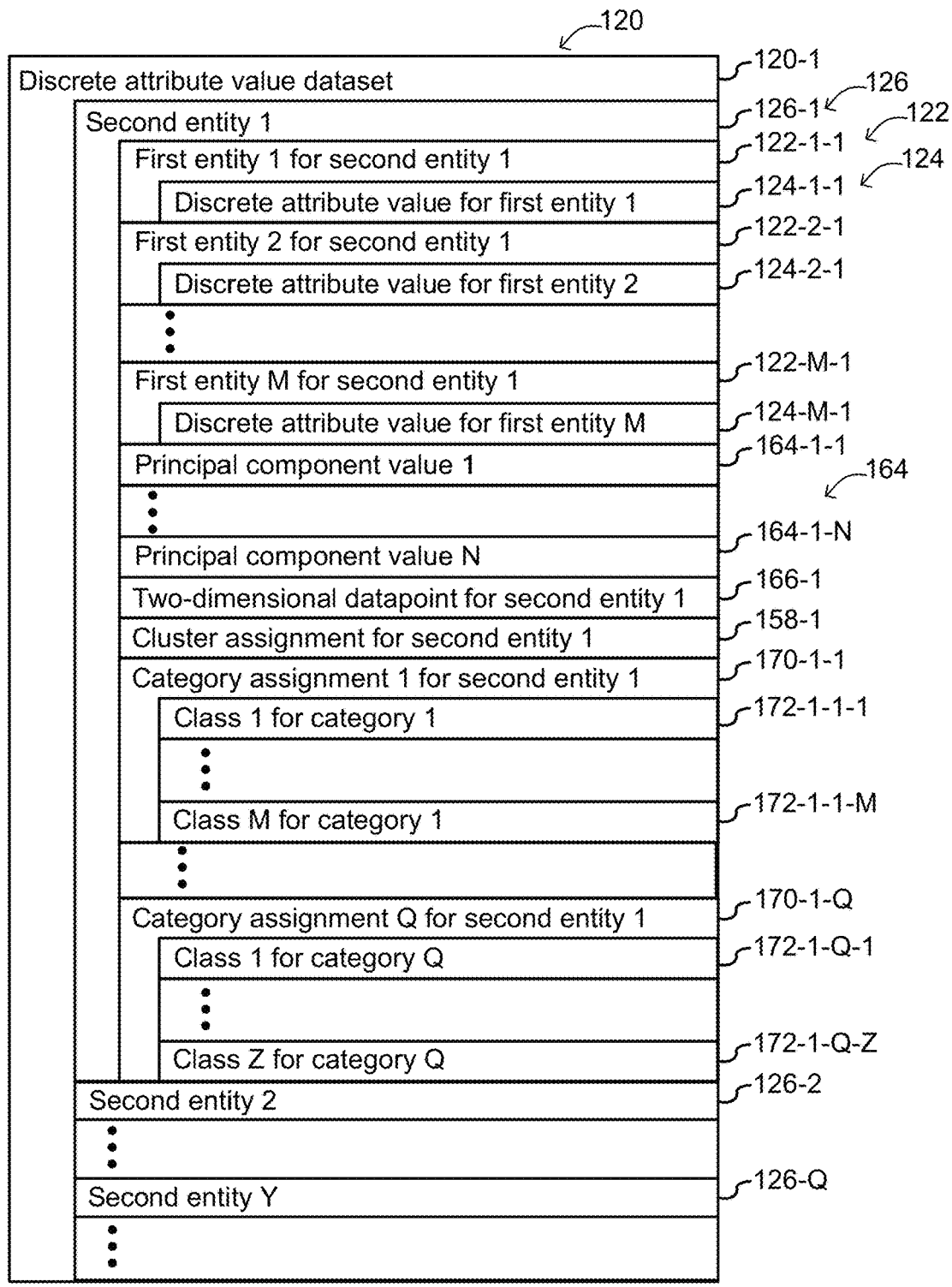

Referring to FIG. 1B, persistent memory 112 stores the discrete attribute value dataset 120 that comprises, for each respective second entity 126 in a plurality of second entities, a discrete attribute value 124 for each first entity 122 in a plurality of first entities. For example, as shown in FIG. 1B, a discrete attribute value dataset 120-1 (shown by way of example) includes information related to second entity 1 (126-1), second entity 2 (126-2) and other second entities up to second entity Y (126-Q). As shown for second entity 1 (126-1), the second entity 1 (126-1) includes discrete attribute value for first entity 1 124-1-1 of first entity 1 for second entity 1 122-1-1, discrete attribute value for first entity 2 124-2-1 of first entity 2 for second entity 1 122-2-1, and other discrete attribute values up to discrete attribute value for first entity M 124-M-1 of first entity M for second entity 1 122-M-1.

In some embodiments, the dataset further stores a plurality of principal component values 164 and/or a two-dimensional datapoint and/or a category 170 assignment for each respective second entity 126 in the plurality of second entities. FIG. 1B illustrates by way of example principal component value 1 164-1-1 and principal component value N 164-1-N stored for second entity 126-1. FIG. 1B also illustrates cluster assignment for second entity 1 158-1, category assignment 1 for second entity 1 170-1-1 including class 1 for category 1 172-1-1-1- and class M for category 1 172-1-1-M, and category assignment Q for second entity 1 170-1-Q including class 1 for category Q 172-1-Q-1- and class Z for category Q 172-1-Q-Z.

In some alternative embodiments, the discrete attribute value dataset 120 stores a two-dimensional datapoint 166 for each respective second entity 126 in the plurality of second entities (e.g., two-dimensional datapoint for second entity 1 166-1 in FIG. 1B) but does not store the plurality of principal component values 164. In some embodiments, each second entity represents a different cell, each first entity represents a number of mRNA measured in the different cell that maps to a respective gene in the genome of the cell, and the dataset further comprises the total RNA counts per second entity.

Although FIGS. 1A and 1B depict a "visualization system 100," the figures are intended more as functional description of the various features which may be present in computer systems than as a structural schematic of the implementations described herein. In practice, and as recognized by those of ordinary skill in the art, items shown separately could be combined and some items could be separated. Moreover, although FIG. 1A depicts certain data and modules in non-persistent memory 111, some or all of these data and modules may be in persistent memory 112. Further, while discrete attribute value dataset 120 is depicted as resident in persistent memory 112, a portion of discrete attribute value dataset 120 is, in fact, resident in non-persistent memory 111 at various stages of the disclosed methods.

Figure 2A:
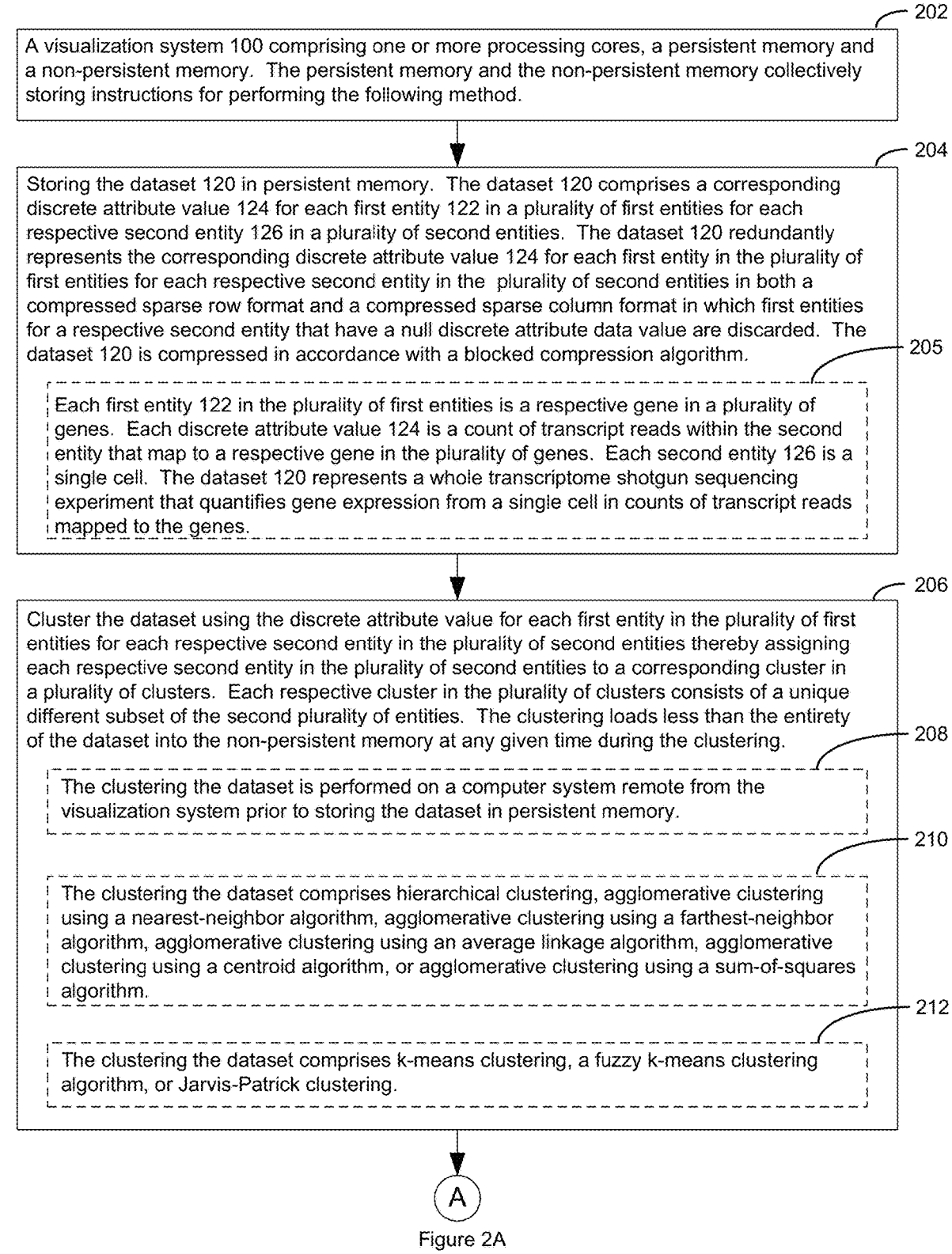
FIGS. 2A, 2B and 2C collectively illustrate an example method in accordance with an embodiment of the present disclosure, in which optional steps are indicated by broken lines.

While a system in accordance with the present disclosure has been disclosed with reference to FIGS. 1A and 1B, a method in accordance with the present disclosure is now detailed with reference to FIGS. 2A and 2B.

Block 202. One aspect of the present disclosure provides a visualization system 100. The visualization system 100 comprises one or more processing cores 102, a non-persistent memory 111 and a persistent memory 111, the persistent memory and the non-persistent memory collectively storing instructions for performing a method. A non-limiting example of a visualization system is collectively illustrated in FIGS. 1A and 1B.

Figure 3:
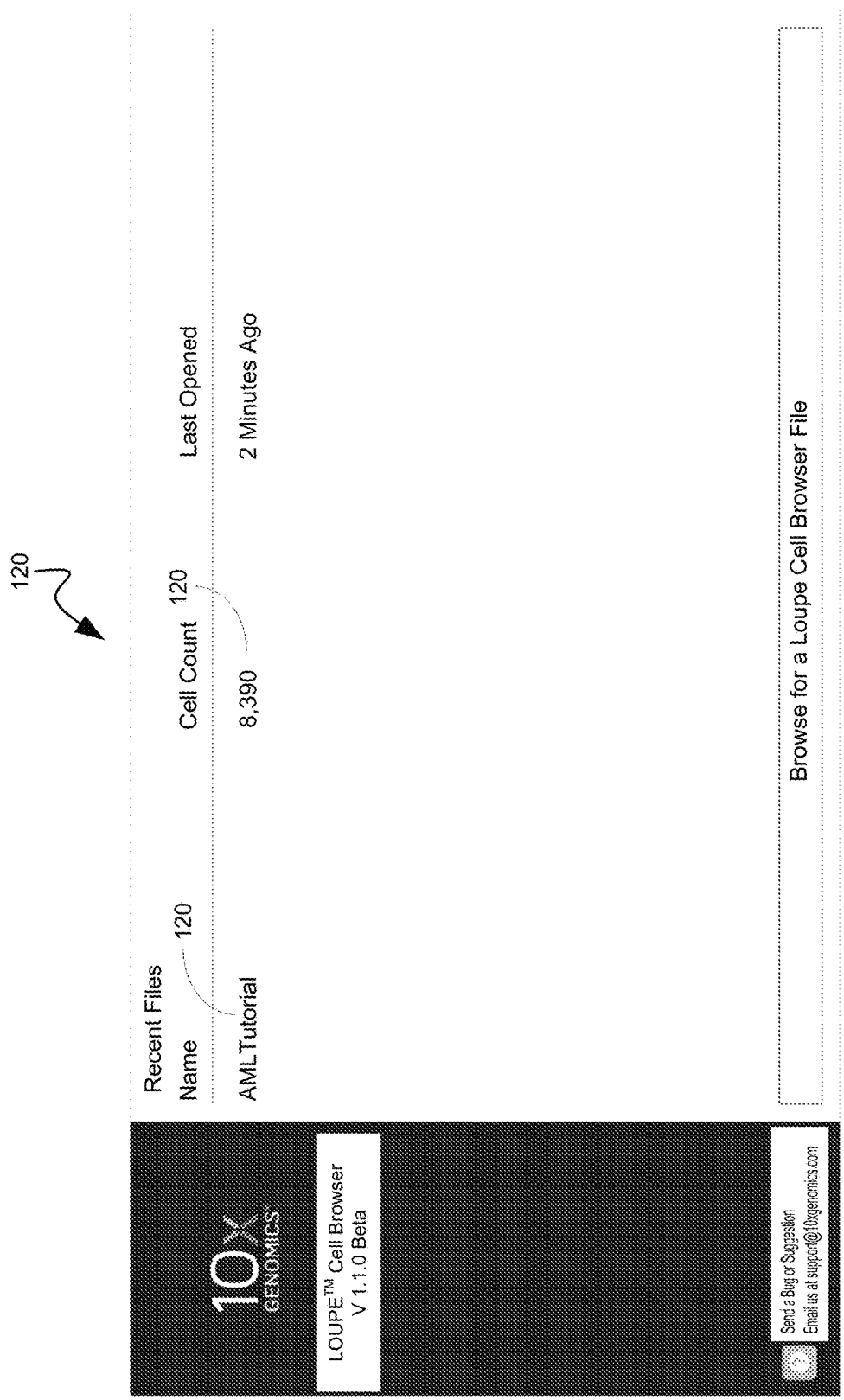
FIG. 3 illustrates a user interface for obtaining a dataset in accordance with some embodiments.

Block 204—Storing a discrete attribute value dataset 120 in persistent memory, and optionally storing a clonotype dataset 1602 in memory. A method in accordance with the systems and methods of the present disclosure comprises storing a discrete attribute value dataset 120 in persistent memory 112 and optionally a dataset 1602 in memory. Referring to FIG. 1B, the discrete attribute value dataset 120 comprises a corresponding discrete attribute value 124 for each first entity 122 in a plurality of first entities for each respective second entity 126 in a plurality of second entities. FIG. 3 illustrates the selection of a particular discrete attribute value dataset 120 using cell browser 119. In particular, FIG. 3 illustrates how the cell browser 119 provides some information regarding a given discrete attribute value dataset 120 such as its name, the number of second entities 126 (e.g., cells) represented by the discrete attribute value dataset 120, and the last time the discrete attribute value dataset was accessed.

Referring to block 205, in some embodiments, each first entity 122 in the plurality of first entities is a respective gene in a plurality of genes. Each discrete attribute value 124 is a count of transcript reads within the second entity that map to a respective gene in the plurality of genes. In such embodiments, each second entity 126 is a single cell. The discrete attribute value dataset 120 represents a whole transcriptome shotgun sequencing experiment that quantifies gene expression from a single cell in counts of transcript reads mapped to the genes. In some such embodiments, microfluidic partitions are used to partition very small numbers of mRNA molecules and to barcode those partitions. In some such embodiments, where discrete attribute values are measured from single cells, the microfluidic partitions are used to capture individual cells within each microfluidic droplet and then pools of single barcodes within each of those droplets are used to tag all of the contents (e.g., first entities 122) of a given cell. For example, in some embodiments, a pool of 750,000 barcodes is sampled to separately index each second entities' transcriptome by partitioning thousands of second entities into nanoliter-scale Gel Bead-In-EMulsions (GEMs), where all generated cDNA share a common barcode. Libraries are generated and sequenced from the cDNA and the barcodes are used to associate individual reads back to the individual partitions. In other words, each respective droplet (GEM) is assigned its own barcode and all the contents (e.g., first entities) in a respective droplet are tagged with the barcode unique to the respective droplet. In some embodiments, such droplets are formed as described in Zheng et al., 2016, Nat Biotchnol. 34(3): 303-311; or in See the Chromium, Single Cell 3' Reagent Kits v2. User Guide, 2017, 10X Genomics, Pleasanton, California, Rev. B, page, 2, each of which is hereby incorporated by reference. In some alternative embodiments, equivalent 5' chemistry is used rather than the 3' chemistry disclosed in these references.

In some embodiments there are tens, hundreds, thousands, tens of thousands, or one hundreds of thousands of such microfluidic droplets. In some such embodiments, at least seventy percent, at least eighty percent, at least ninety percent, at least ninety percent, at least ninety-five percent, at least ninety-eight percent, or at least ninety-nine percent of the respective microfluidic droplets contain either no second entity 126 or a single second entity 126 while the remainder of the microfluidic droplets contain two or more second entities 126. In other words, to achieve single second entity resolution, the second entities are delivered at a limiting dilution, such that the majority (~90-99%) of generated nanoliter-scale gel bead-in-emulsions (GEMs) contains no second entity, while the remainder largely contain a single second entity. See the Chromium, Single Cell 3' Reagent Kits v2. User Guide, 2017, 10X Genomics, Pleasanton, California, Rev. B, page, 2, which is hereby incorporated by reference. In some alternative embodiments, equivalent 5' chemistry is used rather than the 3' chemistry disclosed in this reference.

Within an individual droplet, gel bead dissolution releases the amplification primer into the partitioned solution. In some embodiments, upon dissolution of the single second entity 3' Gel Bead in a GEM, primers containing (i) an Illumina R1 sequence (read 1 sequencing primer), (ii) a 16 bp 10x Barcode, (iii) a 10 bp Unique Molecular Identifier (UMI) and (iv) a polydT primer sequence are released and mixed with cell lysate and Master Mix. Incubation of the GEMs then produces barcoded, full-length cDNA from poly-adenylated mRNA. After incubation, the GEMs are broken and the pooled fractions are recovered. See the Chromium, Single Cell 3' Reagent Kits v2. User Guide, 2017, 10X Genomics, Pleasanton, California, Rev. B, page, 2, which is hereby incorporated by reference. In some such embodiments, silane magnetic beads are used to remove leftover biochemical reagents and primers from the post GEM reaction mixture. Full-length, barcoded cDNA is then amplified by PCR to generate sufficient mass for library construction.

In this way, the first entities 122 can be mapped to individual genes in the genome of a species and therefore they can be sequenced and, furthermore, the first entities 122 of a given second entity 126 (e.g., cell) can be distinguished from the first entities of another second entity 126 (e.g. cell) based on the unique barcoded. This contrasts to bulk sequencing techniques in which all the cells are pooled together and the measurement profile is that of the first entities of the whole collection of the cells without the ability to distinguish the measurement signal of first entities by individual cells. An example of such measurement techniques is disclosed in United States Patent Application 2015/0376609, which is hereby incorporated by reference. As such, in some embodiments, each first entity in a particular second entity in the plurality of second entities is barcoded with a first barcode that is unique to the particular second entity. In some embodiments, the discrete attribute value 124 of each first entity 122 in a particular second entity 126 in the plurality of second entities is determined after the particular second entity 126 has been separated from all the other second entities in the plurality of second entities into its own microfluidic partition. In the case where each second entity 126 is a cell and each first entity is an mRNA that maps to a particular gene, such embodiments provide the ability to explore the heterogeneity between cells, which is one form of pattern analysis afforded by the systems and method of the present disclosure. In some such embodiments, because mRNA abundance it being measured, it is possible that the mRNA abundance in the cell sample may vary vastly from cell to cell. As such, the disclosed systems and methods enable the profiling of which genes are being expressed and at what levels in each of the cells and to use these gene profiles (records of discrete attribute values 124), or principal components derived therefrom, to cluster cells and identify populations of related cells. For instance, to identify similar gene profiles at different life cycle stages of the cell or different types of cells, different tissue, different organs, or other sources of cell heterogeneity.

As such, in some embodiments, each second entity 126 corresponds to a single cell, each first entity 122 associated with a corresponding second entity represents an mRNA (that maps to a gene that is in the genome of the single cell) and the discrete attribute value 124 is a number of copies of the mRNA that have been measured in the single cell. In some such embodiments, the discrete attribute value dataset 120 includes discrete attribute values for 1000 or more, 3000 or more, 5000 or more, 10,000 or more, or 15,000 or more mRNAs in each cell represented by the dataset. In some such embodiments, the discrete attribute value dataset 120 includes discrete attribute values for the mRNAs of 500 or more cells, 5000 or more cells, 100,000 or more cells, 250,000 or more cells, 500,000 or more cells, 1,000,000 or more cells, 10 million or more cells or 50 million or more cells. In some embodiments, each single cell is a human cell. In some embodiments, each second entity 126 represents a different human cell. In some embodiments, the discrete attribute value dataset 120 includes data for human cells of several different classes (e.g., representing different deceased states and/or wild type states). In such embodiments, the discrete attribute value 124 for a respective mRNA (first entity 122) in a given cell (second entity 126) is the number of mRNAs for the respective mRNA that were measured in the given cell. This will either be zero or some positive integer. In some embodiments, the discrete attribute value 124 for a given first entity 122 for a given second entity 126 is a number in the set $\{0, 1, \ldots, 100\}$. In some embodiments, the discrete attribute value 124 for a given first entity 122 for a given second entity 126 is a number in the set $\{0, 1, \ldots, 50\}$. In some embodiments, the discrete attribute value 124 for a given first entity 122 for a given second entity 126 is a number in the set $\{0, 1, \ldots, 30\}$. In some embodiments, the discrete attribute value 124 for a given first entity 122 for a given second entity 126 is a number in the set $\{0, 1, \ldots, N\}$, where N is a positive integer.

In some such embodiments, the discrete attribute value dataset 120 includes discrete attribute values for 1000 or more, 3000 or more, 5000 or more, 10,000 or more, or or more first entities 122 in each second entity 126 represented by the dataset. In some such embodiments, the discrete attribute value dataset 120 includes discrete attribute values 124 for the first entities of 500 or more second entities, 5000 or more second entities, 100,000 or more second entities, 250,000 or more second entities, 500,000 or more second entities, 1,000,000 or more second entities, 10 million or more second entities, or 50 million or more second entities.

As the above ranges indicate, the systems and methods of the present disclosure support very large discrete attribute value datasets 120 that may have difficulty being stored in the persistent memory 112 of conventional devices due to persistent memory 112 size limitations in conventional devices. Moreover, the systems and methods of the present disclosure are designed for data in which the sparsity is significantly more than twenty percent. The number of zero-valued elements divided by the total number of elements (e.g., m×n for an m×n matrix) is called the sparsity of the matrix (which is equal to 1 minus the density of the matrix. In the case of the mRNA expression data, where each first entity 122 represents a particular mRNA and each second entity 126 represents a different cell, while there are approximately twenty thousand genes in the human genome, most genes are not being expressed in a cell at any given time. Thus, it is expected that such data will have a sparsity approaching two percent in many instances. Thus, advantageously, to address the size constraints of the persistent memory (e.g., magnetic drives or solid state drives) 112 limitations of conventional computers, in some embodiments, the discrete attribute value dataset 120 is represented in a compressed sparse matrix representation that may be searched both on a first entity 122 basis and a second entity 126 basis. To accomplish this, the discrete attribute value dataset 120 redundantly represents the corresponding discrete attribute value 124 for each first entity 122 in a plurality of first entities for each respective second entity 126 in a plurality of second entities in both a compressed sparse row format and a compressed sparse column format in which first entities for a respective second entity that have a null discrete attribute data value are optionally discarded.

In some embodiments, the average density of the gene bar-code matrices that are used in the systems and methods of the present disclosure are on the order of two percent. Thus, if the first entities (e.g. genes) were viewed as a dense matrix, then only two percent of them would have data that is not zero. With a sparse matrix, all the zeroes are discarded. And so the sparse matrix allows for the dataset to fit in persistent memory 112. But with typical discrete attribute value datasets 120 of the present disclosure the memory footprint is still too high once the data for half a million second entities 126 or more is used. For this reason, both the row-oriented and column-oriented spare-matrix representations of the data are stored in persistent memory 112 in some embodiment in compressed blocks (e.g., bgzf blocks) to support quick differential-expression analysis, which requires examination of the data (e.g. the discrete attribute values of first entities) for individual second entities. In the case of the first entity "gene 3," access to the discrete attribute data for gene 3 works by looking at the address in the dataset for gene 3, which thereby identifies the block in which the data for gene 3 resides. As such, when doing differential expression for a subset of the second entities in the discrete attribute value dataset 120, the address of the individual second entity (e.g. cell) is first needed.

Accordingly, in some embodiments, the discrete attribute value dataset 120 is stored in compressed sparse row (CSR) format. Here the term "compressed sparse row" is used interchangeably with the term "compressed sparse column" (CSC) format. The CSR format stores a sparse m×n matrix M in row form using three (one-dimensional) arrays (A, IA, JA). Here, NNZ denotes the number of nonzero entries in M (note that zero-based indices shall be used here) and the array A is of length NNZ and holds all the nonzero entries of M in left-to-right top-to-bottom ("row-major") order. The array IA is of length m+1. It is defined by this recursive definition:

IA[0]=0;

IA[i]=IA[i−1]+(number of nonzero elements on the (i−1)$^{th}$ row in the original matrix).

Thus, the first m elements of IA store the index into A of the first nonzero element in each row of M, and the last element IA[m] stores NNZ, the number of elements in A, which can be also thought of as the index in A of first element of a phantom row just beyond the end of the matrix M. The values of the i$^{th}$ row of the original matrix is read from the elements A[IA[i]] to A[IA[i+1]−1] (inclusive on both ends), e.g. from the start of one row to the last index just before the start of the next.

The third array, JA, contains the column index in M of each element of A and hence is of length NNZ as well.

For example, the matrix M $$\begin{pmatrix} 0 & 0 & 0 & 0 \\ 5 & 8 & 0 & 0 \\ 0 & 0 & 3 & 0 \\ 0 & 6 & 0 & 0 \end{pmatrix}$$

is a 4×4 matrix with 4 nonzero elements, hence
A=[5 8 3 6]
IA=[0 0 2 3 4]
JA=[0 1 2 1]

In one implementation of the matrix M above, each row represents a different second entity 126 and each element of a given row represents a different first entity 122 associated with the different second entity. Further, the value at a given matrix element represents the discrete attribute value for the first entity 124.

In some embodiments, the discrete attribute value dataset 120 is also stored in compressed sparse column (CSC or CCS) format. A CSC is similar to CSR except that values are read first by column, a row index is stored for each value, and column pointers are stored. For instance, CSC is (val, row_ind, col_ptr), where val is an array of the (top-to-bottom, then left-to-right) non-zero values of the matrix; row_ind is the row indices corresponding to the values; and, col_ptr is the list of val indexes where each column starts.

Figure 4:
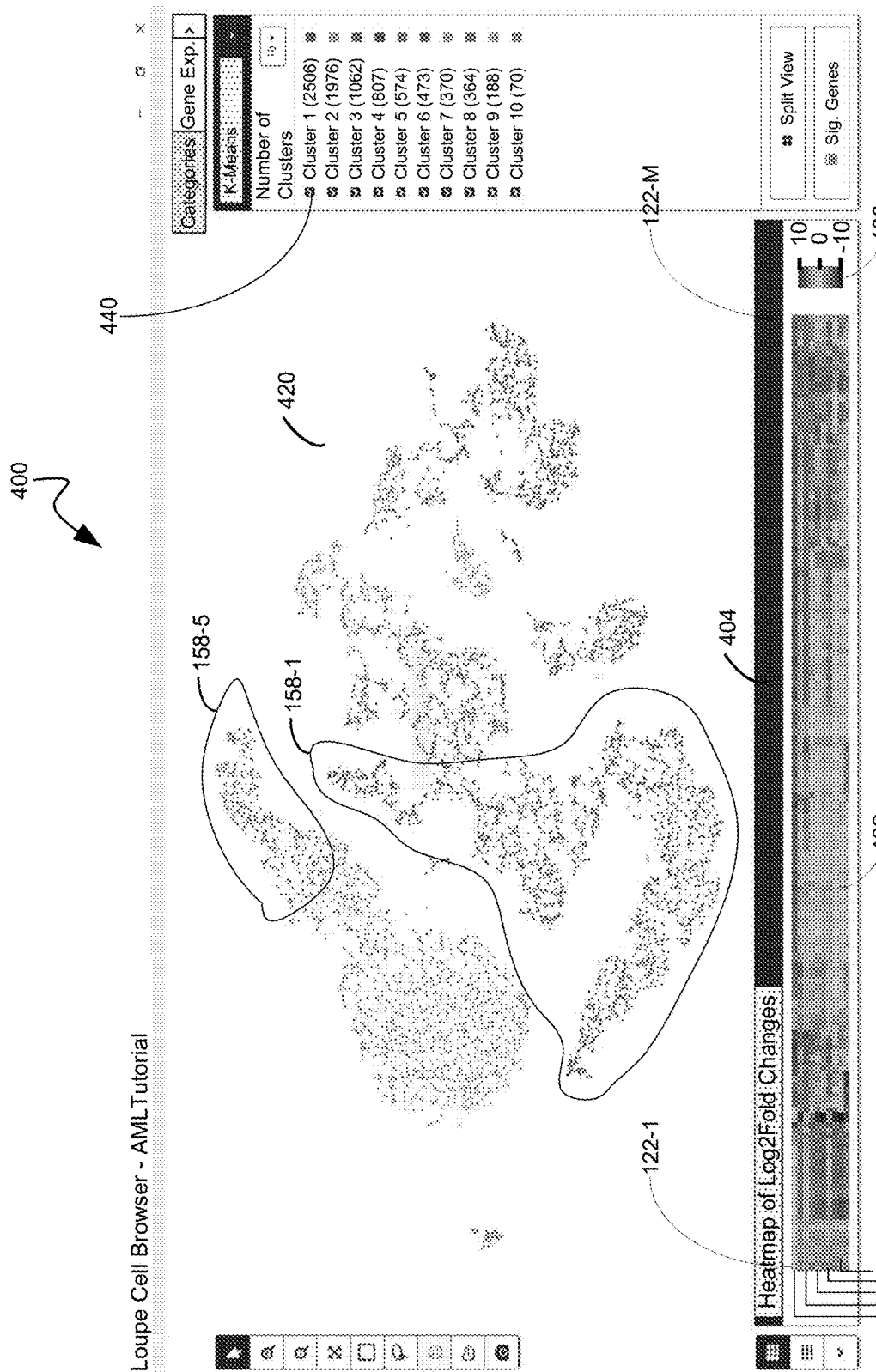
FIG. 4 illustrates an example display in which a heat map that comprises a representation of the differential value for each respective first entity in a plurality of first entities for each cluster in a plurality of clusters is displayed in a first panel while each respective second entity in a plurality of entities is displayed in a second panel based upon a dimension reduced two-dimensional data point for the respective second entity in accordance with some embodiments.

In addition to redundantly representing the corresponding discrete attribute value 124 for each first entity 122 in a plurality of first entities for each respective second entity 126 in a plurality of second entities in both a compressed sparse row format and a compressed sparse column format, the discrete attribute value dataset 120 is compressed in accordance with a blocked compression algorithm. In some such embodiments, this involves compressing the A and JA data structures but not the IA data structures using a block compression algorithm such as bgzf and storing this in persistent memory 112. Moreover, an index for compressed A and an index for compressed JA enable random seeks of the compressed data. In this way, although the discrete attribute value dataset 120 is compressed, it can be efficiently obtained and restored. All that needs to be done to obtain specific discrete attribute values 124 is seek to the correct block in persistent memory 112 and un-compress the block that contains the values and read them from within that block. Thus, certain operations, for example, like computing a differential heat map described below with reference to FIG. 4, is advantageously fast with the systems and method of present disclosure because it is known ahead of time which block of compressed data the desired attribute values 124 are in. That is, the systems and methods of the present disclosure know which row that a particular sought after second entity is from looking at the row address value of the sparse matrix, which is stored outside of the compressed values. So, all that is needed is to figure out which block has the sought after first entity data and what their discrete attribute values are, the algorithm jumps to the spot in the correct block (e.g., bgzf block) that contains the data.

In some embodiments, the discrete attribute value dataset 120 represents a whole transcriptome shotgun sequencing (RNA-seq) experiment that quantifies gene expression from a single cell in counts of transcript reads mapped to the genes.

Figure 16A:
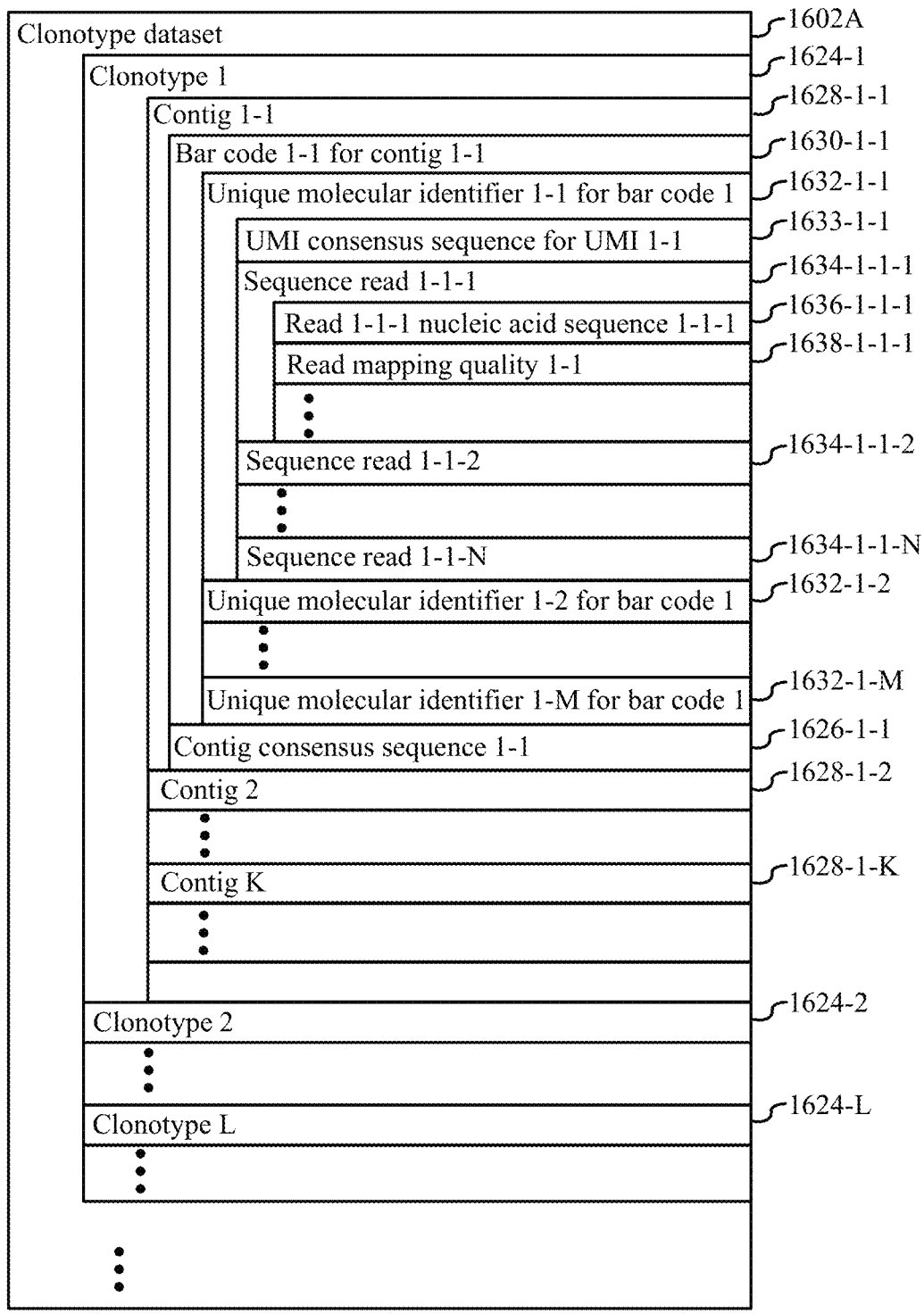
FIG. 16A illustrates an unindexed clonotype dataset in accordance with some embodiments of the present disclosure.
Figure 16B:
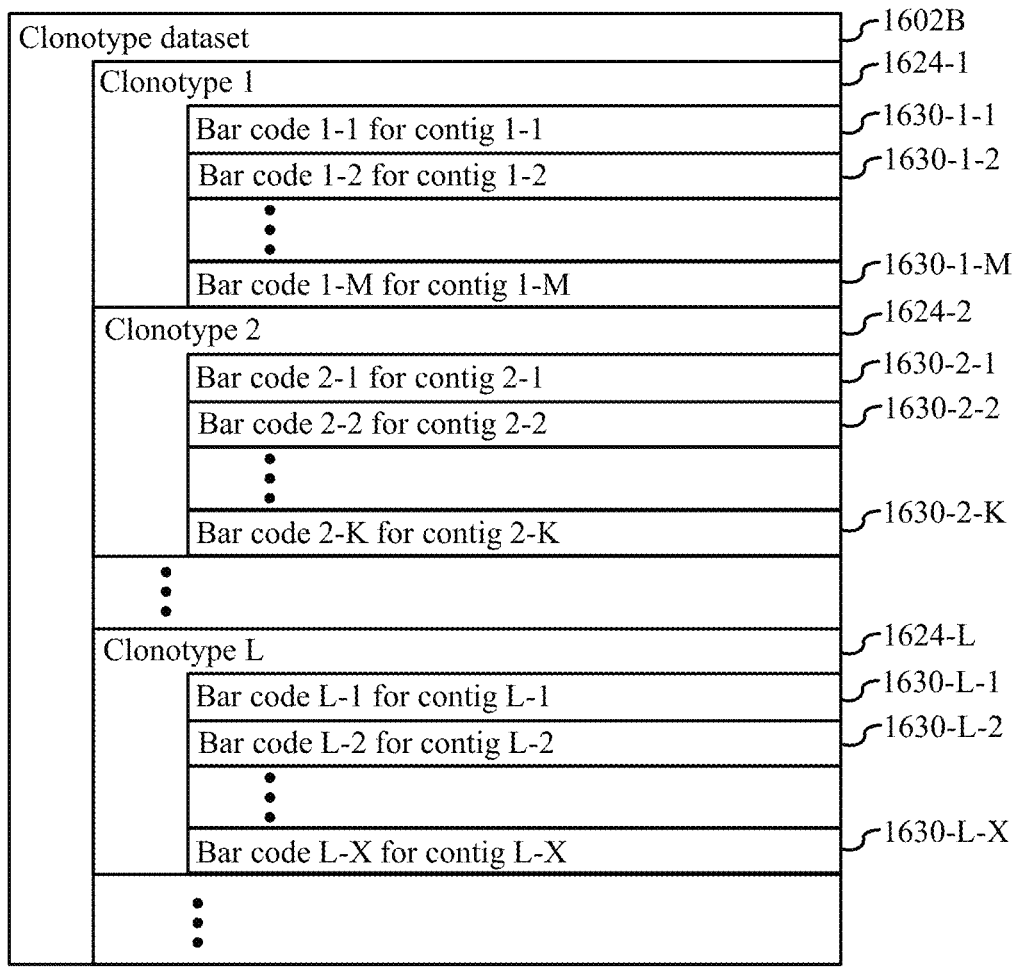
FIG. 16B illustrates an indexed clonotype dataset in accordance with some embodiments of the present disclosure.

In some embodiments, an unindexed clonotype dataset 1602A or indexed clonotype dataset 1602B is also stored in memory. In some such embodiments the unindexed clonotype dataset 1602A comprises a clonotype dataset such as the clonotype dataset disclosed in FIG. 1 and accompanying disclosure describing FIG. 1 of United States Patent Application No. 62/508,947, entitled "Systems and Methods for Analyzing Datasets," filed May 19, 2017, which is hereby incorporated by reference. In some embodiments, the unindexed clonotype dataset 1602A is as illustrated in FIG. 16A. In some embodiments, the indexed clonotype dataset 1602B is as illustrated in FIG. 16B. In some embodiments, the unindexed clonotype dataset 1602A and/or indexed clonotype dataset 1602B is not compressed in the manner described above for the discrete attribute value dataset 120. In typical embodiments, the unindexed clonotype dataset 1602A and/or the indexed clonotype dataset 1602B is a standalone independent data structure that is not a part of the discrete attribute value dataset 120.

In some embodiments, the clonotype dataset 1602 (1602A or 1602B) includes the V(D)J clonotype of the B-cell immunoglobulin receptor of any B-cells, or the T-cell receptor of any T-cells, that were in the biological sample represented by the corresponding discrete attribute value dataset 120. B-cells are highly diverse, each expressing a practically unique B-cell immunoglobulin receptor (BCR). There are approximately $10^{10}$-$10^{11}$ B-cells in a human adult. See Ganusov et al., 2007, "Do most lymphocytes in humans really reside in the gut?," Trends Immunol, 208(12), pp. 514-518, which is hereby incorporated by reference. B-cells are important components of adaptive immunity, and directly bind to pathogens through B-cell immunoglobulin receptors (BCRs) expressed on the cell surface of the B-cells. Each B-cell in an organism (e.g. human) expresses a different BCR that allows it to recognize a particular set of molecular patterns. Individual B-cells gain this specificity during their development in the bone marrow, where they undergo a somatic rearrangement process that combines multiple germline-encoded gene segments to procures the BCR, as illustrated in FIG. 1 of Yaari and Kleinstein, 2015, "Practical guidelines for B-cell repertoire sequencing analysis," Genome Medicine 7:121, which is hereby incorporated by reference. Human antibody molecules (and B-cell immunoglobulin receptors) are composed of heavy and light chains (each of which contains both constant (C) and variable (V) regions), which are encoded by genes on three loci: the immunoglobulin heavy locus (IGH@) on chromosome 14, containing the gene segments for the immunoglobulin heavy chain, the immunoglobulin kappa (κ) locus (IGK@) on chromosome 2, containing the gene segments for part of the immunoglobulin light chain, the immunoglobulin lambda (λ) locus (IGL@) on chromosome 22, containing the gene segments for the remainder of the immunoglobulin light chain. Each heavy chain and light chain gene contains multiple copies of three different types of gene segments for the variable regions of the antibody proteins. For example, the human immunoglobulin heavy chain region contains two Constant (Cμ and Cδ) gene segments and 44 Variable (V) gene segments plus 27 Diversity (D) gene segments and 6 Joining (J) gene segments. See Matsuda et al., 1998, "The complete nucleotide sequence of the human immunoglobulin heavy chain variable region locus," The Journal of Experimental Medicine. 188 (11): 2151-62, doi:10.1084/jem.188.11.2151; and Li et al., 2004, "Utilization of Ig heavy chain variable, diversity, and joining gene segments in children with B-lineage acute lymphoblastic leukemia: implications for the mechanisms of VDJ recombination and for pathogenesis," Blood. 103 (12): 4602-9, doi:10.1182/blood-2003-11-3857, each of which is incorporated by reference. The light chains also possess two Constant (Cp. and CO gene segments and numerous V and J gene segments, but do not have D gene segments. DNA rearrangement causes one copy of each type of gene segment to go in any given lymphocyte, generating an enormous antibody repertoire, although some are removed due to self-reactivity. Most T-cell receptors are composed of an alpha chain and a beta chain. The T-cell receptor genes are similar to immunoglobulin genes in that they too contain multiple V, D and J gene segments in their beta chains (and V and J gene segments in their alpha chains) that are rearranged during the development of the lymphocyte to provide that cell with a unique antigen receptor. The T-cell receptor in this sense is the topological equivalent to an antigen-binding fragment of the antibody, both being part of the immunoglobulin superfamily. B-cells and T-cells are defined by their clonotype, that is the identity of the final rearrangement of the V(D)J regions into the heavy and light chains of the B-cell immunoglobulin receptor, in the case of B-cells, or into each chain of the T-cell receptor in the case of T-cells. Because of the rearrangement undergone of the V(D)J region in T-cells and B-cells, only parts of the V(D)J regions (the V, D, and J segments) can be traced back to segments encoded in highly repetitive regions of the germline that are not typically sequenced directly from the germ line DNA. Furthermore, the V, D, and J segments can be significantly modified during the V(D)J rearrangement process and through in the case of B-cells somatic hypermutation. As such, there are typically no pre-existing full-length templates to align to sequence reads of the V(D)J regions of T-cell and B-cell receptors. Clonal grouping, referred to herein as clonotyping, involves clustering the set of B-cell receptor V(D)J) sequences (in the case of B-cells) or the set of T-cell receptor V(D)J sequences, in the case to T-cells into clones, which are defined as a group of cells that are descended from a common ancestor. Unlike the case of T-cells, members of a B-cell clone do not carry identical V(D)J sequences, but differ because of somatic hypermutation. Thus, defining clones (clonotyping) based on BCR sequence data requires machine learning techniques in some instances. See, for example, Chen et al., 2010, "Clustering-based identification of clonally-related immunoglobulin gene sequence sets," Immunome Res. 6 Suppl 1:S4; and Hershberg and Prak, 2015, "The analysis of clonal expansion in normal and autoimmune B cell repertoires," Philos Trans R Soc Lond B Biol Sci. 370(1676), each of which is hereby incorporated by reference. Referring to FIG. 16, in some embodiments, the clonotype dataset 1602 comprises a plurality of clonotypes 1624 represented by a population of second entities that have been measured, and for each chain in each clonotype 1624 (e.g. T-cell receptor α chain, T-cell receptor β chain, B-cell heavy chain, B-cell light chain, etc.) in the plurality of clonotypes represented by a consensus sequence for a VDJ region 1626 of the chain, where the consensus sequence for the V(D)J region 1626 is derived from a plurality of contigs 1628 of that chain in that clonotype, each contig 1628 associated with (i) a barcode 1630, (ii) one or more unique molecular identifiers 1632, and (iii) a contig consensus sequence 1626 across the sequence reads of the unique molecular identifier, each unique molecular identifier 1632 supported by a plurality of sequence reads 1634 that contribute to the contig consensus sequence 1626, each sequence read including information such as a read nucleic acid sequence 1636 and a read mapping quality 1638. For example, as shown in FIG. 16A, contig 1-1 1628-1-1 is associated with bar code 1-1 1630-1-1, unique molecular identifier 1-1 for bar code 1 1632-1-1, unique molecular identifier 1-2 for bar code 1 1632-1-2, and unique molecular identifier 1-M for bar code 1 1632-1-M, and contig consensus sequence 1-1 1626-1-1. As also shown in FIG. 16A, the unique molecular identifier 1-1 for bar code 1 1632-1-1 is associated with UMI consensus sequence for UMI 1-1 1633-1-1, sequence read 1-1-1 1634-1-1-1, sequence read 1-1-2 1634-1-1-2, and sequence read 1-N 1634-1-1-N. The sequence read 1-1-1 1634-1-1-1 is associated with read 1-1-1 nucleic acid sequence 1-1-1 1636-1-1-1 and read mapping quality 1-1 1638-1-1-1.

In some embodiments, the unindexed clonotype dataset 1602A further includes, or is electronically associated with, a VDJ chain reference sequence table 1640 that includes the reference sequence of all the V genes and J genes in a genome, or at least the ones represented by a given clonotype dataset 1602.

In some embodiments the unindexed clonotype dataset 1602A is organized as a series of data blocks with a master JSON table of contents at the beginning of the file and a JSON table of contents describing the addresses and structure of each block at the end of the file. In some embodiments there are a plurality of blocks in the unindexed clonotype dataset 1602A.

In some embodiments, one such block constitutes a database (e.g., a sqlite3 database) containing one table 1624 for each clonotype, T-cell receptor chain reference sequences, T-cell receptor chain consensus sequences, contigs, and a secondary table mapping cell barcodes to clonotypes 1624. This database is queried to create the clonotype list, sorted by frequency, and again queried to populate the chain visualization with data when clicking on the chain in the user interface disclosed herein. Each row in the reference, consensus and contig tables also include file offsets and lengths that encode the location of more detailed and hierarchical information about that entity within a set of JSON files, stored within other blocks in the plurality of block. Finally, alignment and sequence information for each reference and consensus are stored in the database for future debugging and troubleshooting.

In some embodiments, one or more blocks contain a reference annotation JSON file, which is a complete set of information about each reference per T-cell receptor chain or B-cell receptor chain. This block is equivalent to VDJ chain reference sequence table 1640 illustrated in FIG. 1B. Accordingly, in some embodiments, VDJ chain reference sequence table 1640 is a component of the unindexed clonotype dataset 1602A.

In some embodiments, one or more blocks contain a consensus annotation, e.g., as JSON file, which is a complete set of information about each consensus sequence 1626 (FIG. 16) per T-cell receptor chain.

In some embodiments, one or more blocks contains a contig annotation, e.g. as a JSON file, which is a complete set of information about each contig 1628. Referring to FIG. 16A, a contig 1628 is the assembled sequence of a transcript that encodes a chain (e.g. a chain, chain of a T-cell receptor, heavy chain or light chain of a B-cell receptor. Thus, in the case of a single T-cell it is expected that there would be at least one contig 1628 for the α chain and at least one contig 1628 for the R chain. In the case of a single B-cell, it is expected that there would be at least one contig 1628 for each chain of the B-cell receptor (e.g., at least one contig for the heavy chain and at least one contig 1628 for the light chain).

In some embodiments, one or more blocks contain a reference sequence, e.g., in FASTA format, that is used during unindexed clonotype dataset 1602A file creation or indexed clonotype dataset 1602B file creation, not during cell browser 119 operation, for debugging purposes.

In some embodiments, one or more blocks contain a reference alignment, e.g. as a BAM file, which stores how chain consensus sequence/contigs 128 differ from the reference sequence. This is typically used during unindexed clonotype dataset 1602A creation as opposed to during cell browser 119 operation, for instance, for debugging purposes.

In some embodiments, one or more blocks contain a reference alignment BAM index for the above identified BAM file to accelerates sequence alignment queries.

In some embodiments, one or more blocks contain a consensus sequence, e.g., in FASTA format, that is typically used during unindexed clonotype dataset 1602A creation as opposed to during cell browser 119 operation.

In some embodiments, one or more blocks contain consensus alignments BAM file that stores how contig sequences differ from the consensus, that is typically used during unindexed clonotype dataset 1602A creation as opposed to during cell browser 119 operation.

In some embodiments, one or more blocks contain a contig BAM index which stores where to find read information for individual contigs.

In some embodiments, one or more blocks contain a contig BED file that stores gene annotations for each contig.

In some embodiments, one or more blocks contain a contig FASTA file that stores sequences of each contig.

In some embodiments, among other processes disclosed herein, there are two processes that are initiated when a user runs the cell browser 119 (i) a backend server process that reads the unindexed clonotype dataset 1602A (which is typically an independent dataset apart from discrete attribute value dataset 120) and returns JSON responses and (ii) a front-end web application that processes the JSON into a visualization, and handles user input. In some embodiments, the backend server process extracts the sqlite3 database bytes out of the unindexed clonotype dataset 1602A into a temporary location. In some such embodiments, the server process holds a relation between an unindexed clonotype dataset 1602A and its associated sqlite3 database file, discussed above, in memory, and directs all queries pertaining to the unindexed clonotype dataset 1602A to that database. When shutting down, the server process cleans itself up by removing all database files that were opened during the session.

In some embodiments, cell browser 119 or a back-end server process pre-processes the non-indexed clonotype dataset 1602A having the format described above in the manner described above. Then, the cell browser 119 or a back-end server process saves the data into an indexed clonotype dataset 1602B (e.g., as a .cloupe file) to the level of barcodes 1630. In other words, in such embodiments, once the non-indexed clonotype dataset 1602A has been indexed to a corresponding discrete attribute value dataset 120 based on common sequence reads between the two datasets, in such embodiments, the now-indexed clonotype dataset 1602B is saved for use by the cell browser 119, for example in the format illustrated in FIG. 16B, to provide the filtering functions disclosed herein with reference to FIGS. 17-24, and this indexed clonotype dataset 1602B illustrated in FIG. 16B comprises the fields indicated in FIG. 16A as deep as the barcode (1630-1-1) within the cell browser 119 .cloupe file and does not embed the files referred to above. In other words, the indexed clonotype dataset 1602B, illustrated in FIG. 16B, now indexed to a corresponding discrete attribute value set 120, does not include the unique molecular identifiers 1632, UMI consensus sequence 1633, sequence reads 1634, read nucleic sequences 1636, or read map quality 1638 illustrated in FIG. 16A. In some embodiments, the indexed clonotype dataset 1602B includes, for each respective clonotype 1624 (e.g., clonotypes 1, 2, L 1624-1, 1624-2, 1624-L, respectively) the list of barcodes 1630 (e.g., bar code 1-1 for contig 1-1 1630-1-1, bar code 1-2 for contig 1-2 1630-1-2, bar code 1-M for contig 1-M 1630-1-M, bar code 2-1 for contig 2-1 1630-2-1, bar code 2-2 for contig 2-2 1630-2-2, bar code 2-K for contig 2-K 1630-2-K, bar code L-1 for contig L-1 1630-L-1, bar code L-2 for contig L-2 1630 L-2, bar code L-X for contig L-X 1630 L-X) spanning any of the contigs 1628 (e.g., contig 1-1 1628-1-1, contig 2 1628-1-2, contig K 1628-1-K) associated with the respective clonotype 1624 with the proviso that each such barcode 1630 also represents a second entity 126 in the discrete attribute dataset 120. In other words, when the clonotype information is stored as an indexed clonotype dataset 1602B (e.g. in the cell browser 119 file) an index per clonotype 1624 is retained of the barcodes 1630 that (a) were mapped to contigs 1628 within that clonotype 1624 in the unindexed clonotype dataset 1602A from the VDJ pipeline and (b) are found in the discrete attribute value dataset.

In some embodiments, once the indexed clonotype dataset 1602B is loaded into the cell browser 119, the cell browser 119 handles all queries (such as cluster membership and filtering disclosed herein with reference to FIGS. 17 through 24). In other embodiments, the full complexity of the non-indexed clonotype data structure 1602A is retained and used by the cell browser 119 in such embodiments. As such, in some embodiments, reference to the clonotype dataset 1602 below is in reference to the non-indexed clonotype dataset 1602A format of FIG. 16A or the indexed clonotype dataset 1602B format of FIG. 16B.

Block 206—clustering the dataset. In some embodiments, once a discrete attribute value dataset 120 is selected, e.g., using the interface illustrated in FIG. 3, the discrete attribute values 124 in the discrete attribute value dataset 120 are used by the clustering module 152 of the cell browser 119 to take the discrete attribute value dataset 120 and perform cluster visualization, as illustrated in FIG. 4. In typical embodiments, principal component values stored in the discrete attribute value dataset 120 that have been computed by the method of principal component analysis using the discrete attribute values 124 of the first entities 122 across the plurality of second entities 126 of the discrete attribute value dataset 120 are used by the clustering module 152 of the cell browser 150 to take the discrete attribute value dataset 120 and perform cluster visualization, as illustrated in FIG. 4. Principal component analysis (PCA) is a mathematical procedure that reduces a number of correlated variables into a fewer uncorrelated variables called "principal components". The first principal component is selected such that it accounts for as much of the variability in the data as possible, and each succeeding component accounts for as much of the remaining variability as possible. The purpose of PCA is to discover or to reduce the dimensionality of the dataset, and to identify new meaningful underlying variables. PCA is accomplished by establishing actual data in a covariance matrix or a correlation matrix. The mathematical technique used in PCA is called eigen analysis: one solves for the eigenvalues and eigenvectors of a square symmetric matrix with sums of squares and cross products. The eigenvector associated with the largest eigenvalue has the same direction as the first principal component. The eigenvector associated with the second largest eigenvalue determines the direction of the second principal component. The sum of the eigenvalues equals the trace of the square matrix and the maximum number of eigenvectors equals the number of rows (or columns) of this matrix. See, for example, Duda, Hart, and Stork, *Pattern Classification*, Second Edition, John Wiley & Sons, Inc., NY, 2000, pp. 115-116, which is hereby incorporated by reference.

Referring to block 208, in some embodiments, such clustering is performed at a prior time on a remote computer system. That is, in some embodiments, the cluster assignment of each second entity 126 was already performed prior to storing the discrete attribute value dataset 120. In such embodiments, the discrete attribute value dataset 120 includes the cluster assignment 158 of each second entity, as illustrated in FIG. 1B.

In some embodiments, the cluster assignment of each second entity 126 is not performed prior to storing the discrete attribute value dataset 120 but rather all the principal component analysis computation of the principal component values 164 is performed prior to storing the discrete attribute value dataset 120. In such embodiments, clustering is performed by the clustering module 152 of FIG. 1A.

For clustering in accordance with one embodiment of the systems and method of the present disclosure, regardless at what stage it is performed, consider the case in which each second entity 126 is associated with ten first entities 122. In such instances, each second entity 126 can be expressed as a vector:

$$\vec{X}_{10} = \{x_1, x_2, x_3, x_4, x_5, x_6, x_7, x_8, x_9, x_{10}\}$$

where $X_i$ is the discrete attribute value 124 for the first entity i 124 associated with the second entity 126. Thus, if there are one thousand second entities 126, 1000 vectors are defined. Those second entities 126 that exhibit similar discrete attribute values across the set of first entities 122 of the dataset 102 will tend to cluster together. For instance, in the case where each second entity 126 is an individual cell, the first entities 122 correspond to mRNA mapped to individual genes within such individual cells, and the discrete attribute values 124 are mRNA counts for such mRNA, it is the case in some embodiments that the discrete attribute value dataset 120 includes mRNA data from one or more cell types (e.g., diseased state and non-diseased state), two or more cell types, three or more cell types. In such instances, it is expected that cells of like type will tend to have like values for mRNA across the set of first entities (mRNA) and therefor cluster together. For instance, if the discrete attribute value dataset 120 includes class a: cells from subjects that have a disease, and class b: cells from subjects that do not have a disease, an ideal clustering classifier will cluster the discrete attribute value dataset 120 into two groups, with one cluster group uniquely representing class a and the other cluster group uniquely representing class b.

For clustering in accordance with another embodiment of the systems and method of the present disclosure, regardless at what stage it is performed, consider the case in which each second entity 126 is associated with ten principal component values that collectively represent the variation in the discrete attribute values of a large number of first entities 122 of a given second entity with respect to the discrete attribute values of corresponding first entities 122 of other second entities in the dataset. In such instances, each second entity 126 can be expressed as a vector:

$$\vec{X}_{10} = \{x_1, x_2, x_3, x_4, x_5, x_6, x_7, x_8, x_9, x_{10}\}$$

where $X_i$ is the principal component value 164 i associated with the second entity 126. Thus, if there are one thousand second entities 126, one those vectors are defined. Those second entities 126 that exhibit similar discrete attribute values across the set of principal component values 164 will tend to cluster together. For instance, in the case where each second entity 126 is an individual cell, the first entities 122 correspond to mRNA mapped to individual genes within such individual cells, and the discrete attribute values 124 are mRNA counts for such mRNA, it is the case in some embodiments that the discrete attribute value dataset 120 includes mRNA data from one or more cell types (e.g., diseased state and non-diseased state), two or more cell types, three or more cell types. In such instances, it is expected that cells of like type will tend to have like values for mRNA across the set of first entities (mRNA) and therefor cluster together. For instance, if the discrete attribute value dataset 120 includes class a: cells from subjects that have a disease, and class b: cells from subjects that have a disease, an ideal clustering classifier will cluster the discrete attribute value dataset 120 into two groups, with one cluster group uniquely representing class a and the other cluster group uniquely representing class b.

Clustering is described on pages 211-256 of Duda and Hart, *Pattern Classification and Scene Analysis*, 1973, John Wiley & Sons, Inc., New York, (hereinafter "Duda 1973") which is hereby incorporated by reference in its entirety. As described in Section 6.7 of Duda 1973, the clustering problem is described as one of finding natural groupings in a dataset. To identify natural groupings, two issues are addressed. First, a way to measure similarity (or dissimilarity) between two samples is determined. This metric (similarity measure) is used to ensure that the samples in one cluster are more like one another than they are to samples in other clusters. Second, a mechanism for partitioning the data into clusters using the similarity measure is determined.

Similarity measures are discussed in Section 6.7 of Duda 1973, where it is stated that one way to begin a clustering investigation is to define a distance function and to compute the matrix of distances between all pairs of samples in a dataset. If distance is a good measure of similarity, then the distance between samples in the same cluster will be significantly less than the distance between samples in different clusters. However, as stated on page 215 of Duda 1973, clustering does not require the use of a distance metric. For example, a nonmetric similarity function s(x, x') can be used to compare two vectors x and x'. Conventionally, s(x, x') is a symmetric function whose value is large when x and x' are somehow "similar." An example of a nonmetric similarity function s(x, x') is provided on page 216 of Duda 1973.

Once a method for measuring "similarity" or "dissimilarity" between points in a dataset has been selected, clustering requires a criterion function that measures the clustering quality of any partition of the data. Partitions of the dataset that extremize the criterion function are used to cluster the data. See page 217 of Duda 1973. Criterion functions are discussed in Section 6.8 of Duda 1973.

More recently, Duda et al., *Pattern Classification*, Second edition, John Wiley & Sons, Inc. New York, which is hereby incorporated by reference, has been published. Pages 537-563 describe clustering in detail. More information on clustering techniques can be found in Kaufman and Rousseeuw, 1990, *Finding Groups in Data: An Introduction to Cluster Analysis*, Wiley, New York, N.Y.; Everitt, 1993, Cluster analysis (Third Edition), Wiley, New York, N.Y.; and Backer, 1995, *Computer Assisted Reasoning in Cluster Analysis*, Prentice Hall, Upper Saddle River, N.J. Referring to blocks 210-212, particular exemplary clustering techniques that can be used in the systems and methods of the present disclosure to cluster a plurality of vectors, where each respective vector in the plurality of vectors comprises the discrete attribute values 124 across the first entities 122 of a corresponding second entity 126 (or principal components derived therefrom) includes, but is not limited to, hierarchical clustering (agglomerative clustering using nearest-neighbor algorithm, farthest-neighbor algorithm, the average linkage algorithm, the centroid algorithm, or the sum-of-squares algorithm), k-means clustering, fuzzy k-means clustering algorithm, and Jarvis-Patrick clustering.

Thus, in some embodiments, the clustering module 152 clusters the discrete attribute value dataset 120 using the discrete attribute value 124 for each first entity 122 in the plurality of first entities for each respective second entity 126 in the plurality of second entities, or principal component values 164 derived from the discrete attribute values 124, thereby assigning each respective second entity 126 in the plurality of second entities to a corresponding cluster 158 in a plurality of clusters and thereby assigning a cluster attribute value to each respective second entity in the plurality of second entities.

Referring to block 214, in one embodiment of the present disclosure k-means clustering is used. The goal of k-means clustering is to cluster the discrete attribute value dataset 120 based upon the principal components or the discrete attribute values of individual second entities into K partitions. Referring to block 214, in some embodiments, K is a number between 2 and 50 inclusive. In some embodiments, the number K is set to a predetermined number such as 10. In some embodiments, the number K is optimized for a particular discrete attribute value dataset 120. Referring to block 216, in some embodiments, a user sets the number K using the cell browser 150.

FIG. 4 illustrates an instance in which the AML Tutorial dataset 120, constituting mRNA data from 8,390 different cells, has been clustered into ten clusters 158. In some embodiments, for k-means clustering, the user selects in advance how many clusters the clustering algorithm will compute prior to clustering. K-means clustering of the present disclosure is then initialized with K cluster centers $\mu_1, \ldots, \mu_K$ randomly initialized in two dimensional space. As discussed above, for each respective second entity 126 i in the dataset, a vector $X_i$ is constructed of each principal component value 164 associated with the respective second entity 126. In the case where K is equal to 10, ten such vectors $\vec{X}$ are selected to be the centers of the ten clusters. Then, each remaining vector $\vec{X}_i$, corresponding to the second entities 126 which were not selected to be cluster centers, is assigned to its closest cluster center:

$$C_k = \left\{ n: k = \arg\min_k \left\| \vec{X}_i - \mu_k \right\|^2 \right\}$$

where $C_k$ is the set of examples closest to $\mu_k$ using the objective function:

$$J(\mu, r) = \Sigma_{n=1}^N \Sigma_{k=1}^K r_{nk} \| \vec{X}_i - \mu_k \|^2$$

where $\mu_1, \ldots, \mu_K$ are the K cluster centers and $r_{nk} \in \{0, 1\}$ is an indicator denoting whether a second entity 126 $\vec{X}_i$ belongs to a cluster k. Then, new cluster centers $\mu_k$ are recomputed (mean/centroid of the set $C_k$):

$$\mu_k = \frac{1}{|C_k|} \sum_{n \in C_k} \vec{X}_i$$

Then, all vectors $\vec{X}_i$, corresponding to the second entities 126 are assigned to the closest updated cluster centers as before. This is repeated while not converged. Any one of a number of convergence criteria can be used. One possible convergence criteria is that the cluster centers do not change when recomputed. The k-means clustering computes a score for each respective second entity 126 that takes into account the distance between the respective second entity and the centroid of the cluster 158 that the respective second entity has been assigned. In some embodiments this score is stored as the cluster attribute value 160 for the second entity 126.

Once the clusters are identified, as illustrated in FIG. 4, individual clusters can be selected to display. For instance, referring to FIG. 4, toggles 440 can be individually selected or deselected to display or remove from the display the corresponding cluster 158.

As illustrated in FIG. 4, in accordance with the systems and methods of the present disclosure, in typical embodiments each respective cluster 158 in the plurality of clusters consists of a unique different subset of the second plurality of entities 126. Moreover, because in typical embodiments the discrete attribute value dataset 120 is too large to load into the non-persistent memory 111, in typical embodiments this clustering loads less than the entirety of the discrete attribute value dataset 120 into the non-persistent memory 111 at any given time during the clustering. For instance, in embodiments where the discrete attribute value dataset 120 has been compressed using bgzf, only a subset of the blocks of the discrete attribute value dataset 120 are loaded into non-persistent memory during the clustering of the discrete attribute value dataset 120. Once one subset of the blocks of the discrete attribute value dataset 120 have been loaded from persistent memory 112 into non-persistent memory 111 and processed in accordance with the clustering algorithm (e.g., k-means clustering), the subset of blocks of data is discarded from non-persistent memory 111 and a different subset of blocks of the discrete attribute value dataset 120 are loaded from persistent memory 112 into non-persistent memory 111 and processed in accordance with the clustering algorithm of the clustering module 152.

In some embodiments k-means clustering is used to assign second entities 126 to clusters 158. In some such embodiments the k-means clustering uses as input the principal component values 164 for each second entity 126 as the basis for clustering the second entities into cluster. Thus, the k-means algorithm computes like clusters of second entities from the higher dimensional data (the set of principal component values) and then after some resolution, the k-means clustering tries to minimize error. In this way, the k-means clustering provides cluster assignments 158, which are recorded in the discrete attribute value dataset 120. In some embodiments, with k-means clustering, the user decides in advance how many clusters 158 there will be. In some embodiments, feature of k-means cluster is exploited by running a series of k-means clustering runs, with each different run having a different number of clusters (a different value for K). Thus, in some embodiments, a separate k-means clustering is performed on the principal component data values 164 of each second entity 122, ranging from two clusters to ten clusters, with each k-means clustering identifying a separability score (quality score) and all the results of each clustering embedded in the discrete attribute value dataset 120 from K=2 through K=10. In some such embodiments, such clustering is performed for K=2 through K=25. In some such embodiments, such clustering is performed for K=2 through K=100. The clustering that is displayed by default in such embodiments is the k-means clustering (1, N) that has the highest separability score. In FIG. 4, each cluster 158 is displayed in a different color. In other embodiments, each cluster 158 is displayed with a different dot pattern or hash pattern.

The k-means clustering algorithm is an attempt to elucidate like clusters 158 within the data. There is no guarantee that the clusters 158 represent physiologically significant events. In other words, a priori, it is not known what the clusters 158 mean. What is known is that the algorithm has determined that there are differences between the second entities 126 that are being represented by different colors or different hash patterns or symbols. The systems and methods of the present disclosure provide tools for determining whether there is any meaning behind the differences between the clusters such as the heat map of panel 404.

Referring to block 214, in some embodiments of the present disclosure, rather than using k-means clustering, a Louvain modularity algorithm is used. See, Blondel et al., Jul. 25, 2008, "Fast unfolding of communities in large networks," arXiv:0803.0476v2 [physical.coc-ph], which is hereby incorporated by reference. In some embodiments, the user can choose a clustering algorithm. In some embodiments, the user can choose between at least K-means clustering and a Louvain modularity algorithm. In some embodiments, the clustering the dataset comprises application of a Louvain modularity algorithm to a map, the map comprising a plurality of nodes and a plurality of edges. Each node in the plurality of nodes represents a second entity in the plurality of second entities. The coordinates in N-dimensional space of a respective node in the plurality of nodes are a set of principal components of the corresponding second entity in the plurality of second entities. The set of principal components is derived from the corresponding discrete attribute values of the plurality of first entities for the corresponding second entity, where N is the number of principal components in each set of principal components. An edge exists in the plurality of edges between a first node and a second node in the plurality of nodes when the first node is among the k nearest neighboring nodes of the second node in the first plurality of node, where the k nearest neighboring nodes to the second node is determined by computing a distance in the N-dimensional space between each node in the plurality of nodes, other than the second node, and the second node. In some embodiments, the distance is a Euclidean distance. In other embodiments, other distance metrics are used (e.g., Chebyshev distance, Mahalanobis distance, Manhattan distance, etc.). In typical embodiments, the nodes and the edges are not weighted for the Louvain modularity algorithm. In other words, each node and each edge receives the same weight in such embodiments Block 218—Computing differential attribute values for first entities in each cluster. Once each second entity 126 has been assigned to a respective cluster 158, the systems and methods of the present disclosure are able to compute, for each respective first entity 122 in the plurality of first entities for each respective cluster 158 in the plurality of clusters, a difference in the discrete attribute value 124 for the respective first entity 122 across the respective subset of second entities 126 in the respective cluster 158 relative to the discrete attribute value 124 for the respective first entity 122 across the plurality of clusters 158 other than the respective cluster, thereby deriving a differential value 162 for each respective first entity 122 in the plurality of first entities for each cluster 158 in the plurality of clusters. For instance, in some such embodiments, a differential expression algorithm is invoked to find the top expressing genes that are different between cell classes or other forms of cell labels. This is a form of the general differential expressional problem in which there is one set of expression data and another set of expression data and the question to be addressed is determining which genes are differentially expressed between the datasets.

In some embodiments differential expression is computed as the $\log_2$ fold change in (i) the average number of transcripts (discrete attribute value 124 for first entity 122) measured in each of the cells (second entities 126) of the subject cluster 158 that map to a particular gene (first entity 122) and (ii) the average number of transcripts measured in each of the cells of all clusters other than the subject cluster that map to the particular gene. Thus, consider the case in which the subject cluster contains 50 cells and on average each of the 50 cells contain 100 transcripts for gene A. The remaining clusters collectively contain 250 cells and on average each of the 250 cells contain 50 transcripts for gene A. Here, the fold change in expression for gene A is 100/50 and the $\log_2$ fold change is $\log_2(100/50)=1$. In FIG. 4, lower panel, the $\log_2$ fold change is computed in this manner for each gene in the human genome.

Figure 2B:
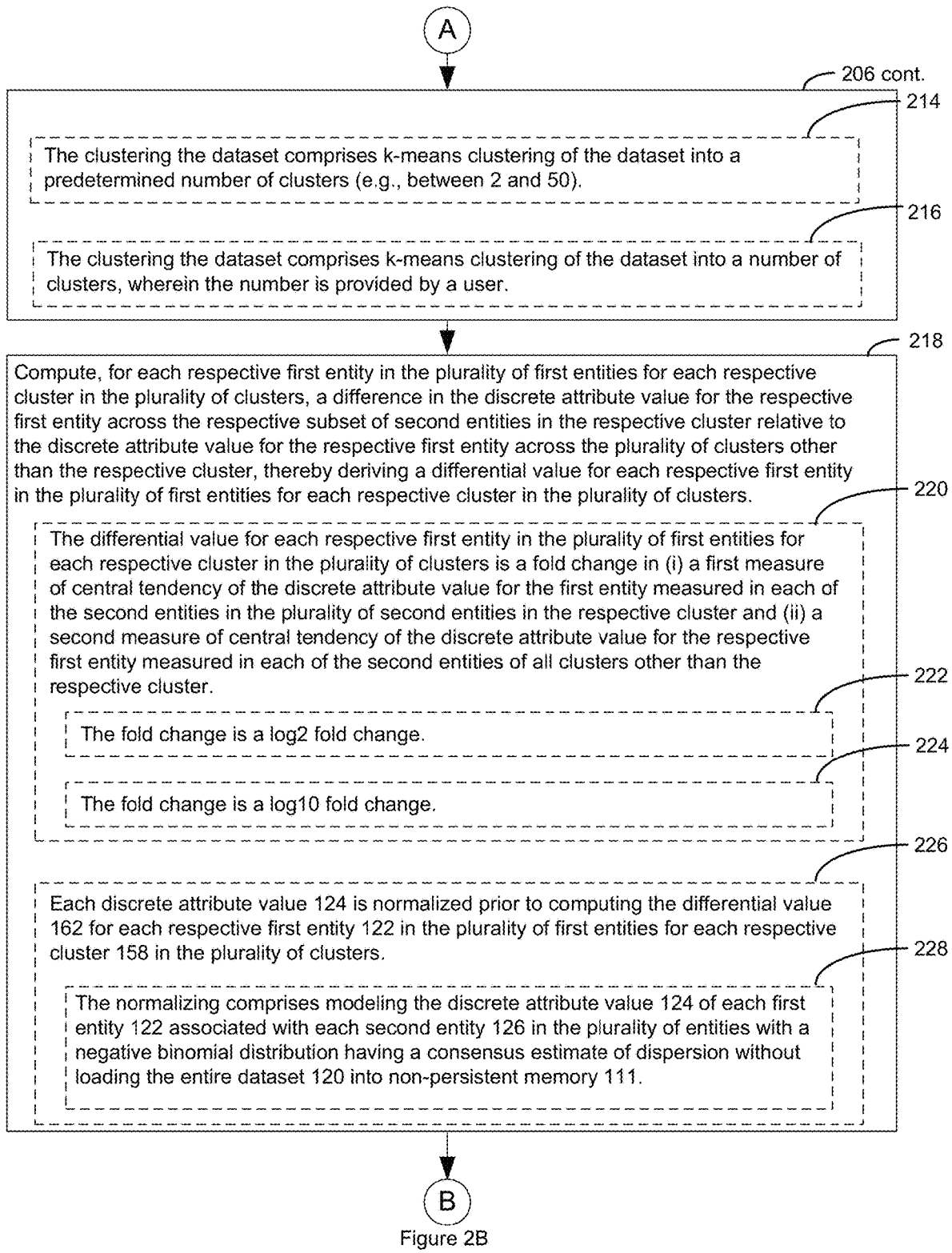

Referring to block 220 of FIG. 2B, in some embodiments, the differential value 162 for each respective first entity 122 in the plurality of first entities for each respective cluster 158 in the plurality of clusters is a fold change in (i) a first measure of central tendency of the discrete attribute value 124 for the first entity measured in each of the second entities 126 in the plurality of second entities in the respective cluster 158 and (ii) a second measure of central tendency of the discrete attribute value 124 for the respective first entity 122 measured in each of the second entities 126 of all clusters 158 other than the respective cluster. In some embodiments, the first measure of central tendency is an arithmetic mean, weighted mean, midrange, midhinge, trimean, Winsorized mean, median, or mode of all the discrete attribute value 124 for the first entity measured in each of the second entities 126 in the plurality of second entities in the respective cluster 158. In some embodiments, the second measure of central tendency is an arithmetic mean, weighted mean, midrange, midhinge, trimean, Winsorized mean, median, or mode of all the discrete attribute value 124 for the first entity 122 measured in each of the second entities 126 in the plurality of second entities 126 in all clusters other than the respective cluster. Referring to block 222, in some embodiments the fold change is a $\log_2$ fold change. Referring to block 224, in some embodiments the fold change is a $\log_{10}$ fold change.

Given that measurement of discrete attribute values 124 for first entities 122 (e.g., count of mRNA that maps to a given gene in a given cell) is typically noisy, the variance of the discrete attribute values 124 for first entities 122 in each second entity 126 (e.g., count of mRNA that maps to given gene in a given cell) in a given cluster 158 of such second entities 126 is taken into account in some embodiments. This is analogous to the t-test which is a statistical way to measure the difference between two samples. Here, in some embodiments, statistical methods that take into account that a discrete number of first entities 122 are being measured (as the discrete attribute values 124 for a given first entity 122) for each second entity 126 and that model the variance that is inherent in the system from which the measurements are made are implemented.

Thus, referring to block 226 of FIG. 2B, in some embodiments, each discrete attribute value 124 is normalized prior to computing the differential value 162 for each respective first entity 122 in the plurality of first entities for each respective cluster 158 in the plurality of clusters. Referring to block 228 of FIG. 2B, in some embodiments, the normalizing comprises modeling the discrete attribute value 124 of each first entity associated with each second entity in the plurality of entities with a negative binomial distribution having a consensus estimate of dispersion without loading the entire dataset into non-persistent memory 111. Such embodiments are useful, for example, for RNA-seq experiments that produce discrete attribute values 124 for first entities 122 (e.g., digital counts of mRNA reads that are affected by both biological and technical variation). To distinguish the systematic changes in expression between conditions from noise, the counts are frequently modeled by the Negative Binomial distribution. See Yu, 2013, "Shrinkage estimation of dispersion in Negative Binomial models for RNA-seq experiments with small sample size," Bioinformatics 29, pp. 1275-1282, which is hereby incoporated by reference.

The negative binomial distribution for a discrete attribute value 124 for a given first entity 122 includes a dispersion parameter for the discrete attribute value 124 which tracks the extent to which the variance in the discrete attribute value 124 exceeds an expected value. See Yu, 2013, "Shrinkage estimation of dispersion in Negative Binomial models for RNA-seq experiments with small sample size," Bioinformatics 29, pp. 1275-1282, and Cameron and Trivedi, 1998, "Regression Analysis of Count Data," Econometric Society Monograph 30, Cambridge University Press, Cambridge, UK, each of which is hereby incorporated by reference. Rather than relying upon an independent dispersion parameter for the discrete attribute value 124 of each first entity 122, some embodiments of the disclosed systems and methods advantageously use a consensus estimate across the discrete attribute values 124 of all the first entities 122. This is termed herein the "consensus estimate of dispersion." The consensus estimate of dispersion is advantageous for RNA-seq experiments in which whole transcriptome shotgun sequencing (RNA-seq) technology quantifies gene expression in biological samples in counts of transcript reads mapped to the genes, which is one form of experiment used to acquire the disclosed dicreate atribute values 124 in some embodiments, thereby concurrently quantifying the expression of many genes. The genes share aspects of biological and technical variation, and therefore a combination of the gene-specific estimates and of consensus estimates can yield better estimates of variation. See Yu, 2013, "Shrinkage estimation of dispersion in Negative Binomial models for RNA-seq experiments with small sample size," Bioinformatics 29, pp. 1275-1282 and Anders and Huber, 2010, "Differential expression analysis for sequence count data," Genome Biol 11, R106, each of which are hereby incorporated by reference. For instance, in some such embodiments, sSeq is applied to the discrete attribute value 124 of each first entity 122. sSeq is disclosed in Yu, 2013, "Shrinkage estimation of dispersion in Negative Binomial models for RNA-seq experiments with small sample size," Bioinformatics 29, pp. 1275-1282, which is hereby incorporated by reference. sSeq scales very well with the number of genes that are being compared. In typical experiments in accordance with the present disclosure, each cluster 158 may include hundreds, thousands, tens of thousands, hundreds of thousands, or more second entities 126, and each respective second entity 126 may contain mRNA expression data for hundreds, or thousands of different genes. As such sSeq is particularly advantageous when testing for differential expression in such large discrete attribute value datasets 120. Of all the RNA-seq methods, sSeq is advantageously faster. Other single-cell differential expression methods exist and can be used in some embodiments, but they are designed for smaller-scale experiments. As such sSeq, and more generally techniques that normalize discrete attribute values by modeling the discrete attribute value 124 of each first entity 122 associated with each second entity 126 in the plurality of entities with a negative binomial distribution having a consensus estimate of dispersion without loading the entire discrete attribute value dataset 120 into non-persistent memory 111, are practiced in some embodiments of the present disclosure. In some embodiments, in the case where parameters for the sSeq calculations are calculated, the discrete attribute values for each of the first entities is examined in order to get a dispersion value for all the first entities. Here, although all the discrete attribute values for the first entities are accessed to make the calculation, the discrete attribute values are not all read from persistent memory 112 at the same time. In some embodiments, discrete attribute values are obtained by traversing through blocks of compressed data, a few blocks at a time. That is, a set of blocks, consisting of the few compressed blocks, in the dataset are loaded into non-persistent memory from persistent memory and are analyzed to determine which first entities the set of blocks represent. An array of discrete attribute values across the plurality of second entities, for each of the first entities encoded in the set of blocks, is determined and used calculate the variance, or other needed parameters, for these first entities across the plurality of second entities. This process is repeated in which new set of blocks is loaded into non-persistent memory from persistent memory, analyzed to determine which first entities are encoded in the new set of blocks, and then used to compute the variance, or other needed parameters, for these first entities across the plurality of second entities for each of the first entities encoded in the new set of blocks, before discarding the set of blocks from non-persistent memory. In this way, only a limited amount of the discrete attribute value dataset 120 is stored in non-persistent memory 111 at any given time (e.g., the data for a particular block that contain the discrete attribute values for a particular first entity). Further, the systems and methods of the present disclosure are able to compute variance in discrete attribute values for a given first entity because it has got all the discrete attribute values for that particular first entity across the entire discrete attribute value dataset 120 stored in a single bgzf block, in some embodiments. Once the variance, or other needed parameter is computed for the first entities (or discrete attribute values of the first entities), the accessed set of bgzf blocks (which is a subset of the total number of bgzf blocks in the dataset), which had been loaded into non-persistent memory 111 to perform the computation, is dropped from non-persistent memory and another set of bgzf blocks for which such computations is to be performed is loaded into the non-persistent memory 111 from the persistent memory 112. In some embodiments, such processes run in parallel (e.g., one process for each first entity) when there are multiple processing cores 102. That is, each processing core concurrently analyzes a different respective set of blocks in the dataset and computes first entities statistics for those first entities represented in the respective set of blocks.

Following such normalization, in some embodiments, for each respective first entity 122, an average (or some other measure of central tendency) discrete attribute value 124 (e.g., count of the first entity 122) for each first entity 122 is calculated for each cluster 158 of second entities 126. Thus, in the case where there is a first and second cluster 158 of second entities 126, the average (or some other measure of central tendency) discrete attribute value 124 of the first entity A across all the second entities 126 of the first cluster 158, and the average (or some other measure of central tendency) discrete attribute value 124 of first entity A across all the second entities 126 of the second cluster 158 is calculated and, from this, the differential value 162 for each the first entity with respect to the first cluster is calculated. This is repeated for each of the first entities 122 in a given cluster. It is further repeated for each cluster 158 in the plurality of clusters. In some embodiments, there are other factors that are considered, like adjusting the initial estimate of the variance in the discrete attribute value 124 when the data proves to be noisy. In the case where there are more than two clusters, the average (or some other measure of central tendency) discrete attribute value 124 of the first entity A across all the second entities 126 of the first cluster 158 and the average (or some other measure of central tendency) discrete attribute value 124 of first entity A across all the second entities 126 of the remaining cluster 158, is calculated and used to compute the differential value 162.

Block 230—Display a heat map. With reference to FIG. 4, once the differential value 162 for each respective first entity 122 in the plurality of first entities for each respective cluster 158 in the plurality of clusters has been computed, a heat map 402 of these differential values is displayed in a first panel 404 of an interface 400. The heat map 402 comprises a representation of the differential value 162 for each respective first entity 122 in the plurality of first entities for each cluster 158 in the plurality of clusters. As illustrated in FIG. 4, the differential value 162 for each first entity 122 in the plurality of entities (e.g., first entities from 122-1 to 122-M) for each cluster 158 (e.g., clusters 158-1, 158-3, 158-7, and 158-9) is illustrated in a color coded way to represent the $\log_2$ fold change in accordance with color key 408. In accordance with color key 408, those first entities 122 that are upregulated in the second entities 126 of a particular cluster 158 relative to all other clusters are assigned more positive values, whereas those first entities 122 that are down-regulated in the second entities 126 of a particular cluster 158 relative to all other clusters are assigned more negative values. In some embodiments, the heat map can be exported to persistent storage (e.g., as a PNG graphic, JPG graphic, or other file formats).

Block—232 plot a two dimensional plot of the second entities in the dataset. With reference to FIG. 4, in some embodiments, a two-dimensional visualization of the discrete attribute value dataset 120 is also provided in a second panel 420. In some embodiments, the two-dimensional visualization in the second panel 420 is computed by a back end pipeline that is remote from visualization system 100 and is stored as two-dimensional datapoints 166 in the discrete attribute value dataset 120 as illustrated in FIG. 1B. In some embodiments, the two-dimensional visualization 420 is computed by the visualization system.

Because the initial data is sparse, in some embodiments, the two-dimensional visualization is prepared by computing a plurality of principal component values 164 for each respective second entity 126 in the plurality of second entities based upon respective values of the discrete attribute value 124 for each first entity 122 in the respective second entity 126. In some embodiments, the plurality of principal component values is ten. In some embodiments, the plurality of principal component values is between 5 and 100. In some embodiments, the plurality of principal component values is between 5 and 50. In some embodiments, the plurality of principal component values is between 8 and 35. Then, a dimension reduction technique is applied to the plurality of principal components values for each respective second entity 126 in the plurality of second entities thereby determining a two-dimensional data point 166 for each second entity 126 in the plurality of entities. Each respective second entity 126 in the plurality of entities is then plotted in the second panel based upon the two-dimensional data point for the respective second entity.

For instance, one embodiment of the present disclosure provides a back end pipeline that is performed on a computer system other than the visualization system 100. The back end pipeline comprises a two stage data reduction. In the first stage, the discrete attribute values 124 (e.g. mRNA expression data) for each first entity 122 in a single second entity 126 (e.g., a single cell) is treated as a high-dimensional data point. For instance, a one dimensional vector that includes a dimension for each of the 19,000-20,000 genes in the human genome, with each dimension populated with the measured mRNA expression level for the corresponding gene. More generally, a one dimensional vector that includes a dimension for each discrete attribute value 124 of the plurality of first entities, with each dimension populated with the discrete attribute value 124 for the corresponding first entity 122. This data is considered somewhat sparse and so principal component analysis is suitable for reducing the dimensionality of the data down to ten dimensions in this example. Thus, upon application of principal component analysis each cell now has computed values for ten principal components and thus the dimensionality of the data has been reduced from approximately 20,000 to ten. That is, principal component analysis is used to assign each respective cell principal components that describe the variation in the respective cell's mRNA expression levels with respect to expression levels of corresponding mRNA of other cells in the dataset. Next, the data reduction technique t-Distributed stochastic neighboring entities (t-SNE) is used to further reduce the dimensionality of the data from ten to two. See, block 236 of FIG. 2C. t-SNE is a machine learning algorithm for dimensionality reduction. See van der Maaten and Hinton, 2008, "Visualizing High-Dimensional Data Using t-SNE," Journal of Machine Learning Research 9, 2579-2605, which is hereby incorporated by reference. The non-linear dimensionality reduction technique t-SNE is particularly well-suited for embedding high-dimensional data (here, the ten principal components values 164) computed for each measured second entity based upon the measured discrete attribute value (e.g., expression level) of each first entity 122 (e.g., expressed mRNA) in a respective second entity (e.g., a respective cell) as determined by principal component analysis into a space of two, which can then be visualized as a two-dimensional visualization (e.g. the scatter plot of second panel 420). In some embodiments, t-SNE is used to model each high-dimensional object (the 10 principal components of each measured cell) as a two-dimensional point in such a way that similarly expressing second entities (e.g., cells) are modeled as nearby two-dimensional datapoints 166 and dissimilarly expressing cells are modeled as distant two-dimensional datapoints 166 in the two-dimensional plot. The t-SNE algorithm comprises two main stages. First, t-SNE constructs a probability distribution over pairs of high-dimensional second entity vectors in such a way that similar second entity vectors (second entities that have similar values for their ten principal components and thus presumably have similar discrete attribute values 124 across the plurality of first entities 122) have a high probability of being picked, while dissimilarly dissimilar second entity vectors (second entities that have dissimilar values for their ten principal components and thus presumably have dissimilar discrete attribute values 124 across the plurality of first entities 122) have a small probability of being picked. Second, t-SNE defines a similar probability distribution over the plurality of second entities 126 in the low-dimensional map, and it minimizes the Kullback—Leibler divergence between the two distributions with respect to the locations of the points in the map. In some embodiments the t-SNE algorithm uses the Euclidean distance between objects as the base of its similarity metric. In other embodiments, other distance metrics are used (e.g., Chebyshev distance, Mahalanobis distance, Manhattan distance, etc.).

Figure 2C:
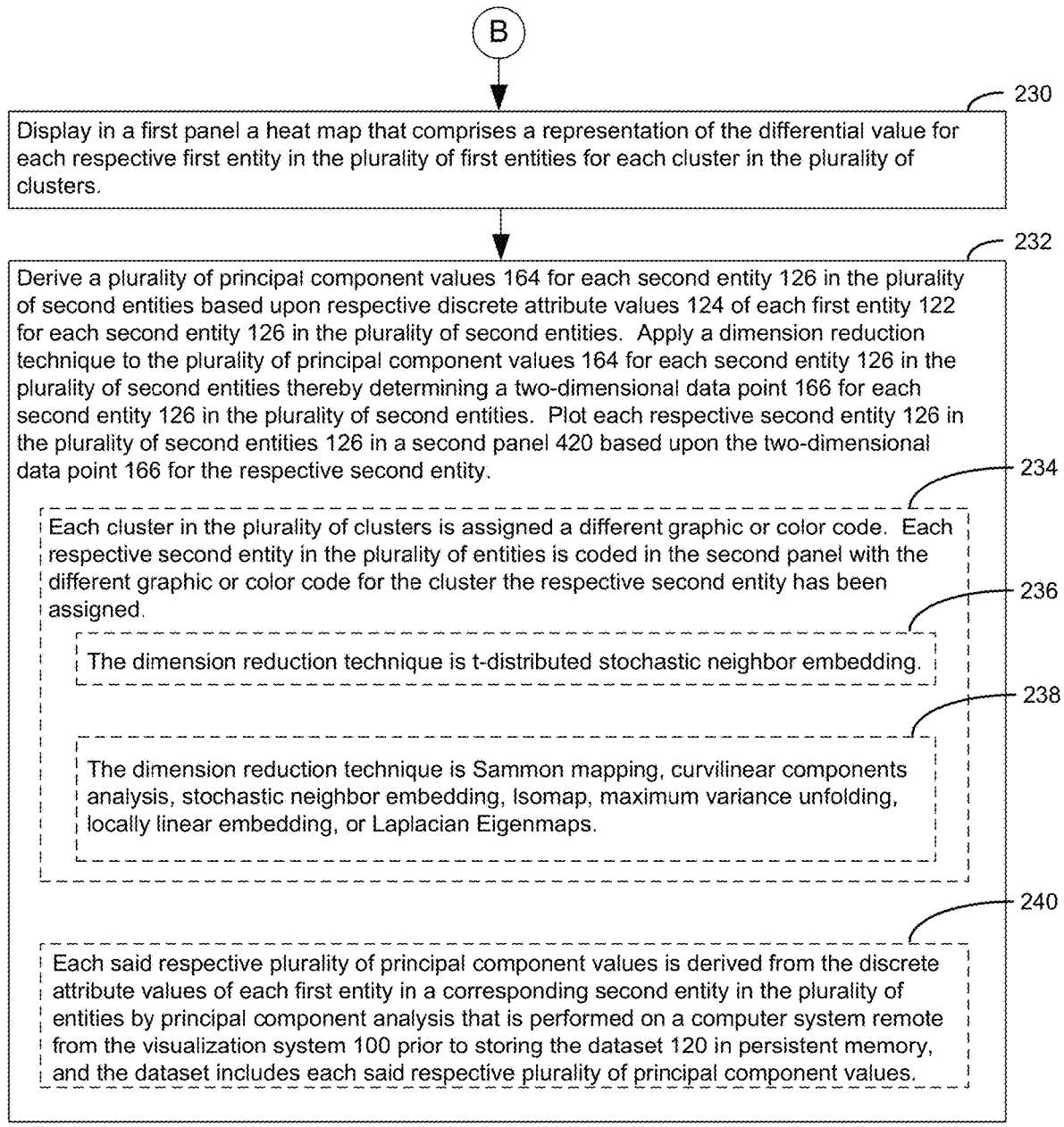

In some embodiments, referring to block 238 of FIG. 2C, rather than using t-SNE, the dimension reduction technique used to reduce the principal component values 164 to a two-dimensional datapoint 166 is Sammon mapping, curvilinear components analysis, stochastic neighbor embedding, Isomap, maximum variance unfolding, locally linear embedding, or Laplacian Eigenmaps. These techniques are described in van der Maaten and Hinton, 2008, "Visualizing High-Dimensional Data Using t-SNE," Journal of Machine Learning Research 9, 2579-2605, which is hereby incorporated by reference. In some embodiments, the user has the option to select the dimension reduction technique. In some embodiments, the user has the option to select the dimension reduction technique from a group comprising all or a subset of the group consisting of t-SNE, Sammon mapping, curvilinear components analysis, stochastic neighbor embedding, Isomap, maximum variance unfolding, locally linear embedding, and Laplacian Eigenmaps.

Referring to block 234 of FIG. 2C, and as illustrated in FIG. 4, in some embodiments each cluster 158 in the plurality of clusters is assigned a different graphic or color code. Further, each respective second entity 126 in the plurality of entities is coded in the second panel 420 with the different graphic or color code for the cluster 158 the respective second entity has been assigned.

Referring to block 240, in some embodiments, each of the respective plurality of principal component values is derived from the discrete attribute values of each first entity in a corresponding second entity in the plurality of entities by principal component analysis that is performed on a computer system remote from the visualization system 100 prior to storing the discrete attribute value dataset 120 in persistent memory, and the dataset includes each said respective plurality of principal component values.

Now that the overall functionality of the systems and methods of the present disclosure has been introduced, attention turns to additional features afforded by the present disclosure. As illustrated in FIG. 4, for each cluster 158 in the upper panel 420, there is a row in the lower panel 404 that illustrates the fold change (e.g. log 2 fold change) of the average discrete attribute value 124 for each respective first entity 122 across the second entities 126 of the cluster 158 represented by the row compared to the average discrete attribute value 124 of the respective first entity 122 in the remainder of the population of second entities represented by the discrete attribute value dataset 120.

The lower panel 404 has two settings. The first is a hierarchical clustering view of significant first entities 122 per cluster. The legend 408 on the right of the lower panel 404 indicates the $\log_2$ fold change compared to the average in the population. For instance, in one color coding scheme, red means higher abundance (higher discrete attribute values 124), blue means lower abundance (lower discrete attribute values 124), in a given cluster 158 as compared to the average abundance in the population. In FIG. 4, $\log_2$ fold change in expression refers to the $\log_2$ fold value of (i) the average number of transcripts (discrete attribute value) measured in each of the cells of the subject cluster that map to a particular gene (first entity 122) and (ii) the average number of transcripts measured in each of the cells of all clusters other than the subject cluster that map to the particular gene.

Figure 5:
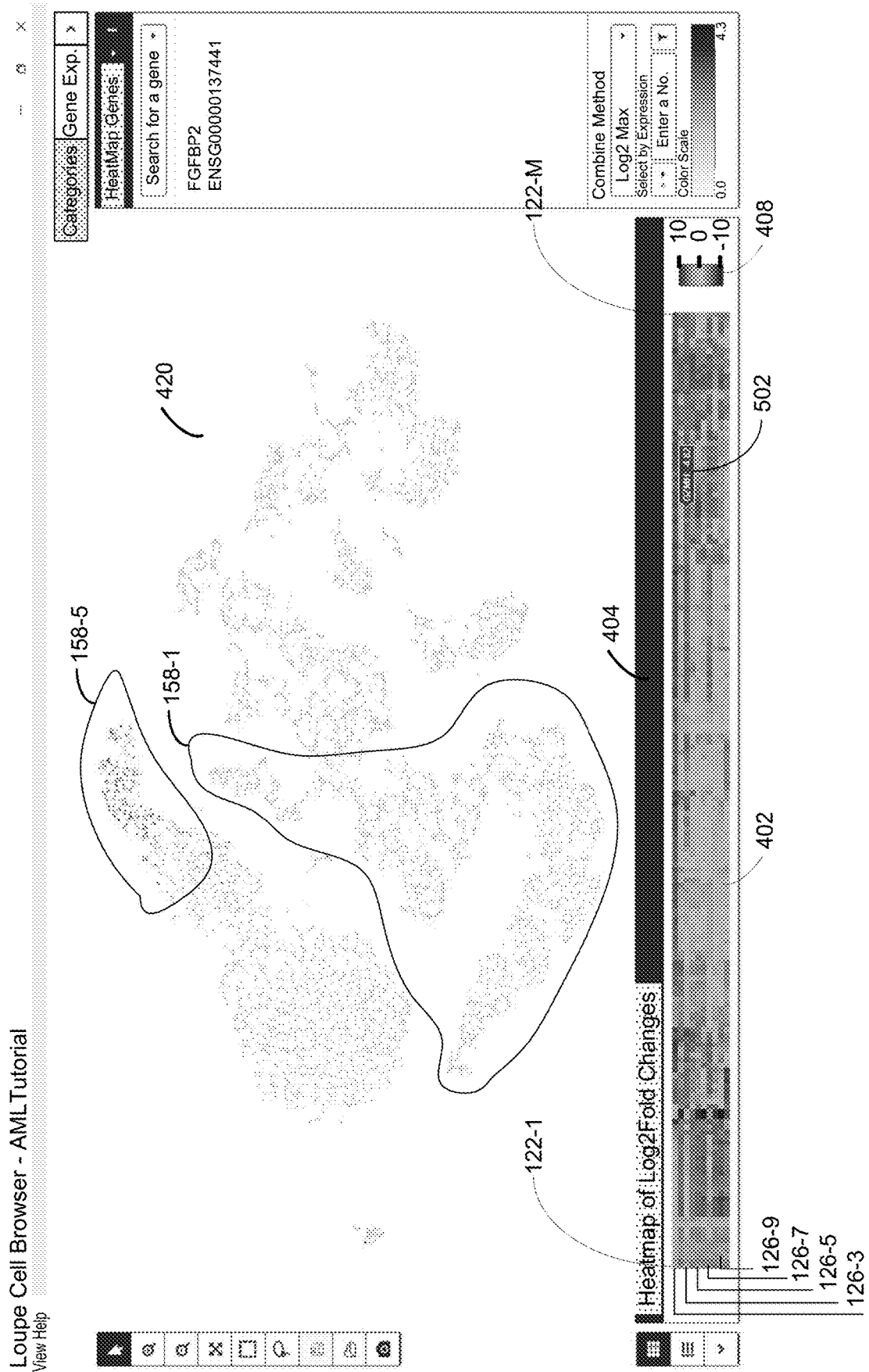
FIG. 5 illustrates the selection of a particular first entity and visualization of each respective second entity in the plurality of second entities based upon the differential value for the first entity associated with the respective second entity in accordance with some embodiments of the present disclosure.

Referring to FIG. 5, selection of a particular first entity 122 (e.g., selection of first entity 502) in the lower panel 404 causes each respective second entity 126 in the upper panel 420 to be colored on a color scale that represents the discrete attribute value 124 of that respective first entity 122 in each respective second entity 126 (e.g., second entities 126-1, 126-3, 126-5, 126-7, 126-9). So, for example, referring to FIG. 5, when a user clicks on the first entity 122 entitled GZMH 502 in the lower panel 404, which is highly expressed in k-means cluster 158-5, each respective second entity 126 in the upper panel 420 is colored to reflect the discrete attribute value 124 for GZMH in the respective second entity 126. From FIG. 5, upper panel, it is seen that high expression of GZMH is limited to k-means cluster group 158-5, consistent with the heatmap in the lower panel 404 of FIG. 5. In other words, FIG. 5 provides in the top panel 420 the discrete attribute value 124 (e.g., mRNA counts) for the particular first entity 122 (e.g., gene) that has been identified in the lower panel of FIG. 5.

In some embodiments, the user can select more than one first entity 122 (e.g. mRNA) in the lower panel 404 of FIG. 5 and thereby cause the upper panel to concurrently illustrate the discrete attribute value 124 of each of the more than one first entity 122 in each respective second entity 126 in the discrete attribute value dataset 120 at the same time.

Figure 6:
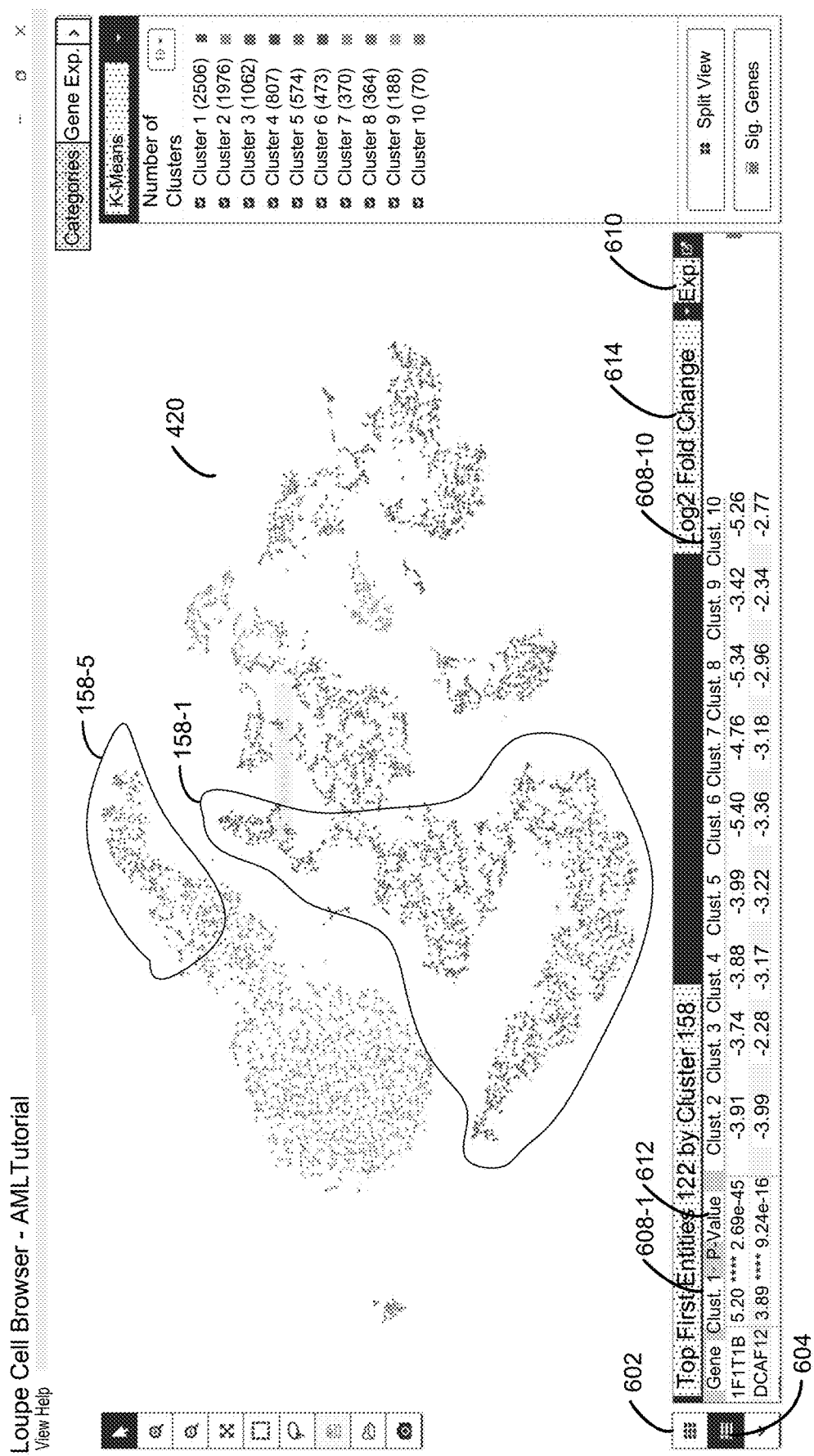
FIG. 6 illustrates an alternate view to the bottom panel of FIG. 5 in which a tabular representation of the $log_2$ discrete attribute values of the heat map of 5 is illustrated in column format in accordance with some embodiments of the present disclosure.
Figure 7:
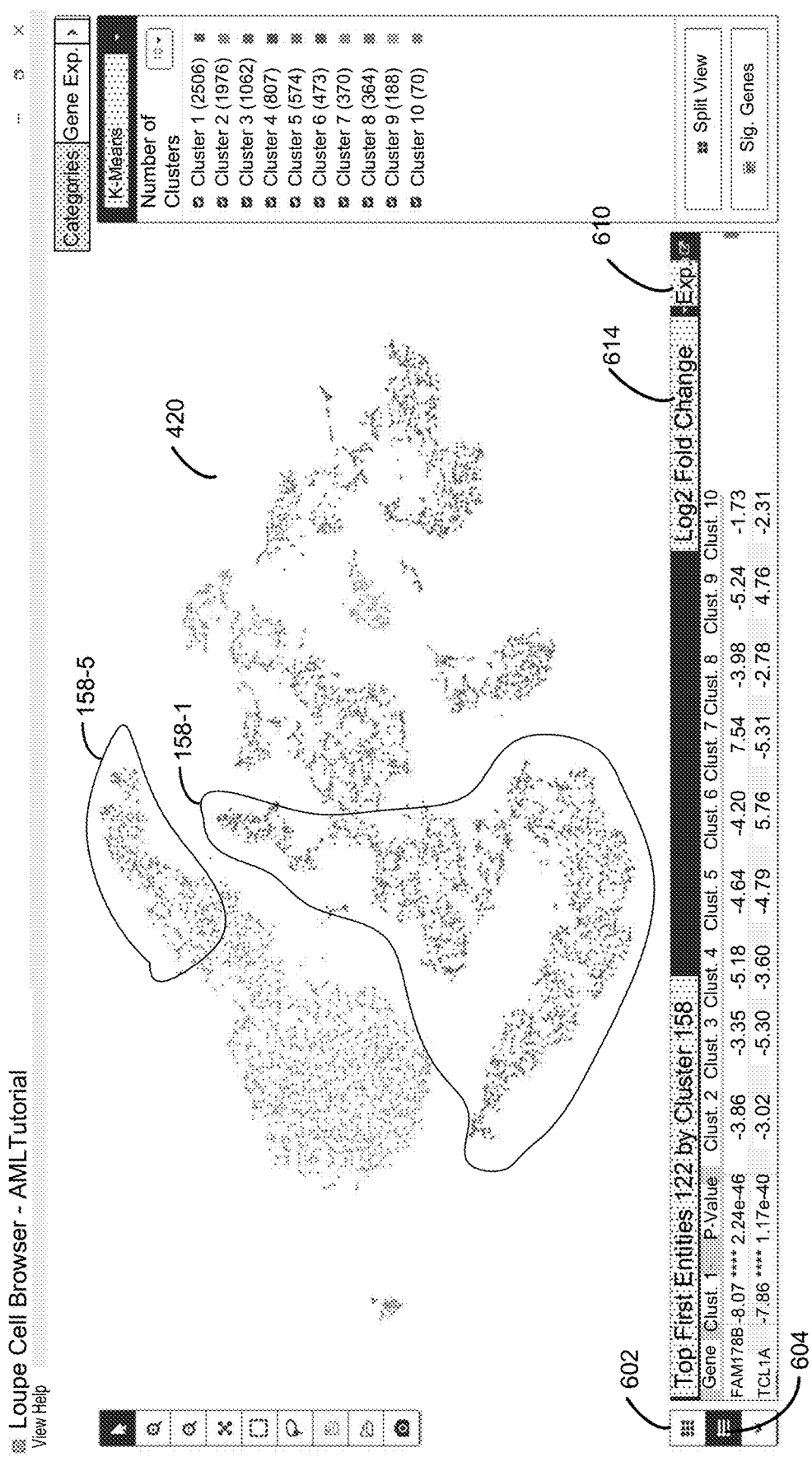
FIG. 7 illustrates inversion of the ranking of the entire table of FIG. 6 by clicking a second time on a selected column label so that the first entity associated with the least significant discrete attribute value (e.g., least expressed) is at the top of the table of the lower panel of FIG. 7 in accordance with some embodiments of the present disclosure.
Figure 8:
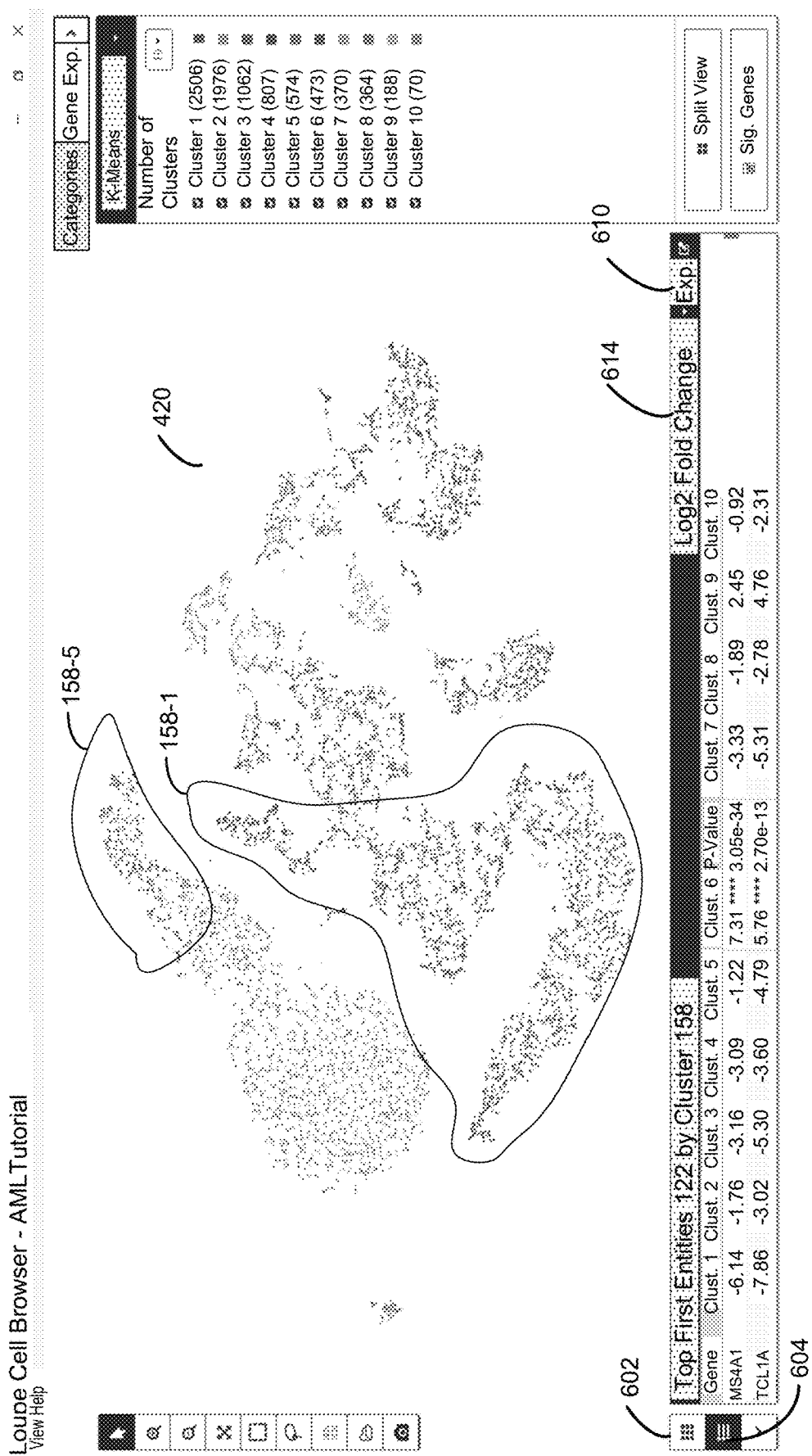
FIG. 8 illustrates selection of the label for a different cluster than that of FIG. 7 which causes the entire table in the lower panel of FIG. 8 to be re-ranked (relative to FIG. 7) based on the discrete attribute values of the first entities in the second entities that are in the newly selected k-means cluster in accordance with some embodiments of the present disclosure.
Figure 9:
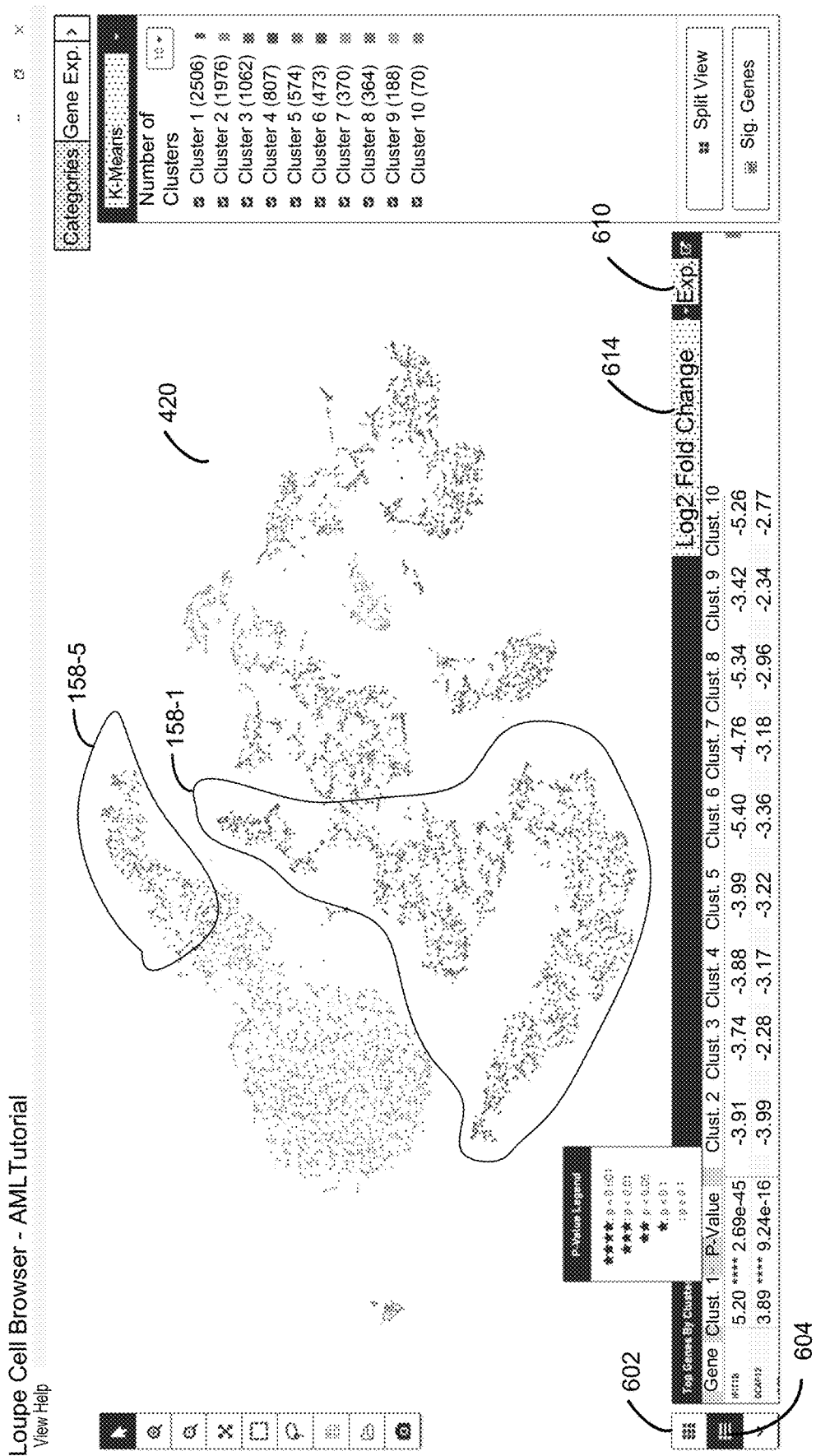
FIG. 9 illustrates how P-value are annotated with a star system, in which four stars means there is a significant difference between the selected cluster and the rest of the clusters for a given first entity, whereas fewer stars means that there is a less significant difference in discrete attribute value for the first entity the selected cluster relative to all the other clusters in accordance with some embodiments of the present disclosure.

Referring to FIG. 6, an alternate view to the bottom panel 404 of FIG. 5 is shown by clicking on icon 604 of tool bar 602. Upon selection of icon 604, a tabular representation 606 of the log₂ discrete attribute values 124 of the heat map 404 of FIG. 4 and is illustrated in column format, whereas the heat map 404 showed the log₂ discrete attribute values 124 in rows. The user can select any respective cluster 158 by selecting the column label 608 for the respective cluster (column labels for clusters 1 and 10 are marked as 608-1 and 608-respectively). This will re-rank all the first entities 122 such that those first entities that are associated with the most significant discrete attribute value 124 in the selected cluster 158 are ranked first (e.g. in the order of the most first entities have the most significant associated discrete attribute value 124). Moreover, a p-value 612 is provided for the discrete attribute value of each first entity 122 in the selected cluster to provide the statistical significance of the discrete attribute value 124 in the selected cluster 158 relative to the discrete attribute value 124 of the same first entity 122 in all the other clusters 158. In some embodiments, these p-values are calculated based upon the absolute discrete attribute values 124, not the log₂ values used for visualization in the heat map 402. Referring to FIG. 6 to illustrate, the first entity 122 in cluster 1 that has the largest associated discrete attribute value 124, IFIT1B, has a p-value of $2.69e^{-45}$. As illustrated in FIGS. 6 through 12, and FIG. 9 in particular, this p-value is annotated with a star system, in which four stars means there is a significant difference between the selected cluster (k-means cluster 158-1 in FIG. 6) and the rest of the clusters for a given first entity, whereas fewer stars means that there is a less significant difference in the discrete attribute value 124 (e.g., difference in expression) between the first entity 122 in the selected cluster relative to all the other clusters. By clicking a second time on the selected column label 608, the ranking of the entire table is inverted so that the first entity 122 associated with the least significant discrete attribute value 124 (e.g., least expressed) is at the top of the table, as illustrated in FIG. 7. FIG. 8 illustrates selection of the label for cluster 158-6, which causes the entire table to re-ranked based on the discrete attribute values 124 of the first entities 122 in the second entities 126 that are in k-means cluster 6. In this way, the sorting is performed to more easily allow for the quantitative inspection of the difference in discrete attribute value 158 in any one cluster 158 relative to the rest of the clusters. As illustrated by tab 610, the table of values can be exported, e.g. to an EXCEL csv file, by pressing tab 610 at which point the user is prompted to save the table as a csv (or other file format). In this way, once the user has completed their exploration of the k-means clustering, tab 610 allows the user to export the values. Moreover, in some embodiments a user is able to load and save lists of first entities to and from persistent storage, for instance, using panel 404. Moreover, in some embodiments a user is able to load and save lists of second entities to and from persistent storage, for instance, using panel 404. In each instance, the user can create such lists using the selection tools provided on the left side of the upper panel of FIG. 4 (e.g., the lasso selection tool, etc.).

Figure 10:
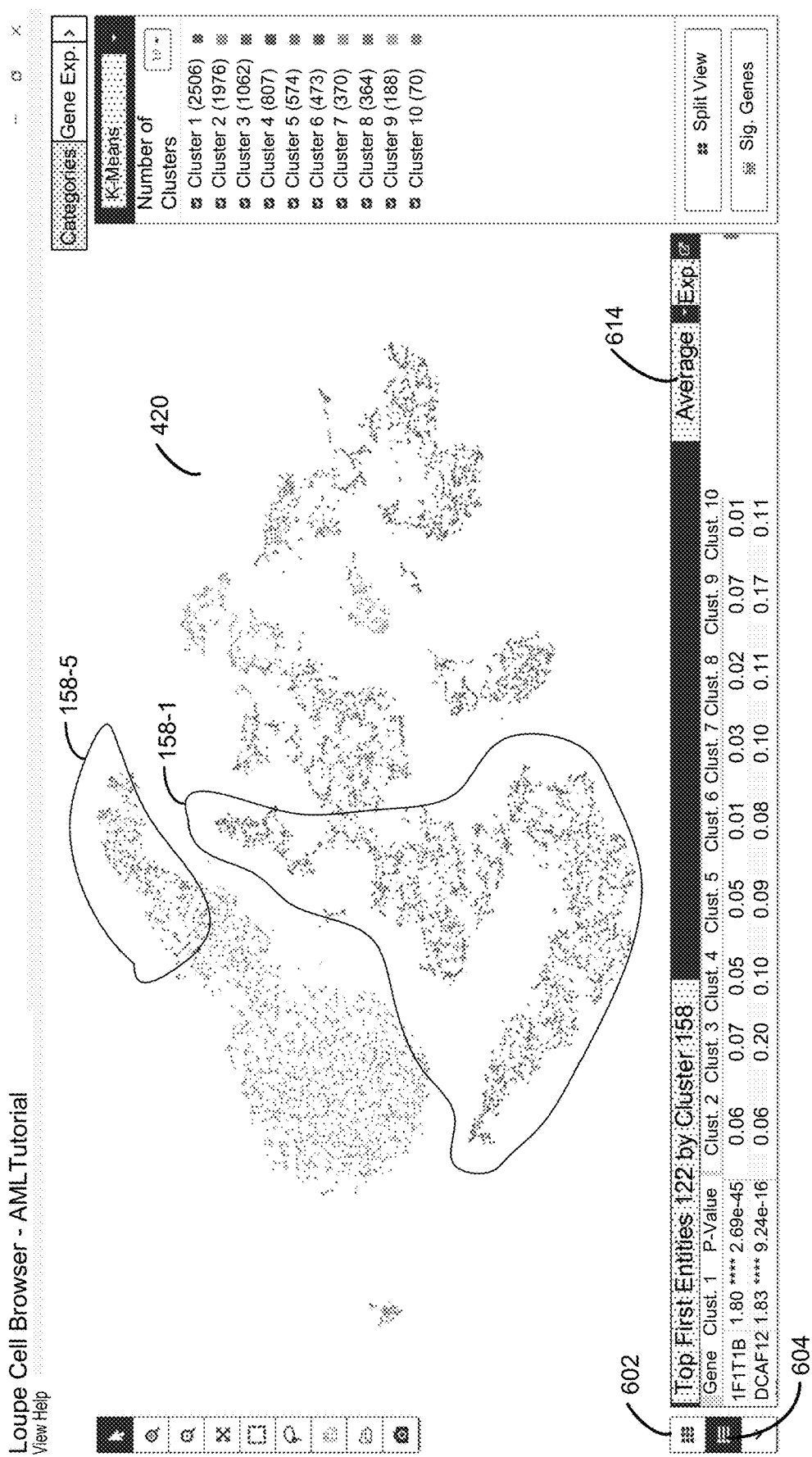
FIG. 10 illustrates how a user can use a toggle 604 to toggle between the fold change values for first entities of FIG. 9 and the average discrete attribute value per first entity per second entity in each cluster (e.g. the number of transcripts per gene for per cell) of FIG. 10 in accordance with some embodiments of the present disclosure.

Referring again to FIG. 4, the heatmap 402 provides a log₂ differential that is optimal in instances where the second entity 126 is a cell and the discrete attribute value 124 represents the number of transcripts that map to a given gene in the cell in order to provide a sufficient dynamic range over the number of transcripts seen per gene in the given cell. In some embodiments, log₁₀ differential expression is used instead. However, it is expected that log₁₀ does not provide sufficient dynamic range for appropriate visualization of the relative expression of gene data in the k-means clusters in some instances. This is because the distinction between zero and one count in the raw data is also fairly important. Because of this, it is not desirable to drown the difference between zero and one with the difference between nine and ten. The difference between zero and one in the discrete attribute value 124 differential (between one cluster and the other clusters) is a significant jump and so a log scale that is able to at least have that floor where "zero" is one color in the heat map 402 and "one" is something that is visually different from "zero." Hence the log₂ scale is used in the heat map 402 illustrated in the Figures. Referring to FIG. 10, toggle 614 permits the user to toggle between the fold change and the average discrete attribute value 124 per first entity 122 per second entity 126 in each cluster 158 (e.g. the number of transcripts per gene for per cell). Thus, in FIG. 10, for Gene 1F1T1B the average discrete attribute value 124 of the first entities 122 that map onto gene 1F1T1B in the second entities of cluster 158-1 is 1.80, the average discrete attribute value 124 of the first entities 122 that map onto gene 1F1T1B in the second entities of cluster 158-2 is 0.06, and so forth. In some embodiments, the average value is some other measure of central tendency of the discrete attribute value 124 such as an arithmetic mean, weighted mean, midrange, midhinge, trimean, Winsorized mean, median, or mode of all the discrete attribute values 124 for the first entity 122 measured in each of the second entities 126 in the plurality of second entities in the respective cluster 158. FIG. 10 provides a means for discerning between those first entities 122 (e.g., genes) that are associated with significant average discrete attribute values 124 (e.g., fairly high transcript counts) in all the k-means clusters 158 and those first entities 122 (e.g., genes) that are associated with appreciable discrete attribute values 124 that localized to only certain k-means clusters.

FIGS. 4 through 11 illustrate the analysis of data that comes out of a second entity analysis (e.g., single cell sequencing) pipeline. Another aspect of the present disclosure handles situations in which the pipeline consists of multiple classes 172 of second entities 126. That is, situations in which each such sample consists of first discrete attribute values 124 for each respective first entity 122 (e.g., mRNA that map to a particular gene in a plurality of genes) in each second entity 126 (e.g. cell) in a first plurality of second entities under a first condition (therefore representing a first class 172), second discrete attribute values 124 for each respective first entity 122 in each second entity in a second plurality of different second entities under a second condition (therefore representing a second class 172), and so forth. In other situations, each such sample consists of first discrete attribute values 124 for each respective first entity 122 (e.g., mRNA that map to a particular gene in a plurality of genes) in each second entity 126 (e.g. cell) in a first plurality of second entities of a first type (a first classes 172), second discrete attribute values 124 for each respective first entity 122 in each second entity in a second plurality of second entities of a second type (a second class 172), and so forth, where each such class 172 refers to a different cell type, a different disease state, a different tissue type, a different organ type, a different species, or different assay conditions or any of the forgoing. In some embodiments, the discrete attribute value dataset 120 contains data for second entities from two or more such classes, three or more such classes, four or more such classes, five or more such classes, ten or more such classes 172, or 100 or more such classes 172.

In some embodiments, there are a plurality of categories 170 and each second entity 126 is in each such category 170. In such embodiments, each category 170 has one or more sub-categories, termed classes 172, that can be individually selected. In some embodiments, all such data is preloaded into a single discrete attribute value dataset 120. Examples of categories, are illustrated in FIG. 11 and include k-means clustering (where K-means is the category 170 and each k-means cluster 158 is an example of a class 172), LibraryID (where LibraryID is the category 170 and which library a second entity originated from is the class 172), and AML-Status (where AML, status is the category 170, and which AML patient population a second entity originated from is the class 172).

Figure 11:
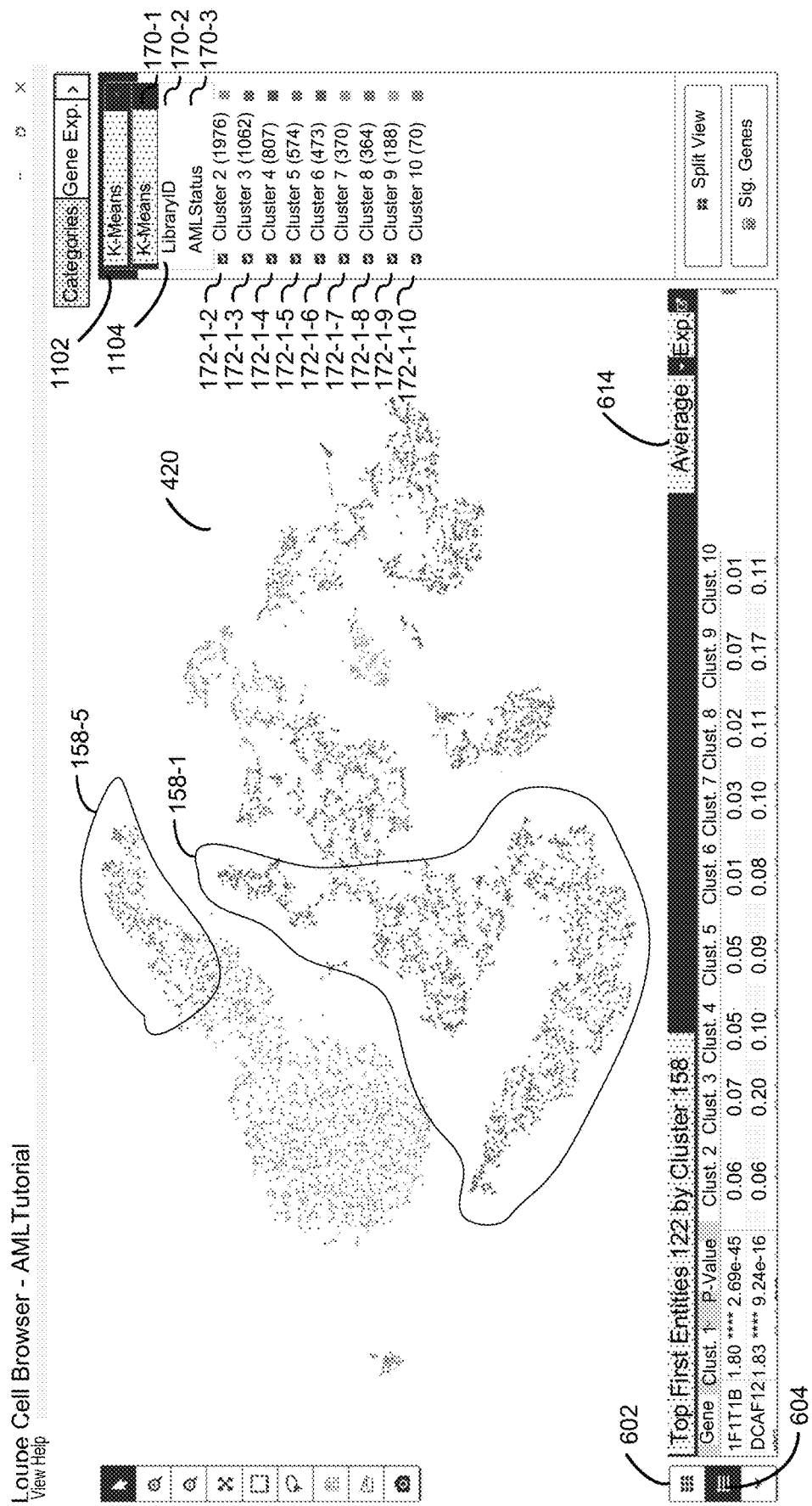
FIG. 11 illustrates how, by selecting affordance 1102, a dropdown menu 1104 is provided that shows all the different categories 170 that are associated with each second entity in a discrete attribute value dataset 120 in accordance with some embodiments of the present disclosure.

Turning to FIG. 11, by selecting affordance 1102, the dropdown menu 1104 is provided. The dropdown menu shows all the different categories 170 that are associated with each second entity in the discrete attribute value dataset 120. In the dataset illustrated in FIG. 11, there are three categories 170. The first such category is "k-means" 170-1, the selection of which will provide the view of FIG. 4, in which each second entity 126 is color coded in the upper panel 420 by its k-means cluster 158 identity. As such, the k-means clustering itself is deemed a category 170 and the clusters 158 are each deemed a different class 172 of the category 170.

In some embodiments, where there is a category 170 in a discrete attribute value dataset 120 having classes 172, each respective second entity in the discrete attribute value dataset 120 is a member of each respective category 170 and one of the classes 172 of each respective category 170. In some such embodiments, where the dataset comprises a plurality of categories 170, each respective second entity in the discrete attribute value dataset 120 is a member of each respective category 170, and a single class of each respective category 170.

In some embodiments where there is a category 170 in a discrete attribute value dataset 120 that has no underlying classes 172, a subset of the second entities in the dataset 120 are a member of the category 170.

In some embodiments where there is a category 170 in a discrete attribute value dataset 120 having subclasses 172, only a portion of the respective second entities in the dataset 120 are a member of the category 170. Moreover, each second entity in the portion of the respective second entities is independently in any one of the respective classes 172 of the category 170.

As illustrated in FIG. 11, a user can select or deselect any category 170. As further illustrated, a user can select or deselect any combination of subcategories 172 in a selected category 170. Referring to FIG. 11, in some embodiments, the user is able to click on a single cluster 158 (the clusters 1-10 are labeled as 172-1-2, 172-1-3, 172-1-4, 172-1-5, 172-1-6, 172-1-7, 172-1-8, 172-1-9, 172-1-10, respectively, in FIG. 11) to highlight it in the plot 420. In some embodiments, when the user clicks on a highlighted cluster 158 in the plot 420, the highlighting is removed from the selected cluster.

Figure 13:
FIG. 13 illustrates how the globally distinguishing affordance 1204 of FIG. 12 identifies the second entities 126 (e.g., genes) whose discrete attribute values (e.g., mRNA counts) uniquely identify the "Normal1" and "Normal2" classes amongst the entire dataset which includes the data for the second entities that are in the "AMLpatient" class in accordance with some embodiments of the present disclosure.

Continuing to refer to FIG. 11, the category 170 "LibraryID," is a category 170 in which each second entity 126 is color coded in the upper panel by its LibraryID. This is illustrated in FIG. 13. Each second entity 126 in the discrete attribute value dataset 120 is a member of the category "LibraryID." The category 170 "LibraryID" has three classes 172 "Normal1" 172-2-1, "Normal2" 172-2-2, and AMLPatient "172-2-3." In FIG. 13, the user has selected to use the classes "Normal1" 172-2-1 and "Normal2" 172-2-2 but not AMLPatient "172-2-3."

Figure 12:
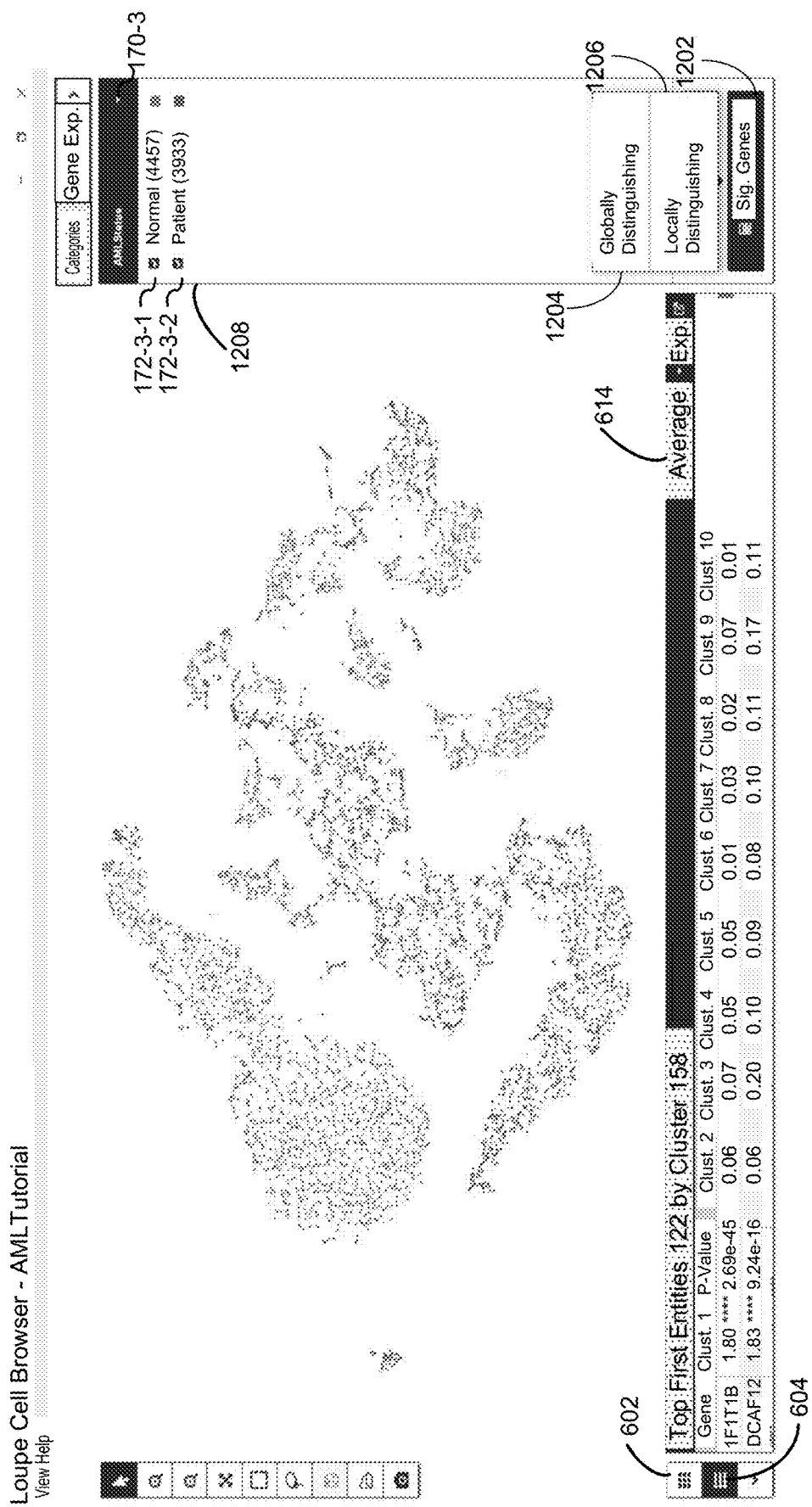
FIG. 12 illustrates how each second entity is color coded in an upper panel by its acute myeloid leukemia (AML) status (e.g., blood cells that are from a normal donor versus blood cells that are from a subject with acute myeloid leukemia) in accordance with some embodiments of the present disclosure.

Referring back to FIG. 11, selection of the category "AMLStatus" 170-3 leads to the view provided in FIG. 12, in which each second entity is color coded in the upper panel 420 by its acute myeloid leukemia (AML) status (e.g., blood cells that are from a normal donor versus blood cells that are from a subject with acute myeloid leukemia). Note that the spatial representation of the cells in the upper panel does not change by selection of one of the categories 170, only the labeling for the second entities changes. In FIG. 12, in a panel 1208, it is seen that the AMLStatus category 170-3 includes a normal class 172-3-1 and a patient class 172-3-2. The category AMLStatus 170-3 encompasses all of the second entities 126 in the discrete attribute value dataset 120. Each second entity is then characterized into one of the classes of AMLStatus 170-3, normal (does not have AML) or patient (has AML).

The presentation of the data in the manner depicted for example in FIGS. 11 through 14 advantageously provides the ability to determine the first entities 122 whose discrete attribute values 124 separates (discriminates) classes 172 within a selected category based upon their discrete attribute values. To further assist with this, the significant first entities (e.g., Sig. genes) affordance 1202 is selected thereby providing two options, option 1204 (globally distinguishing) and option 1206 (locally distinguishing).

Referring to FIG. 13, the globally distinguishing option 1204 identifies the first entities 122 whose discrete attribute values 124 within the selected classes 172 statistically discriminate with respect to the entire discrete attribute value dataset 120 (e.g., finds genes expressed highly within the selected categories 170, relative to all the categories in the dataset 120). The locally distinguishing option 1206 identifies the first entities whose discrete attribute values discriminate the selected classes (e.g., AMLNormal1, AML-Normal2, in FIG. 13) without considering the discrete attribute values 124 in classes 172 of second entities that have not been selected (e.g., without considering the AML-Patient class 172-2-3 of the category LibraryId category 170-2 of FIG. 13).

In some embodiments, visualization system 100 comprises a plurality of processing cores 102 and the identification of first entities whose discrete attribute values discriminate classes under either the globally distinguishing or locally distinguishing algorithms makes use of the processing cores 102 to independently build up needed statistics (e.g., a measure of central tendency of the discrete attribute value) of individual first entities across a class and/or one or more categories of a class of second entities (or the entire dataset).

To further illustrate, turning to FIG. 13 in which the "LibraryID" category 170-2 option has been selected and the data for the second entities in the AMLPatient class 172-2-3 have been deselected, the globally distinguishing affordance 1204 of FIG. 12 identifies the second entities 126 (e.g., genes) whose discrete attribute values (e.g., mRNA counts) uniquely identify the "Normal1" 172-2-1 and "Normal2" 172-2-2 classes amongst the entire discrete attribute value dataset 120 which includes the data for the 3933 second entities that are in the "AMLpatient" class 172. These are listed out in the lower panel 404. By contrast, as illustrated in FIG. 14, the locally distinguishing option identifies the first entities 122 whose discrete attribute values 124 discriminate the difference between the "Normal1" and "Normal2" classes 172 without consideration of the discrete attribute values 124 of the first entities 122 in the second entities 126 that are in the "AMLPatient" class 172, because the "Normal1" and "Normal2" classes are the only two classes of the selected LibraryID category 172 that are selected.

Figure 14:
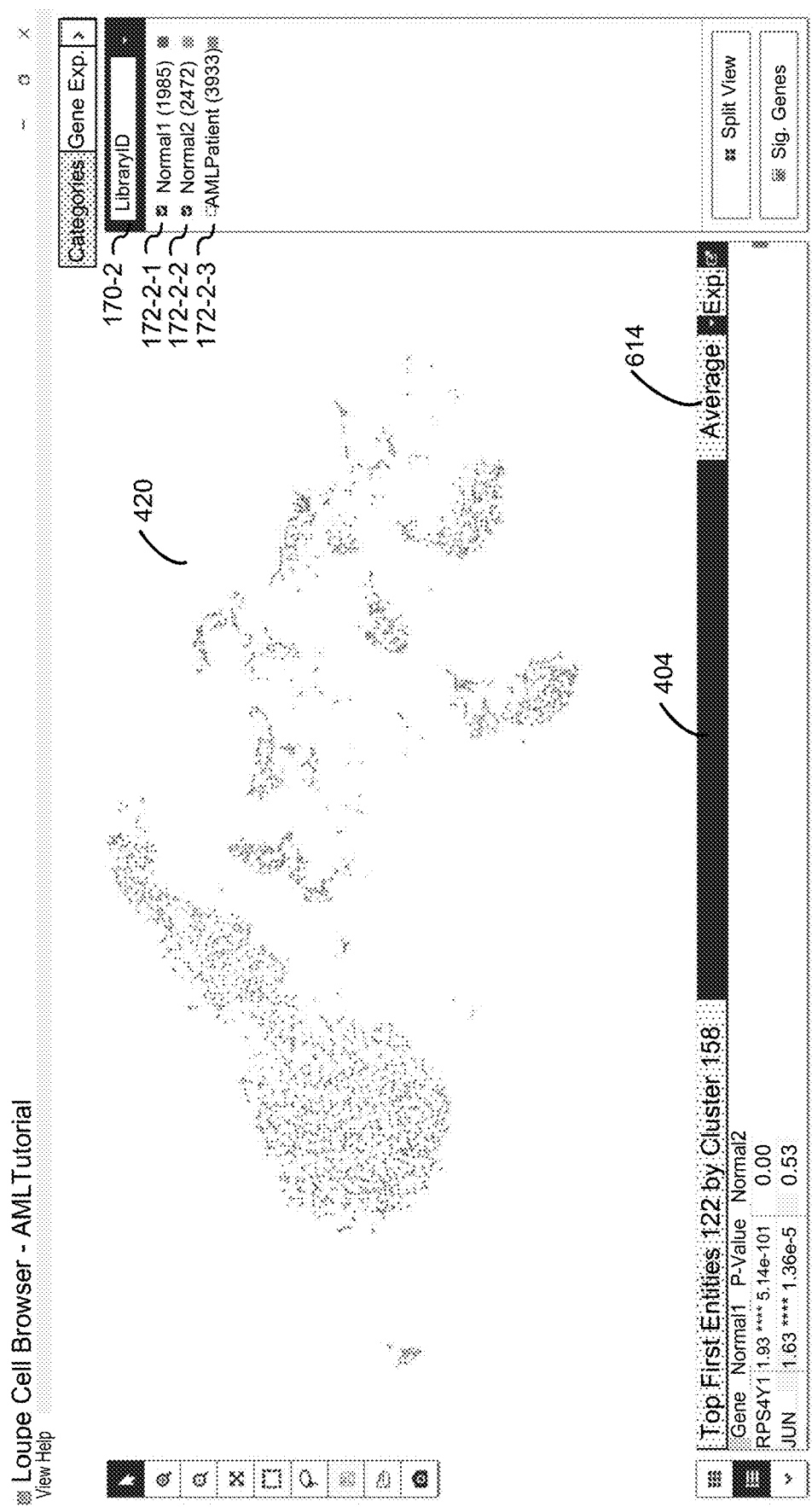
FIG. 14 illustrates how the locally distinguishing option identifies the first entities whose discrete attribute values discriminate the difference between the "Normal1" and "Normal2" classes without consideration of the discrete attribute values of the first entities in the second entities that are in the "AMLPatient" class, because the "Normal1" and "Normal2" classes are the only two classes of the selected LibraryID category that are selected in accordance with some embodiments of the present disclosure.

Advantageously, the systems and method of the present disclosure allow for the creation of new categories 170 using the upper panel 420 and any number of classes 172 within such categories using lasso 1402 or box selection tool 1404 of FIG. 14. So, if a user would like to identify second entity subtypes (classes 172), this can be done by selecting a number of second entities displayed in the upper panel 420 with the lasso tools. Moreover, they can also be selected from the lower panel 404 (e.g., the user can select a number of second entities by their discrete attribute values). In this way, a user can drag and create a class 172 within a category. The user is prompted to name the new category 170 and the new class 172 within the category. The user can create multiple classes of second entities within a category. Once the classes 172 of a category have been defined in this way, the user can compute the first entities whose discrete attribute values 124 discriminate between the identified user defined classes. In some such embodiments, such operations proceed faster than with categories that make use of all the second entities in the discrete attribute value dataset 120 because fewer numbers of second entities are involved in the computation. In some embodiments, the speed of the algorithm to identified first entities that discriminate classes 172 is proportional to the number of classes 172 in the category 170 times the number of second entities that are in the analysis. For instance, in some embodiments identification of discriminating first entities in the case where there are two classes and twenty-five second entities takes about four to five seconds on a standard client device 100.

In some embodiments, a discrete attribute value dataset 120 can have data for up to 750,000 second entities and still identified first entities that discriminate between classes of 172 of a category 170 in real time (e.g., less than 30 minutes, less than 10 minutes, less than 5 minutes, or less than 1 minute).

Embodiments in which data is filtered on both discrete attribute values 124 and clonotypes 1624. Advantageously, in embodiments where the discrete attribute value datasets 120 arising from sequencing pipelines that sequence mRNA from single cells, such as B-cells and T-cells, it is possible to combine the discrete attribute value data 124 for second entities 122 described above with V(D)J clonotype data 1624, for instance that has been obtained as described in United States Patent Application No. 62,508,947, entitled "Systems and Methods for Analyzing Datasets," filed May 19, 2017, which is hereby incorporated by reference, where the discrete attribute data 124 and the V(D)J clonotype data 1624 are obtained from the same second entities 126. That is, the discrete attribute values 124 (e.g., gene expression) and the V(D)J repertoire is measured from the same second entities (e.g. same cells). In some such embodiments, for the discrete attribute value dataset 120 of discrete attribute values, there is a corresponding clonotype dataset 1602 and VDJ chain reference sequence table 1640. In some such embodiments, the clonotype dataset 1602 and the V(D)J chain reference sequence table 1640 are loaded by the cell browser 119 in conjunction with the discrete attribute value dataset 120. In instances where a user runs a discrete attribute value 124 (e.g., gene expression) pipeline and a V(D)J pipeline in order to concurrently analyze discrete attribute values 124 of first entities 122 (e.g., gene expression) and V(D)J clonotype 1624 from the same second entities 126 (e.g., same cells), a user will split barcoded reads into a plurality of libraries (e.g., two libraries, three libraries, four libraries, or more than four libraries).

For instance, in some embodiments mRNA from a single second entity 126 is amplified and barcoded with the same barcode. In some such embodiments, discrete attribute values are measured from single cells, and microfluidic partitions are used to capture such individual cells within respective microfluidic droplets and then pools of single barcodes within each of those droplets are used to tag all of the contents (e.g., first entities 122) of a given second entity 126. For example, in some embodiments, a pool (e.g., of 750,000 barcodes) is sampled to separately index each second entities' transcriptome by partitioning thousands of second entities into nanoliter-scale Gel Bead-In-EMulsions (GEMs), where all generated cDNA share a common barcode. In some embodiments, each respective droplet (GEM) is assigned its own barcode and all the contents (e.g., first entities) in a respective droplet are tagged with the barcode unique to the respective droplet. In some embodiments, such droplets are formed as described in Zheng et al., 2016, Nat Biotchnol. 34(3): 303-311; or in See the Chromium, Single Cell 3' Reagent Kits v2. User Guide, 2017, 10X Genomics, Pleasanton, California, Rev. B, page, 2, each of which is hereby incorporated by reference.

The amplified DNA from such mRNA, now barcoded, is pooled across the population of cells in a test sample (e.g. a tumor biopsy, etc.) and then divided into two or more aliquots, three or more aliquots, four or more aliquots, ten or more aliquots, etc. Each such respective aliquot includes one or more barcoded cDNA constructs, for each of the mRNA in each second entity 126 (e.g., cell) in the original sample. That is, each respective aliquot fully represents the relative expression of each expressed first entity 122 from each second entity 126 in the original sample. Moreover, because the first entity 122 was barcoded upon amplification to cDNA, it is possible to identify a cDNA from one of the aliquots as being from the same first entity 122 (e.g., gene) as the cDNA from the other aliquots, because they will have matching barcodes. As such, one of the respective aliquots is applied to the general V(D)J transcript library construction and selection protocol described in United States Patent Application No. 62,508,947, entitled "Systems and Methods for Analyzing Datasets," filed May 19, 2017, and further disclosed in the section below entitled "V(D)J Pipeline" thereby populating the clonotype dataset 1602, and another of the aliquots follows a 5' gene expression library construction protocol, such as the one below described in the section entitled "Discrete attribute value pipeline," thereby populating the discrete attribute values 124 for each first entity 122 for each second entity 126 in the test sample in the discrete attribute value dataset 120. In some embodiments, the test sample comprise 10 or more second entities, 100 or more second entities, or 1000 or more second entities. In some embodiments, the test sample is a biopsy from a subject, such as a human subject. In some embodiments, the sample is a biopsy of a tumor and contains several different cell types.

A such, barcoded sequence reads from each library generated using the original barcoded amplified cDNA that share the same barcode will most likely have come from the same second entity. Moreover, as further discussed below, other aliquots in the plurality of aliquots can be subjected to other forms of single cell sequence or expression analysis and data derived from such pipelines can be indexed to individual second entities 126 in the discrete attribute value dataset based on common barcodes.

Thus, in a joint discrete attribute value 124 (e.g. gene expression)/targeted V(D)J experiment, users will create the above-described libraries (e.g., first and second aliquot described above) and run the respective analysis pipeline for each library, such as the pipeline disclosed in the section below entitled "Discrete attribute value pipeline," as well as the pipeline disclosed in the section below entitled "V(D)J Pipeline" thereby respectively populating the discrete attribute value dataset 120 and the clonotype dataset 1602. In other words, once the analysis pipelines have completed, the discrete attribute value 124 (e.g., gene expression) pipeline will yield a discrete attribute value dataset 120 (e.g., a cell browser 119 (.cloupe) file, as disclosed in U.S. Provisional Patent Application No. 62/456,547, filed Feb. 8, 2017 entitled "Systems and Methods for Visualizing a Pattern in a Dataset," which is hereby incorporated by reference, and further detailed in the section below entitled the "Discrete attribute value pipeline"). The targeted VDJ pipeline will yield a clonotype dataset 1602 (e.g., Loupe VDJ Browser (vloupe) file, as disclosed in United States Patent Application No. 62/508,947, entitled "Systems and Methods for Analyzing Datasets," filed May 19, 2017, which is hereby incorporated by reference, and disclosed in the section below entitled "V(D)J Pipeline." Because the discrete attribute value dataset 120 and the clonotype dataset 1602 share common barcodes because they are derived from common second entities in the biological sample under study, the cell browser 119 is able to import the clonotype information 1602 of the clonotype dataset 1602 into the discrete attribute workspace of the corresponding discrete attribute value dataset 120. Because the discrete attribute values 120 of the first entities 122 of the discrete attribute value dataset 120 are directly traceable to single corresponding single second entities 126 in both the discrete attribute value dataset 120 and the corresponding clonotype dataset 1602 thereby providing the clonotype information 1624 for such barcodes, this feature advantageously provides an example of integrated single first entity (e.g. single-cell) genomic analysis, where a worker can combine information about the same second entities (e.g., same cells) arising from two or more different data processing pipelines (the clonotype dataset 1602 and the discrete attribute value dataset 120) in order to provide new, multi-faceted information about those single second entities (e.g. cells). In addition, such embodiments of the cell browser 119 that can access both the clonotype dataset 1602 and the discrete attribute value dataset 120 in which first entities 122 have been indexed to a single second entity 126 and to a clonotype 1624 through common barcodes in the clonotype dataset 1602 and the corresponding discrete attribute value dataset 120, enables the review of the discrete attribute values using clonotype as a filter.

Figure 17:
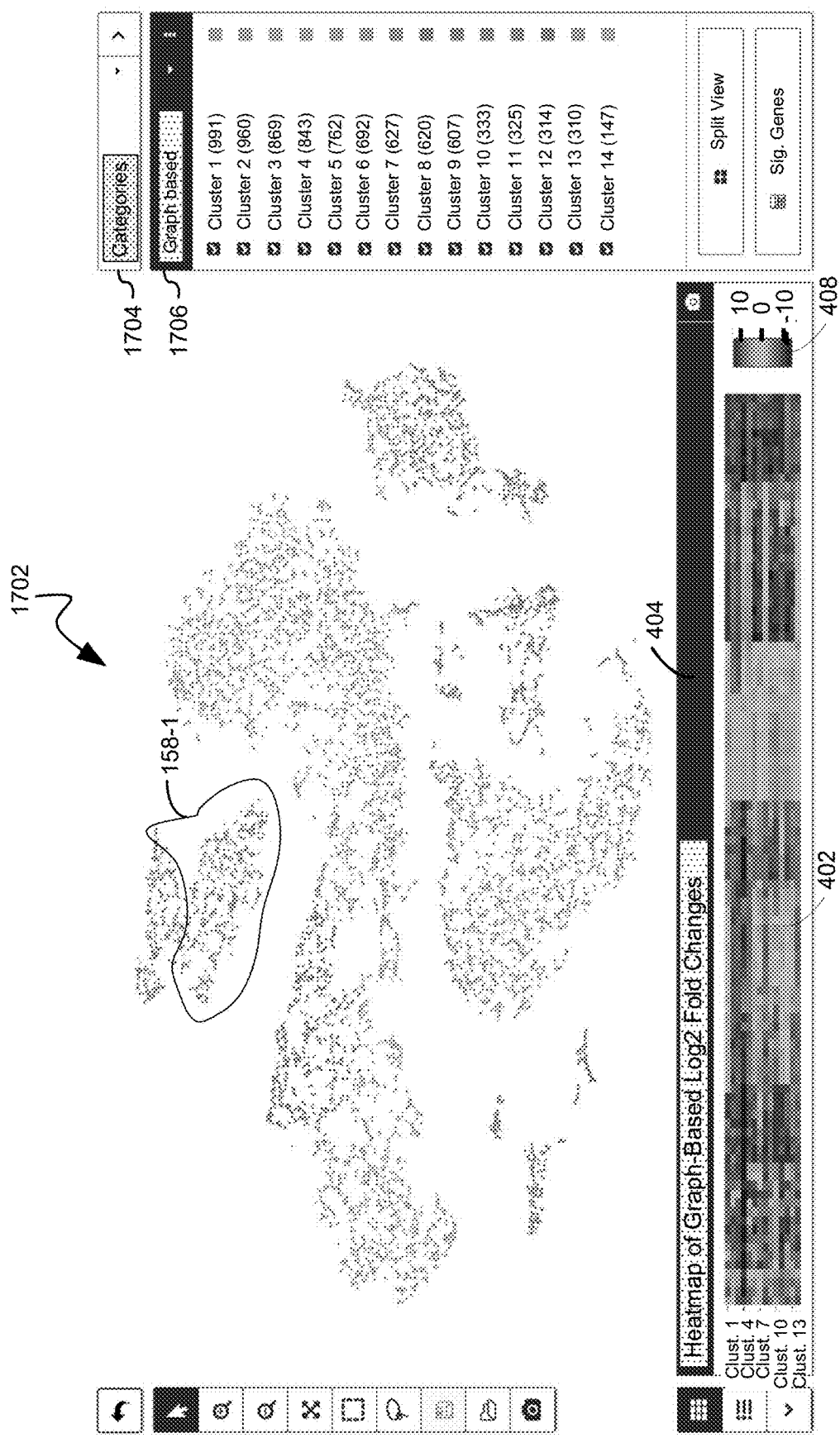
FIG. 17 illustrates an example display in which a heat map that comprises a representation of the differential value for each respective first entity in a plurality of first entities for each cluster in a plurality of clusters is displayed in a first panel while each respective second entity in a plurality of entities is displayed in a second panel based upon a dimension reduced two-dimensional data point for the respective second entity in accordance with some embodiments of the present disclosure.
Figure 18:
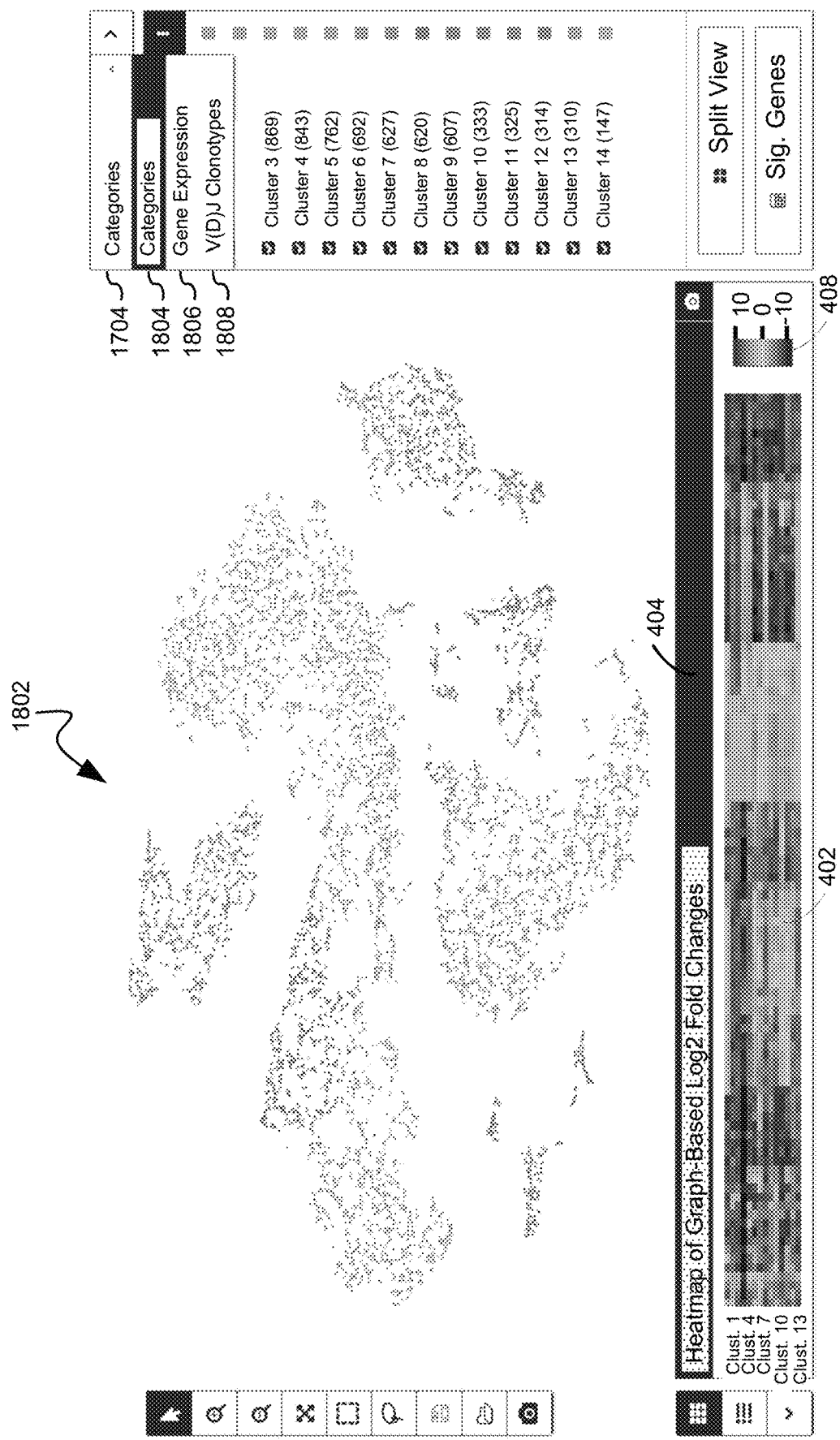
FIG. 18 illustrates how a user can select between "Categories," "Gene Expression," and "V(D)J Clonotypes" visualization modes in accordance with some embodiments in which a cell browser has obtained one or more clonotype datasets indexed to a discrete attributed value dataset, based on common barcodes between the datasets, in accordance with some embodiments of the present disclosure.

Referring to FIG. 17, when a dataset in accordance with such embodiments of the present application is loaded, the cell browser 119 provides the panel 1702 illustrated in FIG. 17, which is a heat map prepared in accordance with block 206 described above in conjunction with FIG. 4. Namely, the differential value 162 for each respective first entity 122 in the plurality of first entities for each respective cluster 158 in the plurality of clusters derived from a discrete attributed value dataset 120 are computed, and a heat map 402 of these differential values is displayed in a first panel 404 of an interface 1702 of FIG. 17. The heat map 402 comprises a representation of the differential value 162 for each respective first entity 122 in the plurality of first entities for each cluster 158 in the plurality of clusters. In FIG. 17, the clusters are formed in accordance with block 214 in which a Louvain modularity algorithm is used. See, Blondel et al., Jul. 25, 2008, "Fast unfolding of communities in large networks," arXiv:0803.0476v2 [physical.coc-ph], which is hereby incorporated by reference.

As illustrated in FIG. 17, the differential value 162 for each first entity 122 in the plurality of entities for each cluster 158 is illustrated in a color coded way to represent the $\log_2$ fold change in accordance with color key 408. In accordance with color key 408, those first entities 122 that are upregulated in the second entities 126 of a particular cluster 158 relative to all other clusters are assigned more positive values, whereas those first entities 122 that are down-regulated in the second entities 126 of a particular cluster 158 relative to all other clusters are assigned more negative values. In some embodiments, the heat map can be exported to persistent storage (e.g., as a PNG graphic, JPG graphic, or other file formats).

Figure 19:
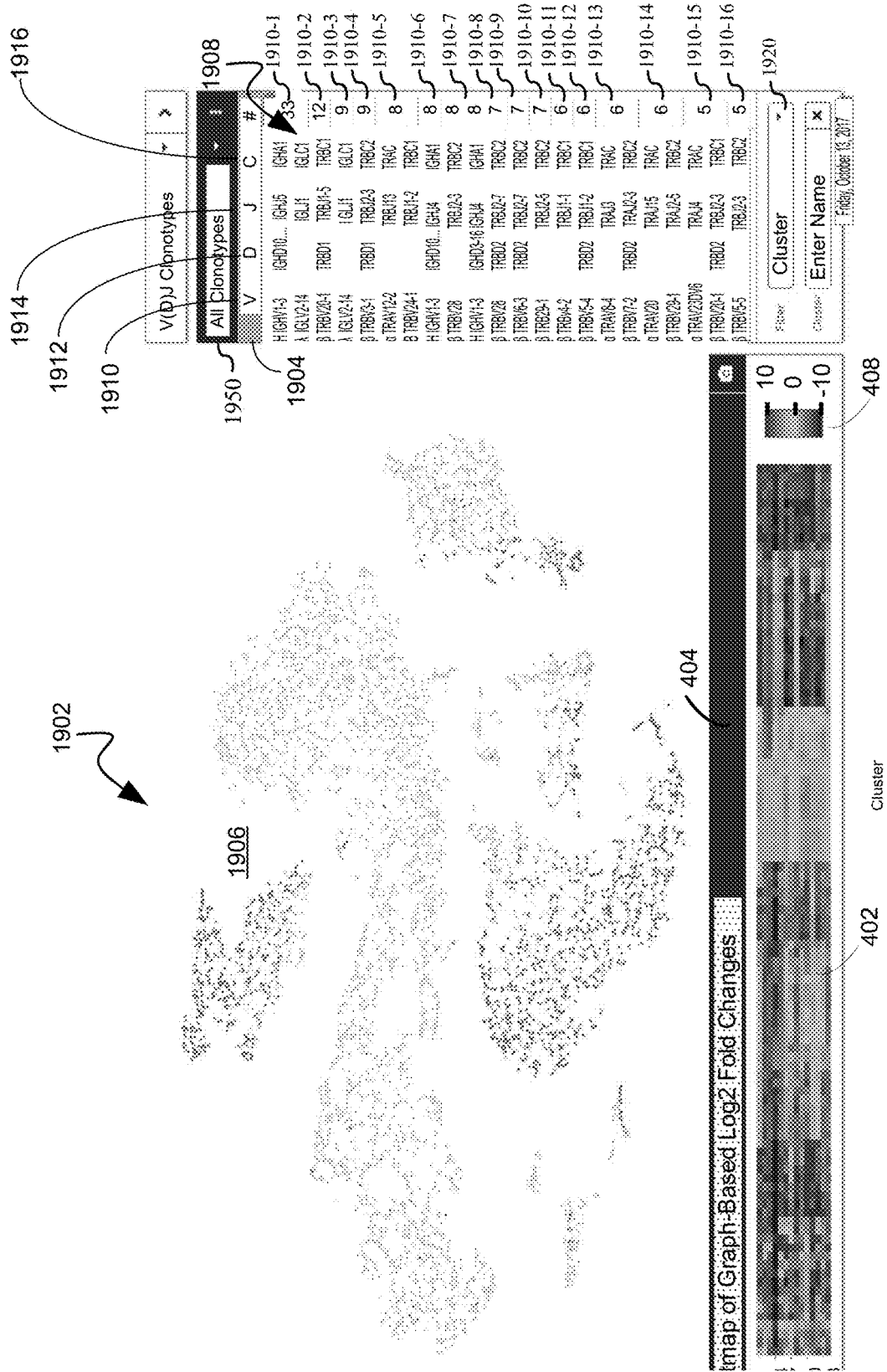
FIG. 19 illustrates an example display in which a heat map that comprises a representation of the differential value for each respective first entity in a plurality of first entities for each cluster in a plurality of clusters is displayed in a first panel while each respective second entity in a plurality of entities is displayed in a second panel based upon a dimension reduced two-dimensional data point, and furthermore each respective second entity in the plurality of entities displayed in the second panel is color coded based on whether or not it is represented by a common barcode in both a discrete attribute value dataset 120 and a clonotype dataset 1602B in accordance with some embodiments of the present disclosure.

Referring to FIG. 17, advantageously, affordance 1704 can be used to toggle to other visual modes. In FIG. 17, a particular "Categories" mode, "Graph based" (1706) is depicted, which refers to the use of a Louvain modularity algorithm to cluster discrete attribute value 124 as disclosed above with reference to block 214. However, by selecting affordance 1704, other options are displayed for affordance 1702 as illustrated in panel 1802 of FIG. 18. In particular, in addition to the "Categories" option 1804 that was displayed in FIG. 17, "Gene Expression" 1806, and "V(D)J Clonotypes" 1808 can be selected as options for affordance 1704. The "Categories" 1804 option has been described above, for example, with reference to FIG. 11 in which the second entities in the biological sample that was used as a basis for forming the discrete attribute dataset 120 are grouped into clusters 158. The "Gene Expression" option 1806 has been described above, for example, with reference to FIG. 4. Selection of the "V(D)J Clonotypes" option 1808 for affordance 1704 of FIG. 18 leads to panel 1902 of FIG. 19, which list the top clonotypes 1624 from the combination of four V(D)J runs, and their frequencies (e.g., number of second entities having such clonotypes), in the context of the overall clustered expression of second entities from the biological sample. That is, in FIG. 19, like in FIGS. 17 and 18, the second entities appear clustered in the main panel 1902 in accordance with the Louvain modularity algorithm. Data for each of the four V(D)J runs is obtained in accordance with the section below entitled "V(D)J Pipeline." While the second entities 126 of the underlying biological sample used to build the discrete attribute value dataset 120 and clonotype dataset 1602 that is concurrently displayed in FIG. 19 are still arranged into their clusters in accordance with the Louvain modularity algorithm as described above in conjunction with block 214, they are no longer color coded by cluster 158 types. That is, although the second entities are still arranged into the clusters 158 produced through the Louvain modularity algorithm in accordance with block 214, the second entities are not color coded by which cluster 158 they fall into as was the case in FIGS. 17 and 18. Rather, those second entities 126 represented in the discrete attribute value dataset 120 that are also represented in the form of contigs 1628 in the clonotype dataset 1602, are displayed with a first attribute (e.g., red) and those second entities 126 represented in the discrete value dataset 120 that are not also in the clonotype dataset 1602 are displayed with a second attribute (e.g., greyed out). In typical embodiments, those second entities 126 represented in the discrete attribute value dataset 120 that are also represented in the form of contigs 1628 in the clonotype dataset 1602 is evidenced by the fact that such second entities are supported by the same barcode 1630 in both datasets. As an example, with reference to FIG. 1B, consider the case of a second entity 126 in the discrete attribute value dataset 120. This second entity is supported by a barcode on the basis that the second entity sequence information was obtained from the Discrete attribute value pipeline, for example, in accordance with the section below entitled "Discrete attribute value pipeline." Moreover, in cases where this second entity 126 is a T-cell or B-cell, that was also subjected to the V(D)J Pipeline described below, it is also represented by a contig 1628, which is supported by a barcode 1630, in the clonotype dataset 1602. As such, it is possible to match the contig 1628, in the clonotype dataset 1602, that was obtained from the exact same second entity 126 in the V(D)J pipeline that was used to obtain the discrete attribute value 124 for that second entity 126 that was obtained in the expression pipeline disclosed in the section below entitled "Discrete attribute value pipeline." In FIG. 19, those second entities 126 in the common biological sample that are in fact matched between the clonotype dataset 1602 and the discrete attribute value dataset 120 through their matching underlying barcodes in this way are displayed with one attribute (e.g. red) whereas those second entities represented in the discrete attribute value dataset 120 that have no matching counterpart in the clonotype dataset 1602 are shown in a second color (e.g., greyed out). Because each second entity represented in the clonotype dataset 1602 is matched to a clonotype 1624, it is possible to visualize which clusters 158 the clonotypes 1624 represented in the clonotype dataset 1602 map into. Moreover, as illustrated in FIG. 19, which includes data from four separate runs of the V(D)J pipeline disclosed below in the section entitled V(D)J Pipeline, this barcode matching makes it possible to view the union of clonotypes 1624 and clonotype counts (how many second entities have a particular clonotype in a given biological sample of second entities) across multiple V(D)J samples. FIG. 19 illustrates this for the case of B-cell chains. Thus, as illustrated in FIG. 19, when the V(D)J clonotypes 1808 view is selected in FIG. 18, the second entities (e.g. cells) that belong to clonotypes in the list 1904 (critically, their barcodes match) are highlighted in the gene expression projection (main panel 1906 of 1902). This allows users to see where clonotypes of interest may fall in the first entity expression clusters 158.

Referring to FIG. 19, each box 1910 in Table 1908 is the clonotype 1624 of a particular set of contigs 1628. There may be multiple second entities 126 represented by this clonotype 1624 in the clonotype dataset 1602. For instance, referring to FIG. 19, in the biological sample represented by the clonotype dataset 122, there are 32 second entities 126 (e.g., cells) that have the clonotype 1624 described in box 1901-1, 12 second entities 126 that have the clonotype 1624 described in box 1910-2, 6 second entities 126 that have the clonotype 1624 described in box 1910-3, 9 second entities 126 that have the clonotype 1624 described in 1910-4, 8 second entities 126 that have the clonotype 1624 described in box 1910-5, and so forth for second entities that have the clonotype described in boxes 1910-6, 1910-7, 1910-8, 1910-9, 1910-10, 1910-11, 1910-12, 1910-13, 1910-14, 1910-15, 1910-16. The clonotype illustrated in box 1910-1 includes one contig type for an H chain and another contig type for a λ, chain. The clonotype illustrated in box 1910-2 includes one contig type for a β chain. Further, each respective box 1910 in list 1908 indicates how many second entities 126 in the discrete attribute dataset 120 have the clonotype 1624 represented by the respective box. For instance, there are 33 second entities 126 in the discrete attribute dataset 120 that have the clonotype of box 1910-1. It is possible for the V(D)J pipeline, referenced below, to detect a second entity that does not appear in the discrete attribute value dataset 120. In some embodiments, such a second entity does not contribute to count 1910 shown by the cell browser 119, since the second entity does not have a corresponding barcode in the discrete attribute value dataset 120.

For each chain type represented in a clonotype 1624, table 1908 of FIG. 19 provides an identifier 1909 for the V segment, an identifier 1912 for the diversity region (present in the case of T-cell β chains and δ chains, but not a chains and γ chains), an identifier 1914 for the J region, and an identifier for the C region 1916. Two second entities 126 are deemed to have the same clonotype 1624 if their respective receptor chains have the same corresponding CDR3 sequences. Due to the heterozygous nature of the cells being sampled, it is possible for a single cell in the sample represented by the clonotype dataset 1602 illustrated in FIG. 16 to have up to two different α chains as well as up to two different β chains. In other words, due to the heterozygous nature of the cells being sampled, it is possible for a single second entity 126 in the sample represented by the clonotype dataset 1602 illustrated in FIG. 16, and further illustrated in FIG. 19, to have a first α chain with a first CDR3 sequence, a second α chain with a second CDR3 sequence, a first β chain with a third CDR3 sequence, and a second β chain with a fourth CDR3 sequence.

The VDJ region is about 700 bases in length whereas, in some embodiments, the sequence reads 1634 are about 150 base pairs long. Therefore, situations arise in which some mRNA molecules encoding the VDJ region only get sequence reads 1634 on one part of the VDJ region (V only or J only) and not the other part of the VDJ region and so the V region or the J region is not represented for such mRNA molecules. In such instances, it is not possible to determine the clonotype of such second entities. In order to have an assigned clonotype, there has to be within a single second entity a sequence read with a particular UMI code that aligns to a V gene and another sequence read with the particular UMI code that aligns to a J gene. In the alternative, longer sequence reads are employed that align to the entire VDJ region. In the alternative still, sequence reads having the same UMI are employed that collectively align to the entire VDJ region.

Figure 20:
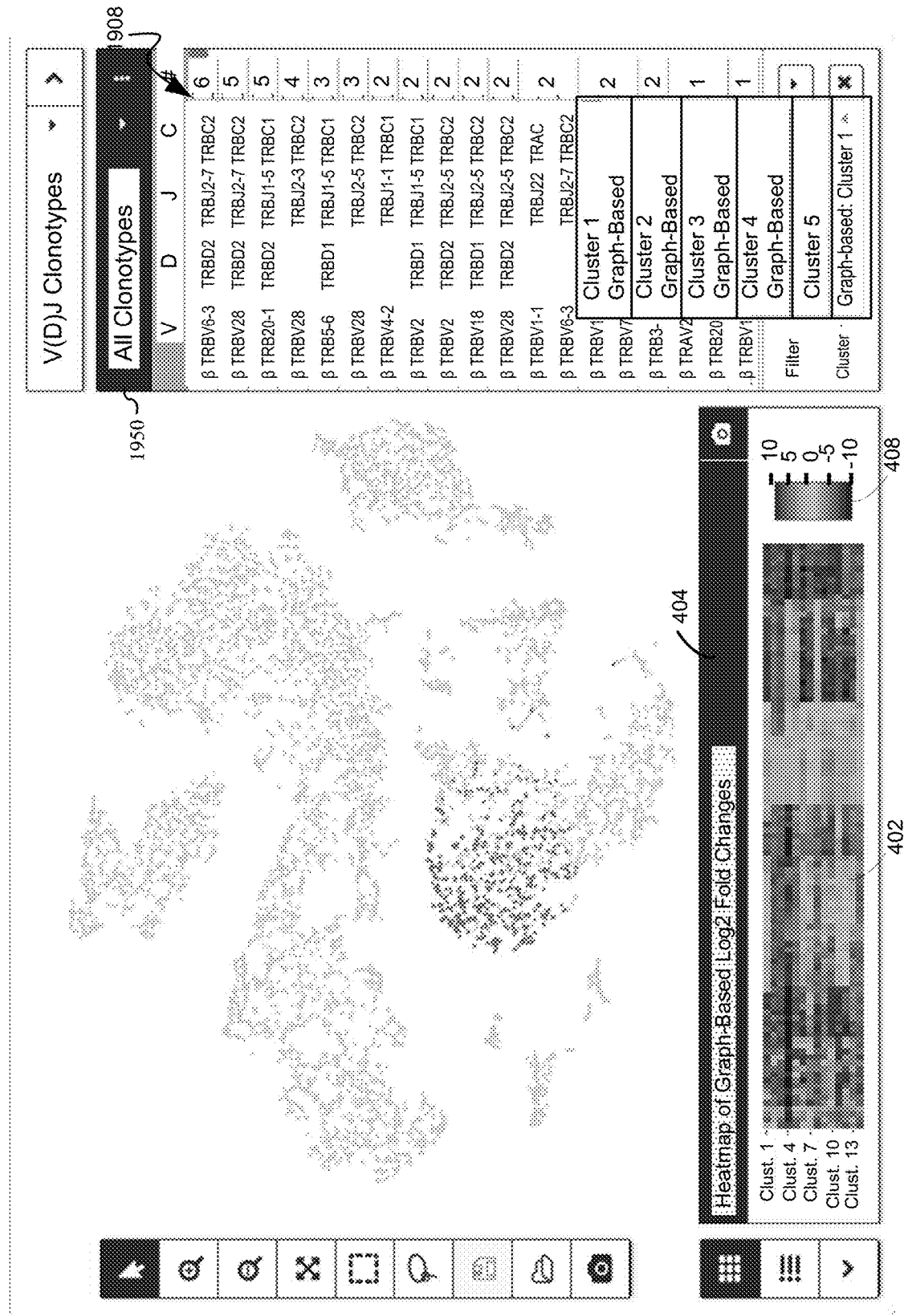
FIG. 20 illustrates an example display in which a heat map that comprises a representation of the differential value for each respective first entity in a plurality of first entities for each cluster in a plurality of clusters is displayed in a first panel while each respective second entity in a plurality of entities is displayed in a second panel based upon a dimension reduced two-dimensional data point, and furthermore each respective second entity in the plurality of entities displayed in the second panel is color coded based on whether or not it satisfies the joint filtering criterion of (i) being represented by a common barcode in both a discrete attribute value dataset 120 and a clonotype dataset 1602B and (ii) falling into a selected cluster, in accordance with some embodiments of the present disclosure.
Figure 24:
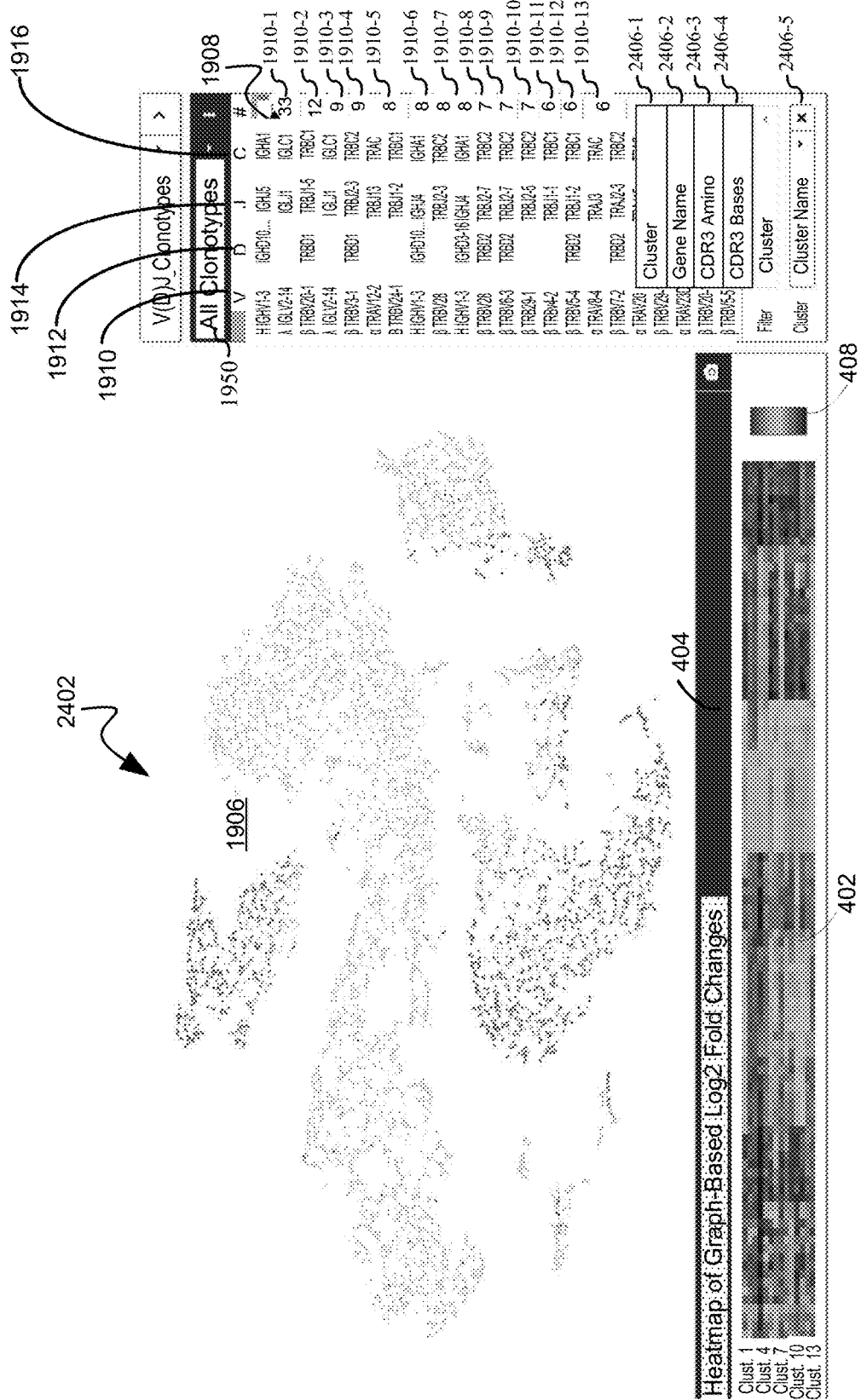
FIG. 24 illustrates a user interface for filtering clonotypes on the basis of which cluster they fall into, gene name, CDR3 amino acid sequence, or CDR3 base sequence in accordance with some embodiments of the present disclosure.

Filtering the Clonotype List. The number of clonotypes 1624 in a given clonotype dataset 122 can be quite large. Accordingly, referring to FIG. 19, in some embodiments, selection of affordance 1920 changes the view of panel 1902 to that of panel 2402 of FIG. 24 in which filter options cluster 2406-1, gene name 2406-2, CDR3 Amino 2406-3, and CDR3 Bases 2406-4 can be used to filter list 1909. Moreover, in some embodiments a scroll bar (not shown) can be used to traverse list 1908. For instance, filter "Gene Name" 2406-2 permits one to filter by gene name (e.g., individual V or J gene name), filter "CDR3 Amino" 2406-3 permits one to filter by specific CDR3 amino acid sequence, "CDR3 Bases" 2406-4 permits one to filter by specific CDR3 nucleic acid sequence. Additionally, one may filter the clonotype list by gene expression cluster 158, by selecting the "Cluster" 2406-1 as the filter. A cluster name can be selected via an option 2406-5, as shown in FIG. 24. With Cluster 2406 selected, typing the name of a target cluster in field 2406 will bring up a list of potential matches. FIG. 20 illustrates by showing the state of the display provided by the cell browser 119 when "Cluster 1" from the Graph-Based clustering scheme has been selected. The red dots in FIG. 20 are the second entities from that cluster 158 that had transcripts (first entities) detected in the V(D)J runs. The clonotype list of FIG. 20 shows the distribution of clonotypes within second entities in Cluster 1.

Figure 21:
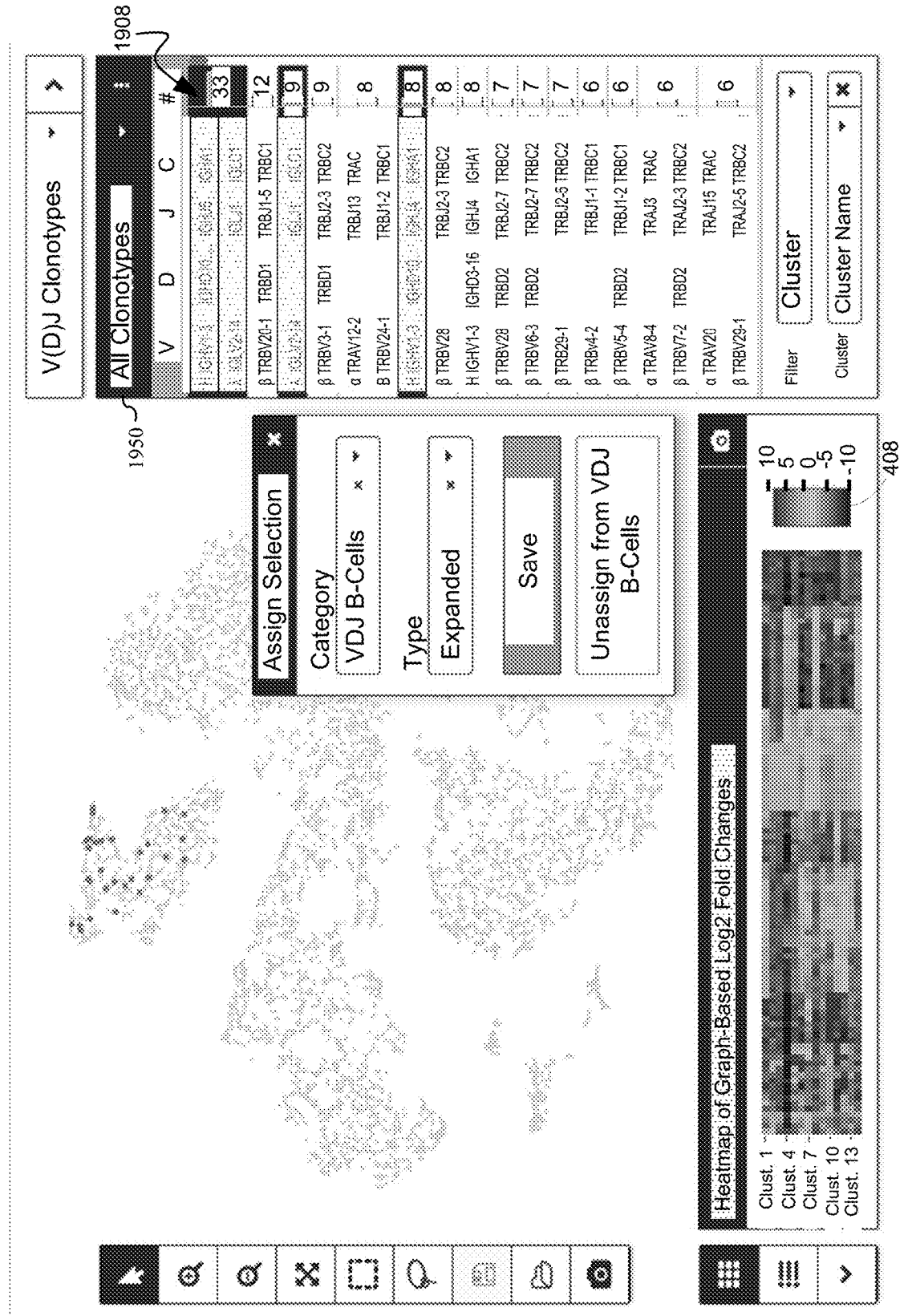
FIG. 21 illustrates how selected second entities, that have been identified using selection techniques such as those illustrated in FIG. 21, can be saved as clonotype list-derived clusters to thereby identify significant first entities, or other biological information, in accordance with some embodiments of the present disclosure.

One may select one or more clonotypes from the clonotype list 1908. Selection of multiple clonotypes is done in some embodiments, for example, via holding down the "control" key on the keyboard while selecting individual clonotypes from the list 1908 with mouse clicks. Alternatively, one may select all clonotypes in the clonotype list 1908 by selecting the "All Clonotypes" menu option at affordance 1950. When clonotypes in the clonotype list 1908 are selected, the second entities having those clonotypes will be highlighted in panel 1906 with a different attribute (e.g., different color) and/or larger marker. As illustrated in FIG. 21, right-clicking on the clonotype list 1908 will allow the user to assign cells within the currently selected clonotypes into a new cluster 158. Users can use those clonotype list-derived clusters to identify significant first entities, or other information.

Figure 22:
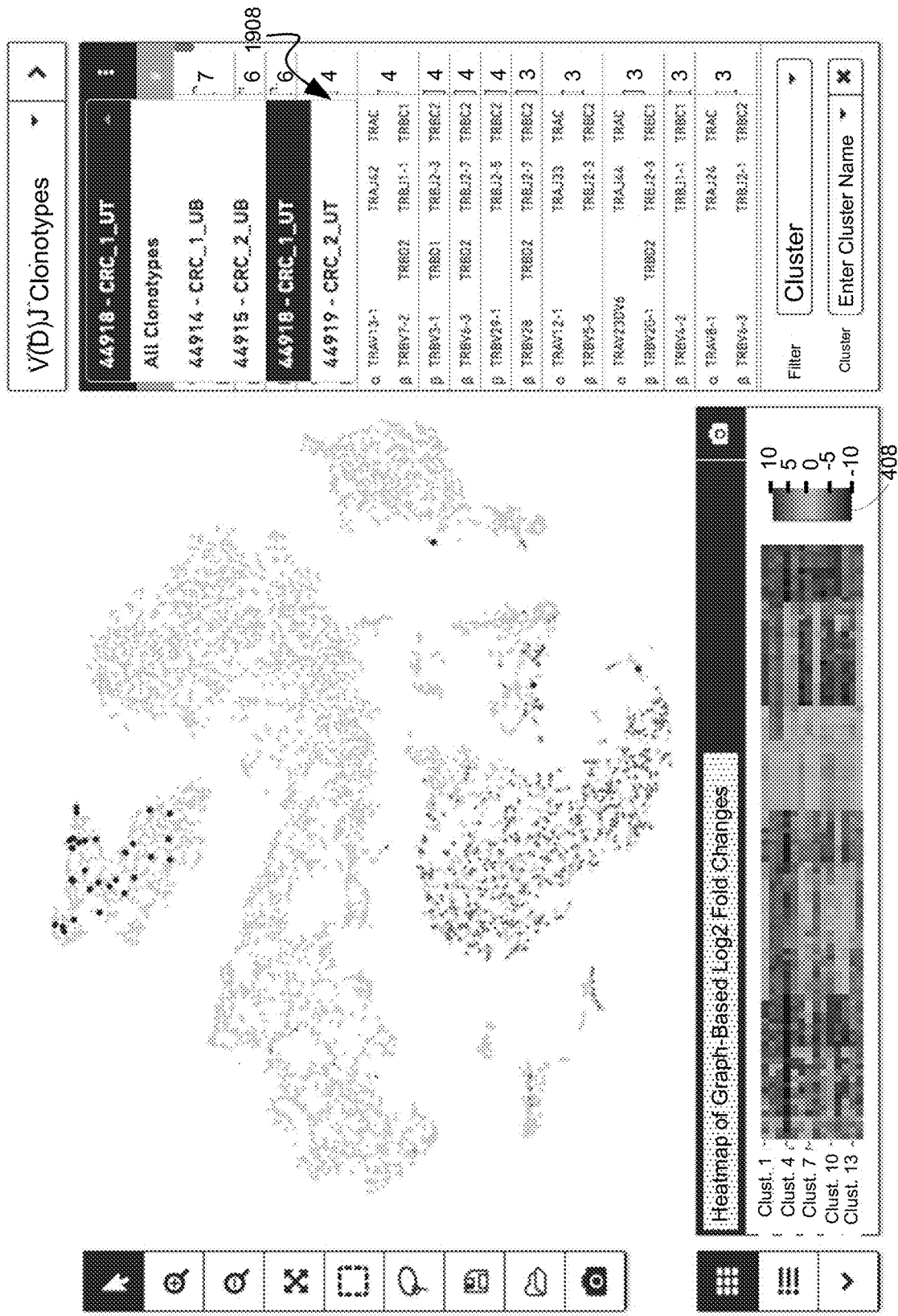
FIG. 22 illustrates the filtering of a clonotype list based on source V(D)J run, in instances where a clonotype dataset 1602B includes multiple V(D)J runs, or multiple clonotype datasets 1602B have been opened by a cell browser and indexed to the same discrete attribute value dataset based on common barcodes, in accordance with some embodiments of the present disclosure.

In some embodiments, the user is also able to filter a clonotype list by V(D)J run, in instances where a clonotype dataset 1602 includes multiple V(D)J runs, or multiple clonotype datasets 1602 have been indexed to a single discrete attribute value dataset 120 based on common barcodes (e.g., imported into a .cloupe workspace, as illustrated in FIG. 22). In FIG. 22, "44914-CRC_1_UB," "44914-CRC_2_UB," "44914-CRC_1_UT," and "44914-CRC_1_UT," each represent a separate V(D)J run disclosed in the section entitled "V(D)J Pipeline" below.

Figure 23:
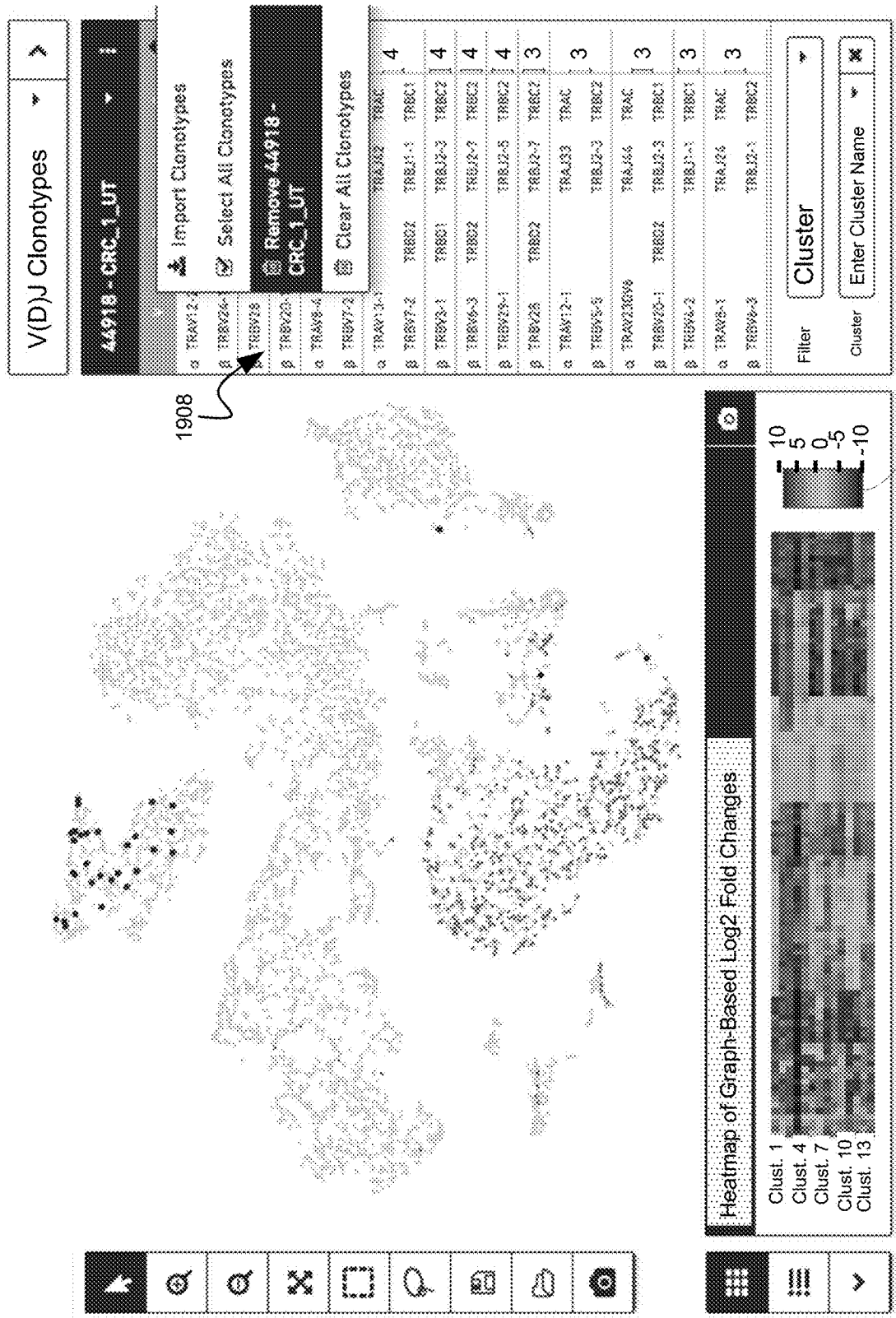
FIG. 23 illustrates a user interface for indexing a clonotype dataset to a discrete attribute value dataset, based on barcodes common to the two datasets, in accordance with some embodiments of the present disclosure.

In some embodiments, a user is able to import a clonotype dataset 1602 (e.g., a Loupe VDJ Browser file) into the cell browser 119 workspace (index respective clonotypes 1624 in a clonotype dataset 1602 to corresponding second entities 126 in a discrete attribute value dataset 120 on the basis of common barcodes) by selecting "Import Clonotypes" from the action menu illustrated in FIG. 23. In such embodiments, the cell browser 119 will prompt the user to select a clonotype dataset 1602 (e.g., Loupe VDJ Browser (vloupe) file)). If the barcodes for the clonotypes 1624 from the clonotype dataset 1602 sufficiently overlap the barcodes for the second entities 126 from the discrete attribute value dataset 120, the clonotype list will be amended. This is how the sample dataset illustrated in FIGS. 17-24 were made, by importing (indexing based on common barcodes) four clonotype datasets 1602 (.vloupes) to a discrete attribute value dataset 120. Once such importing (indexing) is done, a user can save the set of imported clonotype dataset 1602 by clicking on a save affordance. This saves the indexing of clonotype datasets 1602 (e.g., in the format of data structure 1602B of FIG. 16B) to the discrete attribute value dataset 120 based on common barcodes between clonotypes in the clonotype dataset 1602B and second entities 126 in the discrete attribute dataset 120 for future use.

Furthermore, as illustrated in FIG. 23, in some embodiments, it is possible remove a set of clonotypes or all clonotypes from the gene expression workspace.

V(D)J Pipeline. Referring to FIG. 16, in some embodiments, a respective barcode 1630 is deemed to be uniquely associated with a second entity 126 (e.g., single cell) if there exists within the clonotype dataset 1602 a contig 1628 that (i) is associated with the respective barcode 1630 and (ii) is supported by at least two unique molecular identifiers 1632 that each are supported by sequence reads 1634 in the dataset. In other words, each second entity 126 (e.g., cell) that is assumed to be represented by the clonotype dataset 1602 is supported within the clonotype dataset 1602 by a barcode 1630 for a contig 1628, where the contig, in turn, is supported by at least two different unique molecular identifiers 1632, where each such unique molecular identifier is, in turn, supported by sequence reads 1634 in the clonotype dataset 1602. For example, FIG. 19 displays various data from a clonotype dataset 1602. In particular, at a top level, nucleic acid sequences in the VDJ region of second entities 126 is organized by clonotypes 1624 in some embodiments.

In some embodiments, this sequence information, in the form of sequence reads 1634, is obtained using a droplet based single-cell RNA-sequencing (scRNA-seq) microfluidics system that enables 3' or 5' messenger RNA (mRNA) digital counting of thousands of single second entities 126 (e.g., single cells). In such sequencing, droplet-based platform enables barcoding of cells.

In some embodiments, the scRNAseq microfluidics system builds on the GemCode technology, which has been used for genome haplotyping, structural variant analysis and de novo assembly of a human genome. See Zheng et al., 2016 "Haplotyping germline and cancer genomes with high-throughput linked-read sequencing," Nat. Biotechnol. 34, pp. 303-311; Narasimhan et al., 2016, "Health and population effects of rare gene knockouts in adult humans with related parents," Science 352, pp. 474-477 (2016); and Mostovoy et al., 2016, "A hybrid approach for de novo human genome sequence assembly and phasing," Nat. Methods 13, 587-590, each of which is incorporated by reference, for a general description of GemCode technology. Such sequencing uses a gel bead-in-emulsion (GEM).

GEM generation takes place in a multi-channel microfluidic chip that encapsulates single gel beads at a predetermined fill rates, such as approximately 80%. For the clonotype datasets 1602 of the present disclosure, in some embodiments, a 5' gene expression protocol is followed rather than a 3' gene expression protocol. This provides full-length (5' UTR to constant region), paired T-cell receptor (TCR) transcripts or B-cell receptor (TCR) transcripts from a number of (e.g., 100-10,000) individual second entities 126 (e.g. lymphocytes) per sample. In some embodiments, as in the case of the 3' gene expression protocol described in Zheng et al., id., the 5' expression protocol includes partitioning the cells into GEMs. In particular, in some embodiments, single cell resolution is achieved by delivering the cells at a limiting dilution, such that the majority (~90-99%) of generated GEMs contains no single second entity 126 (e.g., lymphocyte), while the remainder largely contain a single second entity (e.g. lymphocyte). In some embodiments, upon dissolution of the single cell 5' gel bead in a GEM, oligonucleotides containing (i) a read 1 sequencing primer (e.g., ILLUMINA R1 sequence), (ii) a barcode 1630, (iii) a unique molecular identifier (UMI) 1632, and (iv) a switch oligonucleotide are released and mixed with cell lysate and a master mix that contains poly(dT) primers. Incubation of the GEMs then produces barcoded, full-length cDNA from poly-adenylated mRNA. After incubation, the GEMs are broken and the pooled fractions are recovered. In some embodiments, magnetic beads (e.g., silane beads) are used to remove leftover biochemical reagents and primers from the post GEM reaction mixture. As discussed above in the section entitled "Embodiments in which data is filtered on both discrete attribute values 124 and clonotypes 1624," the barcoded, full-length cDNA from poly-adenylated mRNA is pooled, amplified, and divided into at least two aliquots. In some embodiments, each of the two aliquots fully represents the relative expression levels of genes in the underlying second entities from which the full-length cDNA was reverse transcribed. In the embodiments in which the V(D)J pipeline is invoked in parallel to the discrete attribute value pipeline, one of these aliquots is subjected to V(D)J analysis as disclosed below, while the other aliquot is processed in accordance with the methods of as described in the section below entitled "Discrete attribute value pipeline.". In some embodiments, the barcoded, full-length cDNA from poly-adenylated mRNA is pooled, amplified, and divided into at least two aliquots, at least three aliquots, at least four aliquots, or more than five aliquots, each of which represents the relative expression levels of genes in the underlying second entities from which the full-length cDNA was reverse transcribed. In some embodiments, each of these aliquots is subjected to a different form of expression pipeline and advantageously because each of the cDNA is indexed with a barcode 1630 and a unique molecular identifier (UMI) 1632, the results of these pipelines can be mapped onto each other to provide novel insight into the expression patterns of first entities with respect to any number of filtering criteria, such as clustered gene expression patterns, clonotypes, cell type, that are determined by each such pipeline.

In the V(D)J pipeline, in some embodiments, the barcoded, full-length V(D)J segments in one of the aliquots described above is enriched by PCR amplification prior to library construction. In some embodiments, this was already done prior to forming the aliquot. In some embodiments, enzymatic fragmentation and size selection is used to generate variable length fragments that collectively span the V(D)J segments of the enriched receptor chains prior to library construction. As discussed above R1 (read 1 primer sequence) was added to the first entities during GEM incubation. P5 is added during target enrichment in accordance with the V(D)J pipeline. P7, a sample index and R2 (read 2 primer sequence) are added during library construction via end repair, A-tailing, adaptor ligation and implementation of the polymerase chain reaction (PCR). The resulting single cell V(D)J libraries contain the P5 and P7 primers used in Illumina bridge amplification. See the Internet, at assets.contentful.com/an68im79xiti/26tufAiwIO KCY A0ou2gCWK/8d313d2b126a7a1652d13810 73e720-15/CG000086 SingleCellVDJReagentKitsUserGuide RevA. pdf, last accessed May 18, 2017, pp. 2-4, which is hereby incorporated by reference. See also, "Multiplexed Sequencing with the Illumina Genome Analyzer System," copyright 2008, on the Internet at illumina.com/documents/products/datasheets/datasheet sequencing multiplex.pdf, last accessed May 18, 2017, hereby incorporated by reference, for documentation on the P5 and P7 primers. In some embodiments, the sequenced single cell V(D)J library is in the form of a standard ILLUMINA BCL data output folder. In some such embodiments, the BCL data includes the paired-end Read 1 (comprising the barcode 1630, the UMI 1632, the switch oligonucleotide, as well as the 5' end of a receptor chain cDNA) and Read 2 (comprising a random part of the of the same receptor chain cDNA) and the sample index in the i7 index read. In some embodiments, a computer program such as the 10X CELL RANGER analysis pipeline performs secondary analysis on the BCL data such as using the barcodes 1630 to group read pairs from the same second entities 126 (e.g., single cells), assemble full-length V(D)J segments in the form of contigs 1628, and thereby create the clonotype dataset 1602.

The multiple sequence reads 1634 with the same barcode 1630 form at least one contig 1628, and each such contig 1628 represents a chain (e.g., T-cell receptor α chain, T-cell receptor β chain, B-cell receptor heavy chain, B-cell receptor light chain, etc.) of a single second entity 126 (e.g. single cell). The contig consensus sequence 1626 for each of the contigs 1628 of a second entity are collectively used to determine the clonotype 1624 of the second entity. Stated differently, sequence reads 1634 are grouped by barcode 1630, and contigs 1628 are assembled by looking at sequence reads 1634 with the same UMI identifier 1632. A set of chain consensus sequences, including a CDR3 region, is created by analyzing the common bases in the contigs 1628. Second entities 126 with like CDR3 regions within these consensus sequences are grouped into clonotypes 1624.

In embodiments where the second entities 126 used for sequencing are T-cells or B-cells, each contig 1628 includes the third complementarity-determining region (CDR3) whose nucleotide sequence is unique to each T-cell clone or B-cell clone. In the case of T-cells, the CDR3 interacts with the peptide and thus is important for recognizing pathogen or autoantigen epitopes. The CDR3 region is a subset of the V-J region (indicated by the darker bar 918 in FIG. 9), spanning the V gene and J gene in T-cell receptor α chains and the V, D and J genes in T-cell receptor chains.

There are two subsets of T-cells based on the exact pair of receptor chains expressed. These are either the alpha (α) and beta (β) chain pair, or the gamma (γ) and delta (δ) chain pair, identifying the αβ or γδ T-cell subsets, respectively. The expression of the β and δ chain is limited to one chain in each of their respective subsets and this is referred to as allelic exclusion (Bluthmann et al., 1988, "T-cell-specific deletion of T-cell receptor transgenes allows functional rearrangement of endogenous alpha- and beta-genes," Nature 334, pp. 156-159; and Uematsu et al., 1988, "In transgenic mice the introduced functional T-cell receptor beta gene prevents expression of endogenous beta genes," Cell 52, pp. 831-841, each of which is hereby incorporated by reference). These two chains are also characterized by the use of an additional DNA segment, referred to as the diversity (D) region during the rearrangement process. The D region is flanked by N nucleotides which constitutes the NDN region of the CDR3 in these two chains. The CDR3 of each of the two receptor chains defines the clonotype 1624. For T-cells the CDR3 is in most contact with the peptide bound to the MHC. See Rudolph et al., 2006, "How TCRs bind MHCs, peptides, and coreceptors," Annu Rev Immunol 24:pp. 419-466, which is hereby incorporated by reference. For this reason, CDR3 sequences have been the main focus for immunological sequencing studies. See Yassai et al., 2009, "A clonotype nomenclature for T cell receptors," Immunogenetics 61, pp. 493-502, which is hereby incorporated by reference.

Human antibody molecules (and B-cell immunoglobulin receptors) are composed of heavy and light chains (each of which contains both constant (C) and variable (V) regions), which are encoded by genes on three loci: the immunoglobulin heavy locus (IGH@) on chromosome 14, containing the gene segments for the immunoglobulin heavy chain, the immunoglobulin kappa (κ) locus (IGK@) on chromosome 2, containing the gene segments for part of the immunoglobulin light chain, the immunoglobulin lambda (λ) locus (IGL@) on chromosome 22, containing the gene segments for the remainder of the immunoglobulin light chain. Each heavy chain and light chain gene contains multiple copies of three different types of gene segments for the variable regions of the antibody proteins. For example, the human immunoglobulin heavy chain region contains two Constant (Cμ and Cδ gene segments and 44 Variable (V) gene segments plus 27 Diversity (D) gene segments and 6 Joining (J) gene segments. See Matsuda et al., 1998, "The complete nucleotide sequence of the human immunoglobulin heavy chain variable region locus," The Journal of Experimental Medicine. 188 (11): 2151-62; and Li et al., 2004, "Utilization of Ig heavy chain variable, diversity, and joining gene segments in children with B-lineage acute lymphoblastic leukemia: implications for the mechanisms of VDJ recombination and for pathogenesis," Blood. 103 (12): 4602-9, each of which is incorporated by reference. The light chains also possess two Constant (Cμ and Cδ) gene segments and numerous V and J gene segments, but do not have D gene segments.

In general, the cell browser 119, when invoking the V(D)J pipeline disclosed in the present disclosure, can be used to analyze clonotype datasets 1602 prepared from T-cells or B-cells. In the case of T-cells, clonotyping identifies the unique nucleotide CDR3 sequences of a T-cell receptor chain, which constitute V, D, and J segments. In accordance with the systems and methods of the present disclosure, this generally involves PCR amplification of the mRNA obtained using the above described scRNAseq microfluidics system in which each GEM encapsulates a single cell, employing V-region-specific primers and either constant region (C) specific or J-region-specific primer pairs, followed by nucleotide sequencing of the amplicon.

The cell browser 119, when invoking the V(D)J pipeline disclosed in the present disclosure, is applicable to first entities 122 (e.g., genes) that code for the B-cells (the antibodies) and T-cells (the T-cell receptors). As discussed above in the case of T-cells, T-cells and B-cells get their diversity by a recombination process involving the V, D, J and C germ line regions. So each T-cell and B-cell encodes a unique clonotype 1624.

Sequence reads 1634 obtained from mRNA encoding all or portions of a cell receptor chain within an individual second entity 126 are used to derive a contig 1628 that includes the CDR3 region. Each of the contigs 1628 in a given second entity 126 will have a common barcode 1630 thereby defining the set of contigs in a given second entity 126 and, correspondingly, the set of CDR3 sequences for a given second entity 126. The CDR3 region across the set of contig consensus sequences 1626 for a given second entity 126 thereby determines the clonotype 1624 of the second entity 126. Thus clonotype dataset 1602 includes information about the frequency of clonotype 1624 occurrence across the plurality of second entities 126 represented in a clonotype dataset 1602. In the biological sample represented by the clonotype dataset 1602, each clonotype has some number of second entities 126 of a particular clonotype. In some embodiments, these clonotypes 1624 are sorted by frequency of clonotype occurrence. Thus, there may be multiple second entities represented by a single clonotype 1624 in the clonotype dataset 1602. As an example, in a particular biological sample represented by clonotype dataset 1602, there are 32 T-cells that have a first clonotype 1624, 9 T-cells that have a second clonotype 1624, 6 T-cells that have a third clonotype 1624, 6 T-cells that have a fourth clonotype 1624, and 5 T-cells that have a fifth clonotype 1624, where the first, second, third, fourth, and fifth clonotype are each different from each other. In this example, the first clonotype 1624 includes one contig type 1628 for a T-cell α chain and another contig type 1628 for a T-cell β chain. That is, each of the contigs for a T-cell α chain for the first clonotype 1624 have a same first CDR3 sequence, and each of the contigs for a T-cell β chain for the first clonotype 1624 have a same second CDR3 sequence in this example. By contrast, the second clonotype includes two contig types for a T-cell α chain and another two contig types for a T-cell β chain. That is, each of the contigs for a T-cell α chain for the second clonotype have either a first or second CDR3 sequence, and each of the contigs for a T-cell β chain for the second clonotype have a either a third or fourth CDR3 sequence.

A clonotype 1624 can have multiple chain consensus sequences, these chain consensus sequences are grouped into clonotypes for the reasons cited above. Two cells have the same clonotype if they share the set of same CDR3s for each distinct chain consensus sequence derived from its contigs.

In some embodiments, for each clonotype 1624, the clonotype dataset 1602 details each chain type represented by that clonotype. For instance, for a given clonotype 1624, there may be a single α chain type and a single β chain type meaning that all of the α chains for this clonotype have the same first CDR3 sequence and all of the β chains for this clonotype 306-1 have the same second CDR3 sequence In some embodiments, for each chain type represented in a clonotype 1624, the clonotype dataset provides an identifier for the V segment, an identifier for the diversity region (present in the case of T-cell β chains and δ chains, but not α chains and γ chains), an identifier for the J region, and an identifier for the C region. Two second entities 126 are deemed to have the same clonotype 1624 if their respective receptor chains have the same corresponding CDR3 sequences. Due to the heterozygous nature of the second entities being sampled, it is possible for a single second entity in the sample represented by the clonotype dataset 1602 to have up to two different α chains as well as up to two different β chains. In other words, due to the heterozygous nature of the second entities being sampled, it is possible for a single second entity in the sample represented by the clonotype dataset 1602 to have a first α chain with a first CDR3 sequence, a second α chain with a second CDR3 sequence, a first β chain with a third CDR3 sequence, and a second β chain with a fourth CDR3 sequence.

Discrete attribute value pipeline. As discussed above, in some embodiments, upon dissolution of the single cell 3' gel bead in a GEM, primers containing (i) an Illumina R1 sequence (read 1 sequencing primer), (ii) a 16 bp 10× Barcode, (iii) a 10 bp Unique Molecular Identifier (UMI) and (iv) a poly-dT primer sequence are released and mixed with cell lysate and Master Mix. Incubation of the GEMs then produces barcoded, full-length cDNA from poly-adenylated mRNA. After incubation, the GEMs are broken and the pooled fractions are recovered. Further, in some embodiments, silane magnetic beads are used to remove leftover biochemical reagents and primers from the post GEM reaction mixture. Full-length, barcoded cDNA is then amplified by PCR to generate sufficient mass for library construction. As discussed above, this amplified product is divided into aliquots at least one of which is subjected to the discrete attribute value pipeline.

In some embodiments, the discrete attribute value pipeline comprises enzymatic fragmentation and size selection in order to optimize the cDNA amplicon size prior to library construction. In some embodiments, R1 (read 1 primer sequence) are added to the molecules during GEM incubation. In some embodiments, P5, P7, a sample index and R2 (read 2 primer sequence) are added during library construction via End Repair, A-tailing, Adaptor Ligation and PCR. In some embodiments, the final libraries contain the P5 and P7 primers used in ILLUMINA bridge amplification. See the Chromium, Single Cell 3' Reagent Kits v2ser Guide, 2017, 10X Genomics, Pleasanton, California, Rev. B, page, 2, each of which is hereby incorporated by reference. Such a protocol produces ILLUMINA-ready sequencing libraries. In some embodiments, a single cell 3' library comprises standard ILLUMINA paired-end constructs which begin and end with P5 and P7. In some embodiments, the single cell 3' 16 bp 10×™ Barcode and 10 bp UMI are encoded in Read 1, while Read 2 is used to sequence the cDNA fragment. Sample index sequences are incorporated as the i7 index read. Read 1 and Read 2 are standard ILLUMINA sequencing primer sites used in paired-end sequencing. Sequencing a single cell 3' library produces a standard ILLUMINA BCL data output folder. The BCL data will include the paired-end Read 1 (containing the 16 bp 10×™ Barcode and 10 bp UMI) and Read 2 and the sample index in the i7 index read. In some embodiments, the Cell Ranger™ analysis pipelines perform secondary analysis and visualization. In addition to performing standard analysis steps such as demultiplexing, alignment, and gene counting, Cell Ranger™ leverages the Barcodes to generate expression data with single-cell resolution in the form of the discrete attribute value dataset 120. This data type enables applications including cell clustering, cell type classification, and differential gene expression at a scale of hundreds to millions of cells. Moreover, as discussed above, because the pipeline delivers this information by indexing discrete attribute value 124 from second entities on an individual second entity basis using barcodes, the data from such single cells can be combined with the data from other pipelines that make use of barcodes to track data from single cells, such as the V(D)J Pipeline described in section above entitled "V(D)J Pipeline" to provide unique biological insight into underlying molecular mechanisms associated with cell samples as disclosed above with reference to FIGS. 17 through 24.

While this section describes 3' chemistry and 3' protocol guide, in some embodiments, the discrete attribute value pipeline makes use of 5' chemistry and a 5' protocol when forming the nanoliter-scale Gel Bead-In-EMulsions (GEMs) and subsequent sequencing. Moreover, in those instances where the V(D)J pipeline is also invoked for a given biological sample, 5' chemistry is used rather than the disclosed 3' chemistry for the discrete attribute value pipeline so that the discrete attribute value data 124 overlaps with the V(D)J clonotype 1624 data.

In the embodiments of the present disclosure, techniques for analyzing biological samples are provided. The techniques involve acquiring a sample (e.g., a tumor biopsy, a sample of any tissue, body fluid, etc.) and processing the sample to acquire data from each cell in the sample for computational analysis. Each cell in the sample is barcoded, at a minimum, as discussed above. The acquired data is stored in a certain manner, for example, in specific data structure(s), for consumption by one or more processors (or processing cores) that are configured to access the data structures and to perform computational analysis such that biologically meaningful patterns within the sample are detected. The computational analysis and associated computer-generated visualization of results of the computational analysis on a graphical user interface allow for the observation of properties of the sample that would not otherwise be detectable. In particular, in some embodiments, each cell of the sample is subjected to analysis and characteristics of each cell within the sample are obtained such that it becomes possible to characterize the sample based on differentiation among different types of cells in the sample. For example, the clustering analysis, as well as other techniques of data analysis described above, reveal distributions of cell populations and sub-populations within a sample that would not be otherwise discernable. This leads to the discovery of novel cell types, or to the novel discovery of relationships between (A) aspects of the cellular phenotypes, such as genome (e.g., genomic rearrangements, structural variants, copy number variants, single nucleotide polymorphisms, loss of heterozygosity, rare variants), epigenome (e.g., DNA methylation, histone modification, chromatin assembly, protein binding), transcriptome (e.g., gene expression, alternative splicing, non-coding RNAs, small RNAs), proteome (e.g., protein abundance, protein-protein interactions, cytokine screening), metabolome (e.g., absence, presence, or amount of small molecules, drugs, metabolites, and lipids), and/or phenome (e.g., functional genomics, genetics screens, morphology), and (B) particular phenotypic states, such as absence or presence of a marker, participation in a biological pathway, disease state, absence or presence of a disease state, to name a few non-limiting examples. The identification of different classes of cells within the sample allows for taking an action with respect to the sample or with respect to a source of the sample. For example, depending on a distribution of cell types within a biological sample that is a tumor biopsy obtained from a subject, a specific treatment can be selected and administered to the subject.

In the embodiments of the present disclosure, a sample can include multiple second entities (e.g., cells), and the described techniques allow for the determination of first entities (e.g., mRNA sequences that map to a particular gene in a plurality of genes) having certain discrete attribute values (e.g., abundance) within each cell in the sample. For example, in some embodiments, each first entity in a plurality of first entities is a respective gene in a plurality of genes, and each discrete attribute value is a count of transcript reads within a second entity (e.g., a single cell) that map to a respective gene in the plurality of genes. In the described embodiments, as discussed above, the count of transcript reads can be in the form of a count of UMIs. In this way, gene expression per cell is determined and a discrete attribute value dataset is generated that includes discrete attribute values for each first entity in each second entity (cell).

Furthermore, the techniques in accordance with the described embodiments allow clustering and otherwise analyzing the discrete attribute value dataset so as to identify patterns within the dataset and thereby assign each cell to a type or class. As used in this context here, a class refers to a different cell type, a different disease state, a different tissue type, a different organ type, a different species, or different assay conditions or any other feature or factor that allows for the differentiation of cells (or groups of cells) from one another. The discrete attribute value dataset includes any suitable number of cell classes of any suitable type. Moreover, as discussed above, the described techniques (including barcoding and computational analysis and visualization) provide the basis for identifying relationships between cellular phenotype and overall phenotypic state of an organism that is the source of the biological sample from which the sample was obtained that would not otherwise be discernable.

In some embodiments, each first entity in a particular second entity (e.g., cell) in a plurality of second entities (e.g., a plurality of cells) is barcoded with a first barcode that is unique to the particular second entity. As discussed in detail above, each first entity in a particular second entity is barcoded such that a plurality of discrete attribute values identified for that first entity are then associated with the second entity and it is thus known which cell the first entities were obtained from. Moreover, to discriminate among reads that belong to different first entities within the same second entity (e.g., different genes within a single cell), individual first entities within the first entities within the same second entity are each "marked" with a unique molecular identifier (UMI). In this way, the barcoding and addition of UMIs allows for the reliable characterization of each second entity in a required manner.

Figure 38:
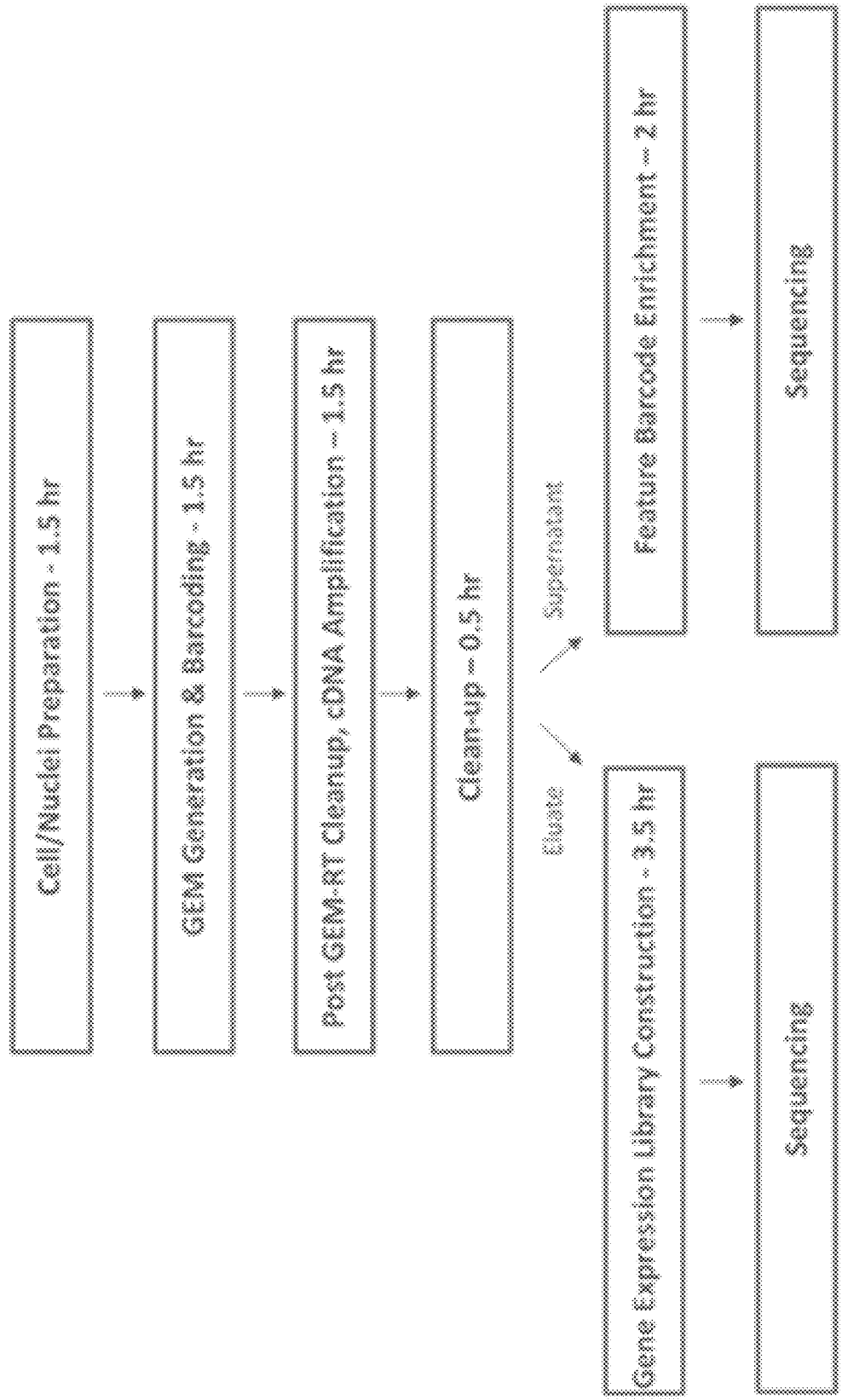
FIG. 38 illustrates a workflow for using a first set of bar codes to encode a plurality of first entities of a first class (e.g., gene expression) and a second set of bar codes to encode a plurality of first entities of a second class (e.g., a feature such as cell surface antibody abundance) using the same cells in accordance with some embodiments of the present disclosure.

In some embodiments, each first entity of a first type in a plurality of first entities of the first type is the gene expression count of a corresponding gene on a cell by cell basis. Moreover, in some such embodiments, additional entities beyond the first entities of the first type are measured. These additional entities are interchangeably referred to herein as "features" or "analytes" or "first entities of a second type" and such entities, like the first entities of the first type, are counted on a single cell basis. In this way, more than one type of first entity is monitored per cell in such embodiments. Accordingly, in some embodiments, in addition to determining discrete attribute values for each of a plurality of first entities of a first type in a second entity, discrete attribute values for each of a plurality of first entities of a second type in the second entity are determined. The first entities of the first type are different from the first entities of the second type. For example, in some embodiments, the first entities of the first type are counts of transcript reads (e.g. gene expression counts), whereas the first entities of the second type are so-called "non-gene" counts per cell such as, for example, counts of a bound antibody cell-surface marker, counts of clustered regularly interspaced short palindromic repeats (CRISPR) targeted guide RNAs, or counts of any other features (e.g., small molecule libraries, drugs, lipids) for which a separate library of bar codes is available. That is, the plurality first entities of the first class (e.g., gene expression counts) uses a first set of bar codes and the plurality first entities of the second class uses a second set of bar codes. By making use of different independent sets of bar codes for the plurality of first entities of the first class and the plurality of first entities of the second class, an amount of a first entity of the first class and an amount of a first entity of the second classes can be independently quantified in the same second entity (e.g., same cell) using the disclosed techniques and methods. One approach for accomplishing this is illustrated in FIG. 38. It should be appreciated, that the first entities of the second type can be any type of entities. For more information on the approach of FIG. 38, and for more information on barcoding assays that make use of one set of barcodes to track gene expression information and another set of barcodes to track a feature such as cell surface antibody abundance, CRISPR-mediated perturbations, etc., see U.S. Provisional Patent Application No. 62/629,602, entitled "Methods and Systems for Characterizing Multiple Analytes from Individual Cells or Cell Populations," filed Feb. 12, 2018, which is hereby incorporated by reference.

Accordingly, in some embodiments, first entities of a second type can be marked with a barcode (e.g., a UMI or another identifier) that is a different from a barcode (e.g., a UMI or another identifier) that is used to mark first entities of a first type. In this way, each second entity (e.g., a cell) can be unambiguously assigned at least one first entity of a first type and at least one first entity of a second type based on discrete attribute values for the first entity of the first type and discrete attribute values for the first entity of the second type. It should be appreciated that multiple features of a second entity (e.g., a cell) can be analyzed, such that discrete attribute values of first entities of more than two different types are identified.

In some embodiments, "raw" data acquired from sample processing hardware is transformed into a discrete attribute value dataset, which can be generated and stored in a suitable format. In embodiments that implement the cell browser 119, the discrete attribute value dataset is in a ".cloupe" format. A feature barcode pipeline is configured to count both gene expression per cell as well as non-gene features per cell.

As discussed above, some embodiments of the present disclosure provide a gene expression pipeline that involves acquiring data from sample processing hardware (e.g., the Chromium controller instrument (10X Genomics) and/or another system) and processing the data on a computer system that can be different from a visualization system (e.g., system 100 of FIG. 1A). The gene expression pipeline processes the acquired data so as to generate a data storage that is also referred to herein as a discrete attribute dataset. For example, in some embodiments, discrete attribute values (e.g., mRNA expression data, cell surface marker expression data, etc.) for each first entity in a single second entity (e.g., a single cell) are stored as a discrete attribute value dataset.

Each data point in a discrete attribute value dataset can be stored as a high-dimensional data point. In this way, in some embodiments, a feature-barcode matrix can be generated.

In some embodiments, similar to the embodiments described above, principal component analysis, or other forms of data reduction, such as subset selection (e.g., as disclosed in Hastie, 2001, *The Elements of Statistical Learning*, Springer, New York, pp. 55-57), discrete methods (e.g., as disclosed in Furnival & Wilson, 1974, "Regression by Leaps and Bounds," Technometrics 16(4), 499-511), forward/backward stepwise selection (e.g., as disclosed in Berk, 1978, "Comparing Subset Regression Procedures," Technometrics 20:1, 1-6), shrinkage methods (e.g., as disclosed in Hastie, 2001, *The Elements of Statistical Learning*, Springer, New York, pp. 59-66), ridge regression (e.g., as disclosed in Hastie, 2001, *The Elements of Statistical Learning*, Springer, New York, pp. 59-64), lasso techniques (e.g., as disclosed in Hastie, 2001, *The Elements of Statistical Learning*, Springer, New York, pp. 64-65, 69-72, 330-331), derived input direction methods (e.g., principal component regression (PCR), partial least squares (PLS), etc. as disclosed, for example, in Viyayakurma and Schaal, 2000, "Locally Weighted Projection Regression: An O(n) Algorithm for Incremental Real Time Learning in High Dimensional Space, Proc. of Seventeenth International Conference on Machine Learning (ICML2000), pp. 1079-1086), or combinations thereof, are used to reduce the dimensionality of the data down to a certain number of dimensions (e.g., ten dimensions, or another number of dimensions).

In some embodiments, the feature counts per cell are stored as sparse matrices in compressed sparse column (CSC) and compressed sparse row (CSR) formats. Furthermore, each row in the feature-barcode matrix includes additional metadata, which can be automatically generated by the pipeline hardware and/or acquired based on user input.

In some embodiments of the present disclosure, a data structure storing the feature-barcode matrix is accessed by processing core(s) 102 of the visualization system 100 or by another computing device (e.g., a remote computing device or server) and clusters can be detected in the data (discrete attribute values) stored in the format of this matrix. Any of the techniques described above, or a combination of these techniques, can be implemented for the clustering. For example, in some embodiments, the clustering of the discrete attribute values comprises hierarchical clustering, agglomerative clustering using a nearest-neighbor algorithm, agglomerative clustering using a farthest-neighbor algorithm, agglomerative clustering using an average linkage algorithm, agglomerative clustering using a centroid algorithm, or agglomerative clustering using a sum-ofsquares algorithm. In some embodiments, the clustering includes application of a Louvain modularity algorithm, k-means clustering, a fuzzy k-means clustering algorithm, or Jarvis-Patrick clustering. The clustering can be performed on the entire dataset of the feature-barcode matrix, or using only a portion of the dataset. In some embodiments, the portion from the dataset can be selected for clustering based on user input. Furthermore, in some embodiments, the portion from the dataset can be selected for clustering automatically—e.g., based on certain characteristics of the features in the dataset.

Figure 25A:
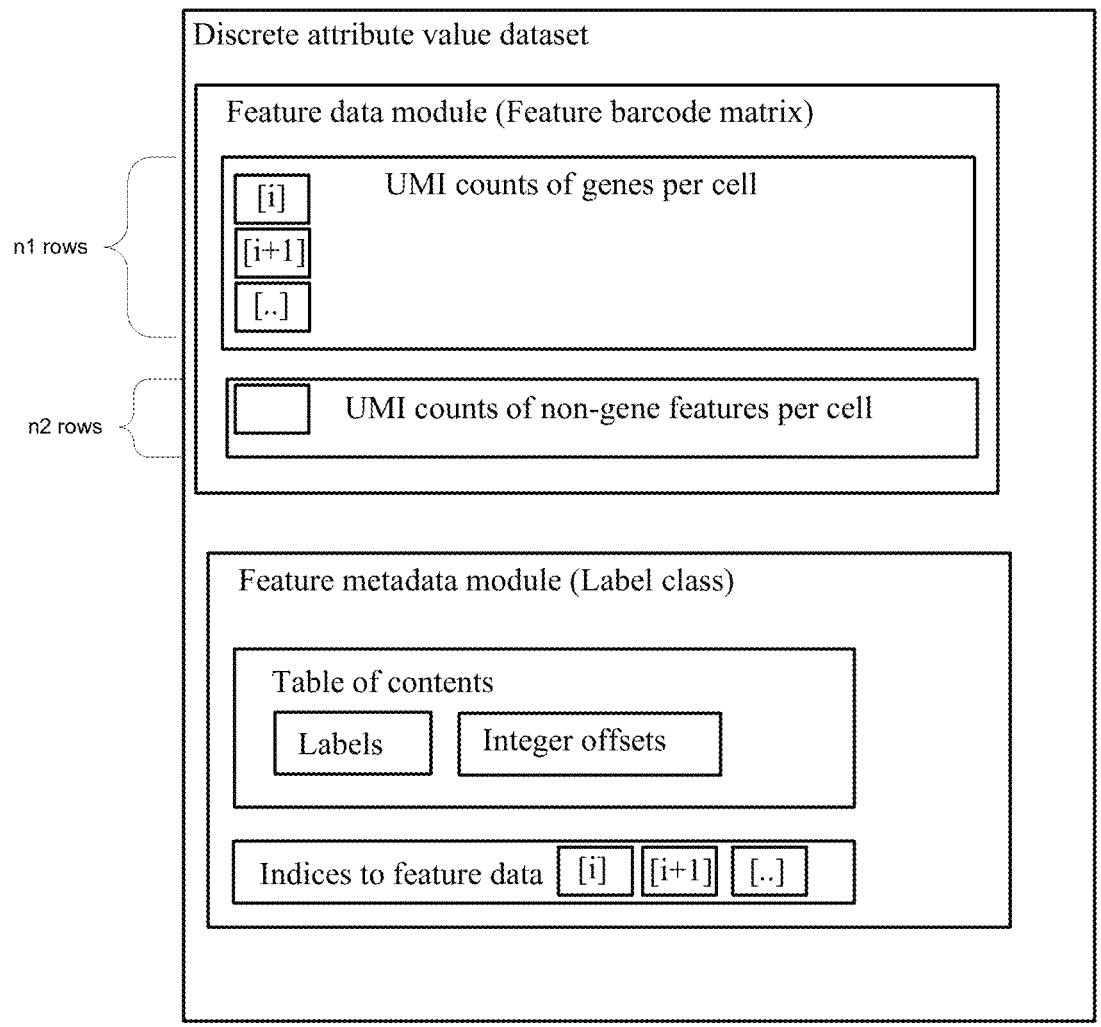
FIG. 25A is a block diagram illustrating a discrete attribute value dataset in accordance with some embodiments of the present disclosure.

In some embodiments, the .cloupe file stores feature data (read counts) and feature metadata separately, and the feature metadata is stored in a serialized data structure, as shown in FIG. 25. Such a data storage format increases computational efficiency. In particular, FIG. 25 illustrates a discrete attribute dataset for a gene expression pipeline, capable of counting gene and non-gene features per cell, that includes a feature data module storing UMI counts per gene per cell and UMI counts of non-gene features (e.g., bound antibodies) per cell. A feature metadata module, also referred to herein as a "label class," identifies a type of each row the matrix. In some embodiments, as shown in FIG. 25, the feature metadata module is stored on disk as two entities—a table of contents and an indices module. The table of contents includes a labels module (which can store, e.g., an array of labels) and an integer offsets module (which can store, e.g., an array of integer offsets). The indices module can be in the form of a continuous array of indices, where each index in the array (e.g., indices i, i+1, etc.) refers to indices of rows in the feature data storage.

For example, in some embodiments, the feature data module includes an antibody dataset having n1 of rows representing a number (n1, in this example) of UMI counts per gene per cell and subsequent n2 rows of representing a number (n2, in this example) of UMI counts of certain one or more bound antibodies in each second entity (e.g., cell). As an example, the antibody dataset can include 20,000 rows representing UMI counts per gene per cell (e.g. n1=20,000) and subsequent 17 rows representing the UMI counts of the bound antibody per each cell (e.g. n2=17). In this example, the table of contents defines the labels as "Labels: ["Gene", "Antibody"]" and the integer offsets as "Offsets: [0, 20000]." The integer offsets indexes into a contiguous array of 20,017 feature row indices in the indices module. The range of feature row indices corresponding to genes starts at array position 0, and the indices for the antibody start at the position 20,000. The indices module, in this example, can be integers from 0 to n1-1 in the ascending order, where n1 is the number of rows in the feature data module. The table of contents module can be stored in any suitable format. For example, in some embodiments, it can be a compressed JSON string and information stored in the table of contents can be in the form of CSC and CSR indices and data. Such approaches increase computational efficiency. For instance, representation of labels for two different types of first entities in this manner improves the computational efficiency of visualization system 100, in part, by reducing the amount of data that needs to be processed in order to visualize the data for the first entities of the first type and the first entities of the second type.

In some embodiments, a feature metadata module stores data in a sparse manner. Continuing with the above example, a feature metadata module (a label class) representing a "control type" tag for the 17 antibody rows includes the following information:

{Labels: ["Positive", "Negative"],
Offsets: [0, 14]}
Further, the indices array will be as follows:
array: [20000 20001 20002 20004 20005 20006 20007 20008 20009 20011 20012 20014 20015 20016 20003 20010 20013]

In this example, the negative control array indices in the indices module start at a zero-based position 14 in the array (e.g., the offset for the negative control antibodies information is 14). Thus, starting from the 15$^{th}$ entry into the array of the indices module, indices 15-17 (20003, 20010, and 20013) are indices of respective rows in the feature data module, where these rows therefore include data on negative control antibodies.

In some embodiments, an assay for transposase accessible chromatin (ATAC) pipeline is provided that analyzes accessible regions of a genome. In such embodiments, a plurality of discrete attribute values for each first entity of a second type (e.g., a feature other than gene expression) includes counts of transposase accessible chromatin (ATAC) peak features. ATAC with high-throughput sequencing (ATAC-seq) maps chromatin accessibility by probing for DNA accessibility using hyperactive Tn5 transposase. Tn5 transposase inserts sequencing adapters into accessible regions of chromatin. See Buenrostro et al., 2015, "ATAC-seq: A Method for Assaying Chromatin Accessibility Genome-Wide," Curr Protoc Mol Biol. 109:21.29.1-9. In the described embodiments, however, single cell ATAC technique are provided that allow for the acquisition of ATAC data from each cell in a sample. The chromatin profiling of numerous second entities (e.g., tens of thousands of single cells) in parallel allows workers to see how chromatin compaction and DNA-binding proteins regulate gene expression at high resolution. For more details on such single cell ATAC techniques that are used to obtain the ATAC data, see U.S. patent application Ser. No. 15/842,550, entitled "Single Cell Analysis of Transposase Accessible Chromatin," filed Dec. 14, 2017, which is hereby incorporated by reference.

For the ATAC dataset, in typical embodiments, there are no measures of gene expression. The primary entity of rows in the matrix for ATAC data is fragments (or UMIs) per called peak, where the peak corresponds to a genomic region of accessible chromatin. For ATAC data, the matrix contains counts of fragments in peaks instead of gene expression. ATAC matrices will also contain aggregate rows as described below. As such, the ATAC pipeline generates a feature-barcode matrix, identifies clusters based on the feature-barcode matrix, identifies significant features (using, e.g., a principal component analysis or other forms of data reduction such as those disclosed herein), and computes a 2-D t-SNE projection based on the significant elements of the matrix. Because the ATAC pipeline performs a type of analysis that is different from the pipelines discussed above, different types of graphical user interface components are needed to display the results of the ATAC pipeline, as discussed below.

In some embodiments, an ATAC pipeline identifies distinct peak regions, which can be regions encompassing from hundreds to thousands of nucleotides. In these regions, fragments derived from open chromatin sites can be detected. In some embodiments, similar to the gene expression pipeline, the ATAC pipeline emits a .cloupe file for consumption by the cell browser 119. In this way, the ATAC pipeline is configured to count non-gene features per cell. A feature metadata module (a label class) can be used to associate ATAC peak feature rows with nearby promoter genes, to encode user-specified tags, such as, e.g., a gene target of CRISPR guide RNA, whether an antibody is a positive or negative control, a source reference genome of a gene feature in the feature data module (matrix), etc.

In some embodiments, a visualization system is provided that is configured to present a graphical user interface on a display of a computing device. In some embodiments, a graphical user interface, also referred to herein as cell browser 119, is configured to receive data acquired using the ATAC assays (ATAC dataset) or a dataset that includes gene expression as well as feature abundance. Regardless, prior to being accessed by the cell browser, the data is transformed into a format suitable for representation of the data on the graphical user interface. The data is presented on the graphical user interface in the format that allows manipulating the data based on user input or in other manner. One or more patterns within the data can be detected by the computing hardware executing the cell browser. The graphical user interface is configured to display the data and various patterns in the manner that allows revealing previously unknown groups or patterns within the data (e.g., within cells from a biological sample). Moreover, the graphical user interface is configured to receive instructions (e.g., user input) in response to which new patterns can be defined within the data. In some embodiments, user-specific tags are not encoded into the ATAC dataset (e.g., the ATAC version of a feature-barcode matrix). In alternative embodiments, user-specific tags are encoded into the ATAC dataset. In some embodiments, rather than making use of user-specific tags, the feature metadata module encodes nearby promoters, nearby genes, peak region function, transcription factor motifs, and unique transcript IDs. In some embodiments, user-specific tags are encoded in the matrix representing the dataset that includes both gene expression (first entity of the first class) as well as feature (first entity of the second class) abundance.

Figure 26:
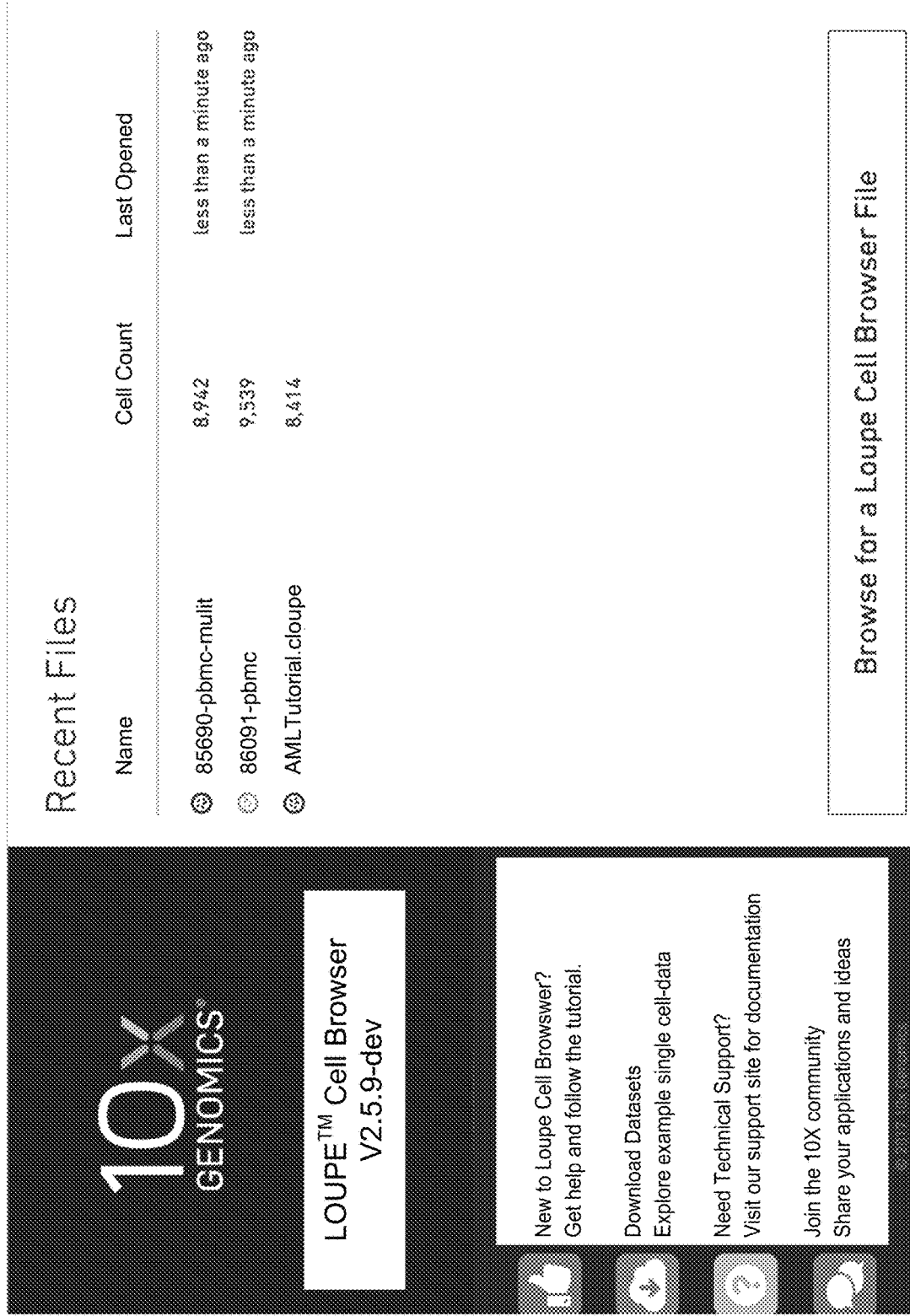
FIG. 26 illustrates a user interface for acquiring a dataset in accordance with some embodiments.

As discussed above, in some embodiments, a cell browser 119 is executed in conjunction with display 108 of a visualization system 100. FIG. 26 illustrates an example of cell browser 119. In some embodiments, for representation and manipulation of ATAC peaks data, the user interface includes certain features specific to the ATAC peak data. In some embodiments, the .cloupe file includes an identifier indicating whether the .cloupe file includes gene expression data (e.g. in the form of discrete attribute value dataset 120) or whether the .cloupe contains ATAC peaks. For example, in FIG. 26, an icon (blue, in this example) to the left of the "85690-pbmc-multi" file representation indicates that the 85690-pbmc-multi file includes gene expression data. An icon (green, in this example), to the left of the "86091-pbmc" file representation indicates that the 86091-pbmc file includes ATAC data (which may be in addition to gene expression data within the dataset). It should be appreciated that the representations in FIG. 26 are shown by way of example only, as any other indicators can be used to differentiate between data sets including gene expression data and data sets including both gene expression and ATAC data. Moreover, the disclosure is not limited to the use of the .cloupe file format.

Figure 27:
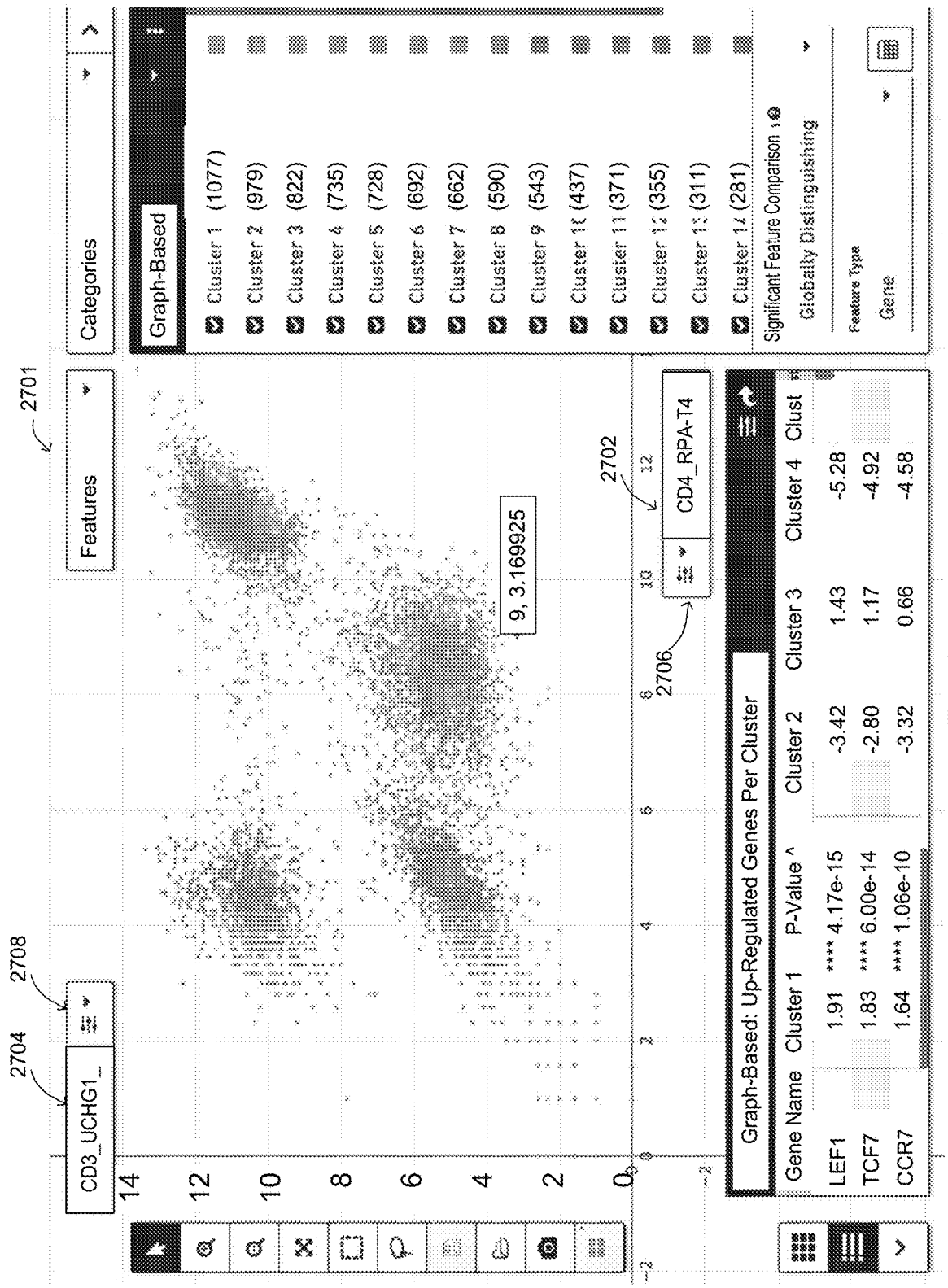
FIG. 27 illustrates an example of a user interface for selectively presenting information from an antibody dataset, where a $\log_2$-$\log_2$ representation of the CD3 surface marker antibody expression against the CD4 surface marker antibody expression is displayed, in accordance with some embodiments of the present disclosure.

The cell browser can present information in various formats. In some embodiments, as shown in FIG. 27, relationships between one first entity of a first type (e.g., CD3) and another first entity of the first (e.g., CD4 surface marker antibody) is presented. As shown in this example, an input icon 2701 is used to receive user input indicating selection of an option (shown by way of example as "Features," as any other suitable name for this option can be used) to display a representation of relationships between two or more features.

Figure 31A:
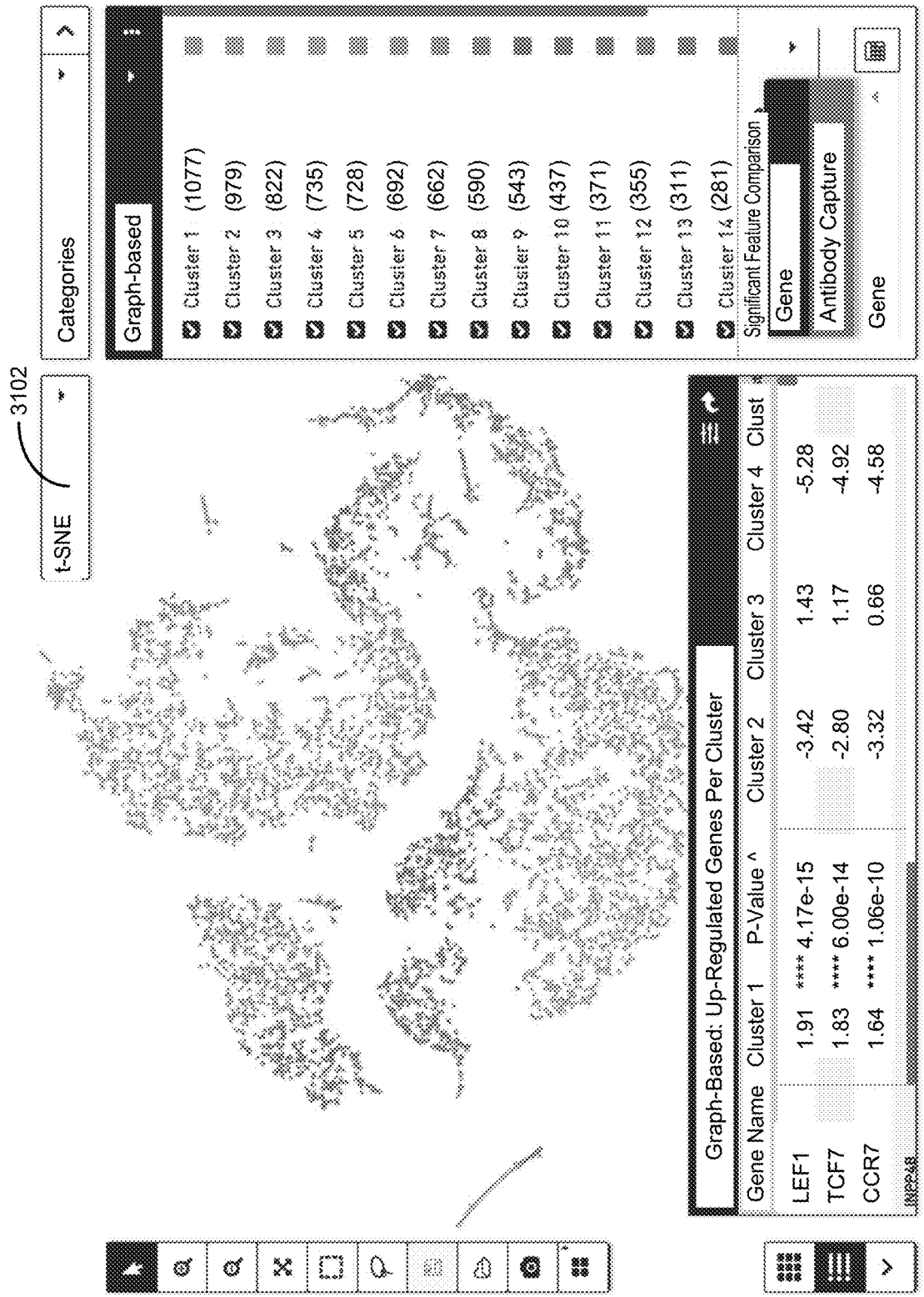
FIGS. 31A and 31B illustrate an example of a user interface for selectively presenting information from an antibody dataset, in accordance with some embodiments of the present disclosure.

Turning to FIG. 31A, prior to presentation of the graph shown in FIG. 31A, data in the form of a plurality of first entities of a first class (e.g., gene expression) and a plurality of first entities of a second class (e.g., a feature, such as cell surface antigen abundance) have been acquired for the same plurality of entities of a second class. Then, two types of clustering are performed. The first clustering clusters based on the values for the first entities of the first class as discussed above. That is, as discussed above, the second entities (e.g., cells) are clustered based on gene expression to arrive at a set of clusters of second entities. Separate and apart from this first clustering, a second clustering is performed that is based on the values for the first entities of the second class. Moreover, in a manner similar to that discussed above, this clustering is dimension reduced and can be visualized in two dimensions using an algorithm such as t-distributed stochastic neighboring entities (t-SNE). What is shown in FIG. 31A is the t-SNE visualization of the second entities based on the measured values, for each second entity, for the first entities of the first class (the expression data, not the feature data). Thus, in FIG. 31A, second entities that have similar abundance values for the first entities of the first class are near each other in FIG. 31A, and second entities that have dissimilar abundance values for the first entities of the first class are far apart from each other in FIG. 31A. Advantageously, in addition to the observed two-dimensional clustering based on similarity in abundance values for the first entities of the first class, each respective point (representing a single second entity in the plurality of second entities) is colored based on the cluster of second entities the respective second entities belong to, based on the observed abundance values for the first entities of the first class. As illustrated in FIG. 31A, there are more than 14 such clusters, meaning that when the plurality of second entities (e.g., cells) were clustered based on abundances of the first entities of the first class (e.g., gene expression), more than 14 such clusters were formed. These clusters are illustrated in the two-dimensional plot of FIG. 31A, with each cell in the plot been colored based on which gene expression cluster it falls into (abundance values for the first entities of the first class), and the coordinates of each point represent a corresponding cell's relative similarity /dissimilarity to other cells based on abundance values for the first entities of the first class in such cells. As such, in some implementations of the cell browser, a default representation is a t-SNE projection discussed above.

Figure 31B:
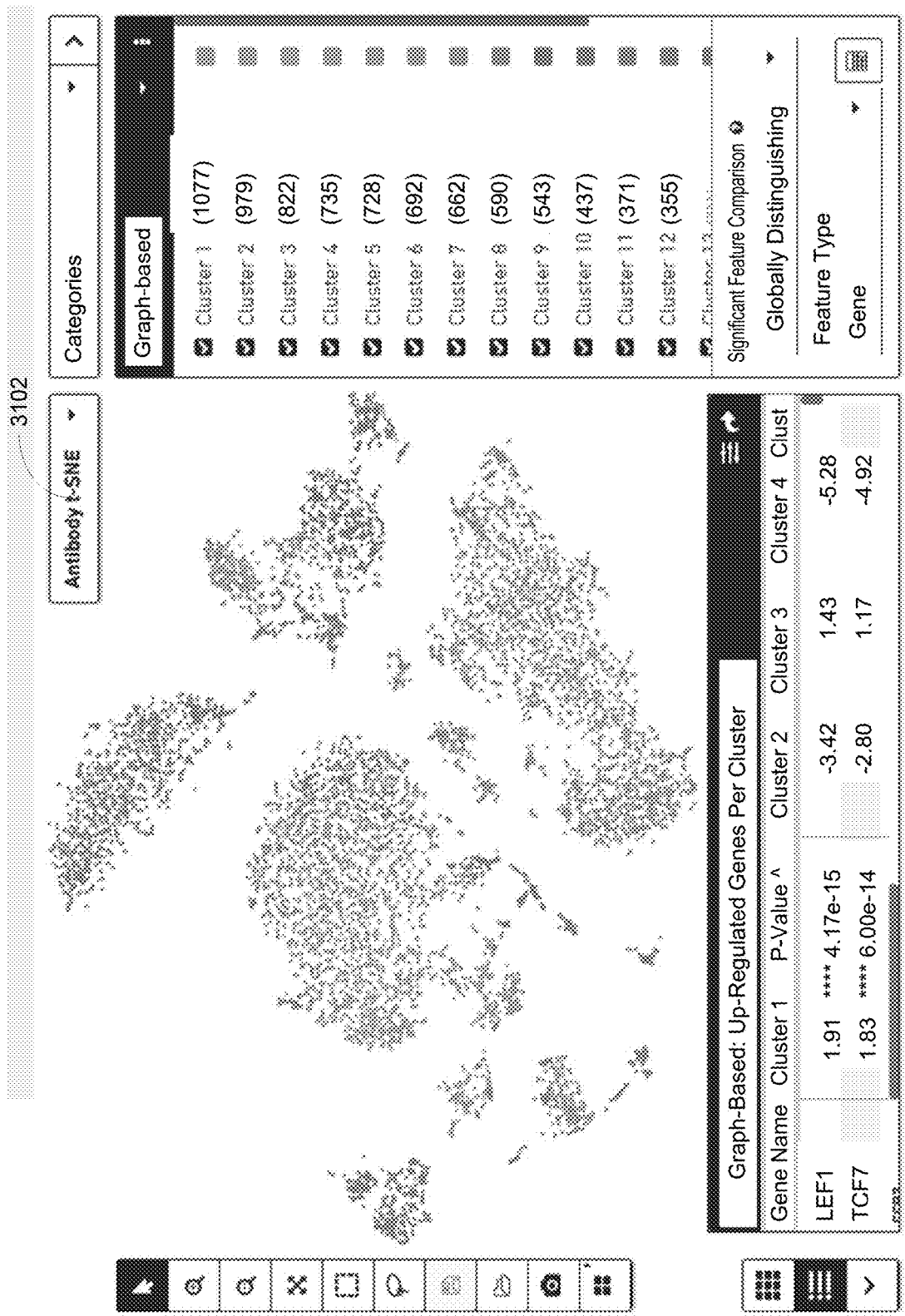

In FIG. 31A, affordance 3102 can be changed to "Antibody t-SNE," rather than "t-SNE." Responsive to this change in affordance 3102, each point on the plot is shifted so that is represents the t-SNE values based on the first entity of the second class rather than first entity of the first class as illustrated in FIG. 31B, where the second entities have now been clustered using t-SNE using the feature values, and where each respective second entity remains colored based on which expression cluster it is in. Thus, in this situation, second entities that have similar feature values for the first entities of the second class are near each other in the plot, and second entities that have dissimilar abundance values for the first entities of the second class are far apart from each other. Advantageously, in addition to the observed two-dimensional clustering based on similarity in abundance values for the first entities of the second class, each respective point (representing a single second entity in the plurality of second entities) remains colored based on the cluster of second entities the respective second entities belong to, based on the observed abundance values for the first entities of the first class.

Referring back to FIG. 27, in some embodiments, rather than using t-SNE and the abundance values of the first entities of the first or second class to determine position of second entities in the graph as in FIGS. 31A and 31B, affordance 2704 is used to select a particular first entity of the second class (e.g., CD3 surface marker antibody expression) and a particular first entity of the second class (e.g., CD4 surface marker antibody expression) and the second entities are plotted by their values for these two first entities. For example, if a cell has a value of 8 for CD3 and a value of 6 for CD4 surface marker antibody in FIG. 27, the cell is plotted at (x,y) position (8,6). Further, the representation of the cell at position (8,6) is colored based on which expression cluster the cell belongs to e.g., cluster 8, green). As such, interactive input menu icon (affordance) 2702 is used to receive user input indicating selection (e.g., from an autocomplete or drop-down menu) of a particular first entity of the second class (feature) to be used as a basis for plotting on the x-axis, and an interactive input menu icon (affordance) 2704 is used to receive user input indicating selection (e.g., from an autocomplete or drop-down menu) of a feature for display on the y-axis. In the example of FIG. 27, information on the CD4 surface marker antibody expression is selected for display on the x-axis and information on the CD3 surface marker antibody expression is selected for display on the y-axis.

In addition to the feature menu icons (affordances) 2702, 2704, respective scale menu icons 2706, 2708 are rendered, which can receive input indicating selection of a scale (e.g., a linear scale, $log_2$ scale, or another type of a scale) for representation of the respective axis. Furthermore, in the user interface as shown in FIG. 27, as well as in similar interfaces presented when the features relationship is displayed, clonotypes can be emphasized. For example, since each point in the graph of FIG. 27 represents a second entity (e.g., a cell) the user can select to color or otherwise highlight particular clonotypes with particular colors or other indicia. As another example, the user can select to display cells of only certain (white listed) clonotypes and not display cells of other (black listed) clonotypes.

Moreover, in the user interface as shown in FIG. 27, as well as in similar interfaces presented when the features relationship is displayed, gene expression information may be superimposed.

Moreover, in the user interface as shown in FIG. 27, as well as in similar interfaces presented when the features relationship is displayed, new clusters can be created from the feature plot, similar to the ways described above. For example, a lasso selection tool or another appropriate tool can be used to create a new cluster based on user input specifying creation of such cluster. In addition, in such a user interface, a relative frequency of a gene or a feature can be displayed by representing the frequency of the gene or the feature against the sum of all genes or features of that particular type, which can be stored in the .cloupe file, as discussed in more detail below.

Figure 28:
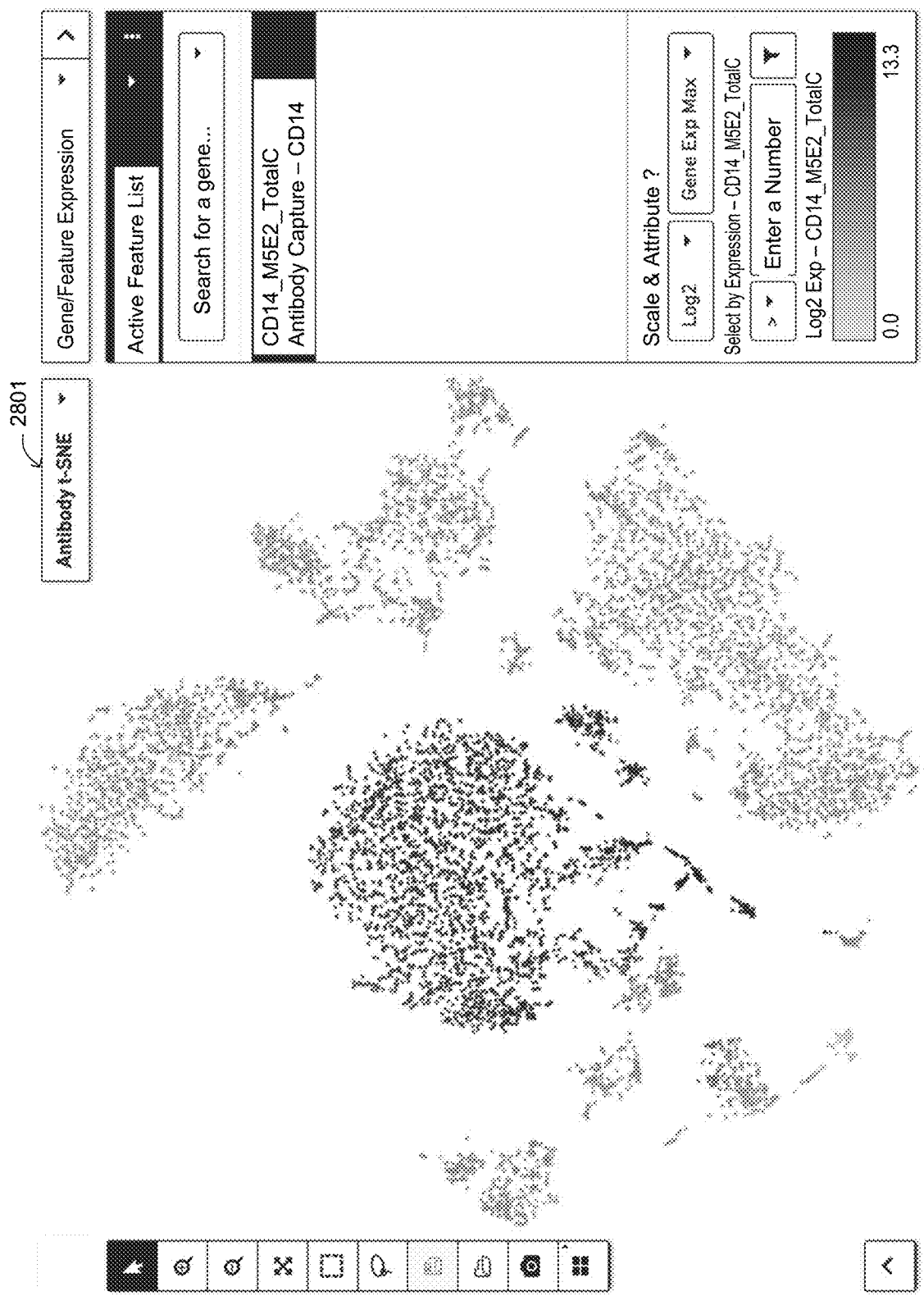
FIG. 28 illustrates an example of a user interface for selectively presenting information from an antibody dataset, where an "Antibody t-SNE" option is shown selected, indicating a selection of the corresponding projection, in accordance with some embodiments of the present disclosure.

In some embodiments, the ATAC pipeline and gene expression pipeline are configured to generate clusters and/or t-SNE projections based on subsets of features in the feature-barcode matrix (also referred to as a discrete attribute dataset). For example, in one embodiment, when an antibody dataset is being explored, discrete attribute values related to genes in the feature-barcode matrix are used to determine clusters and create a t-SNE projection, and discrete attribute values related to surface marker antibody features are used to construct a different projection. As shown in FIG. 28, in some embodiments, a projection selector menu 2801 receives input indicating selection of an "Antibody t-SNE" projection. To generate this projection, the plurality of first entities of the second class, here antibody abundance, is dimension reduced using, for example, principal component analysis, across the cells (second entities) of the dataset to form reduction components (e.g., principal components) and these reduction components are further reduced by t-SNE to generate the two dimensional plot of FIG. 28 in which cells with similar abundance values for the plurality of first entities of the second class are clustered together and cells with dissimilar abundance values for the plurality of first entities of the second class lie further apart from each other. Moreover, the plotted cells are color coded by the log2 expression of CD14. While CD14 is used in this example, it will be appreciated that the plotted cells can be color coded by an abundance of any one of the plurality of first entities of the first class or any one of the plurality of first entities of the second class, among other possibilities. By comparison, the cells in FIG. 27 were color coded by their expression cluster, where expression cluster was determined by clustering the cells by the abundance value of first entities of the first class across the plurality of cells.

To generate additional projections in the pipeline, in some embodiments a configuration file is specified that identifies the barcode sequence corresponding to a feature barcode, its type, as well as additional metadata. It will be appreciated that such feature barcodes are for the plurality of first entities of the second class and thus are separate and apart from the barcodes for the plurality of first entities of the first class. An example of a line from an antibody configuration file, which represents one form of feature, can be as follows:

id, name, read, pattern, sequence, feature_type
CD3, CD3_UCHT1 TotalC, R2, /\NNNNNNNNNN(BC) NNNNNNNNN CTCATTGTAACTCCT, Antibody Capture The first two columns are the feature ID ("id") and display name "name" that will propagate to the cell browser 119, the read and pattern columns indicate to the pipeline how to extract the barcode sequence from the raw sequencing read, the sequence column specifies the identifying sequence per feature, and the "feature_type" column specifies the feature type. For such a configuration file, all features of type "Antibody Capture" are combined to create an additional projection. If the configuration file had multiple feature types, the pipeline can generate a projection for each distinct feature type. The additional projections can be stored in the same format as the t-SNE projection from versions of cell browser 119 discussed above.

Figure 25B:
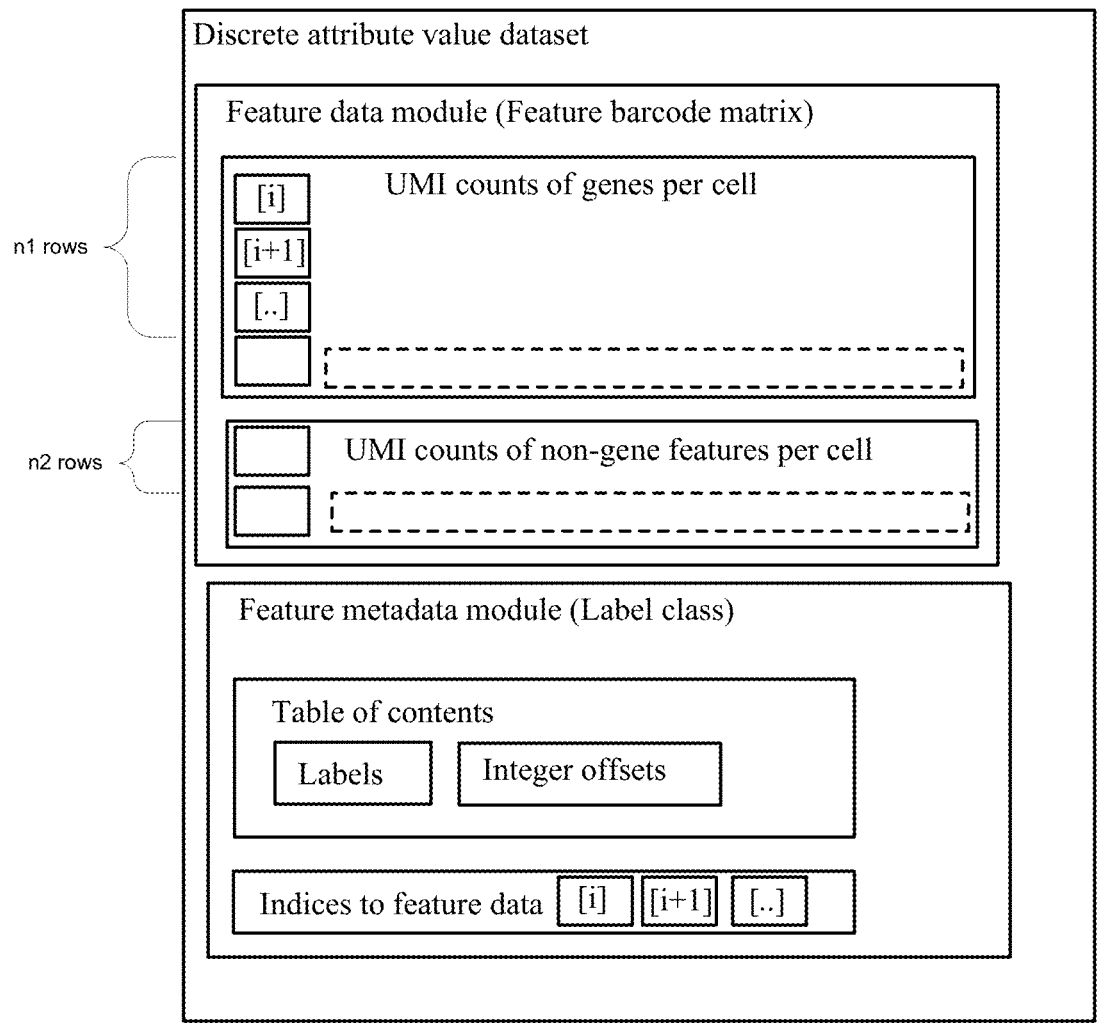
FIG. 25B is another block diagram illustrating the discrete attribute value dataset of FIG. 25A, where aggregate rows are generated and stored in the feature data module, in accordance with some embodiments of the present disclosure.

In some embodiments, aggregate features are generated by combining features of the same or similar type. For example, referring back to FIG. 25A, additional rows can be generated based on existing rows in the feature data, and these additional rows can be added to the feature data module. FIG. 25B illustrates schematically such additional rows which are shown with a dashed line. In some implementations of the present disclosure, feature rows with similar metadata are combined to generate additional feature rows. For example, referring to the example above where the feature data module includes 20,000 gene data rows per cell and 17 antibody data rows per cell, an aggregate gene data row can be generated by combining the 20,000 gene data rows and an aggregate antibody data row can be generated by combining the 17 antibody data rows. In some embodiments, when each row includes respective gene counts per cell or antibody counts per cell, the respective gene counts and antibody counts can be summed to generate respective aggregate gene count row and aggregate antibody count (or some other feature) row. It should be appreciated, however, that the gene data rows, antibody data rows, or rows storing data for any other types of features can be combined in other ways that can be different from a summation operation. Furthermore, in some cases, a portion of the rows (e.g., in the above example, less than 20,000 gene data rows) in the feature data module can be combined. Regardless of the way in which multiple rows having similar metadata are combined, the resulting aggregate rows can be stored in compressed form (e.g., compressed sparse row (CSR) and compressed sparse matrix (CSC) formats). This advantageously improves computer efficiency. The locations of the aggregate rows are stored in the feature metadata module.

Figure 29:
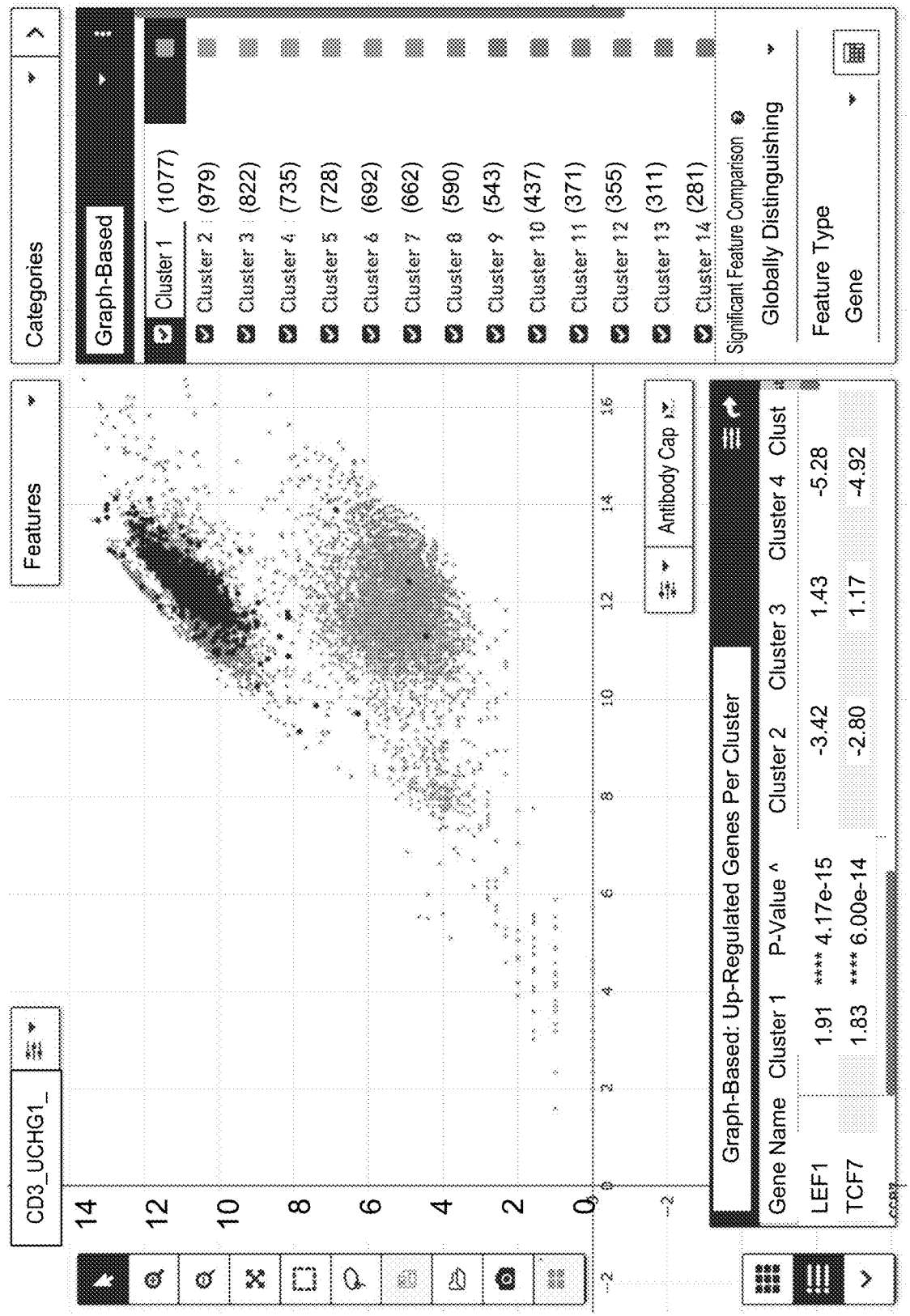
FIG. 29 illustrates an example of a user interface for selectively presenting information from an antibody dataset, where a $\log_2$-$\log_2$ representation of the CD3 surface marker antibody expression against an antibody feature aggregate is displayed, in accordance with some embodiments of the present disclosure.

In some embodiments, aggregating feature rows having similar metadata (e.g., counts of a particular feature per cell) allows for the derivation of a normalized, relative expression for that particular feature. FIG. 29 illustrates a $log_2$ fold change representation of a CD3 antibody expression plotted on the y-axis against a $log_2$ fold change representation of the aggregate antibody feature data (stored as a row in the future data module) on the x-axis. Such a representation improves a user experience by revealing distinct distributions of CD3 antibody expression per cell. The $log_2$ fold change/log 2 fold change representation is shown in FIG. 29 by way of example only, and $log_{10}$ fold change, as well as other types of representations can be employed.

Figure 30:
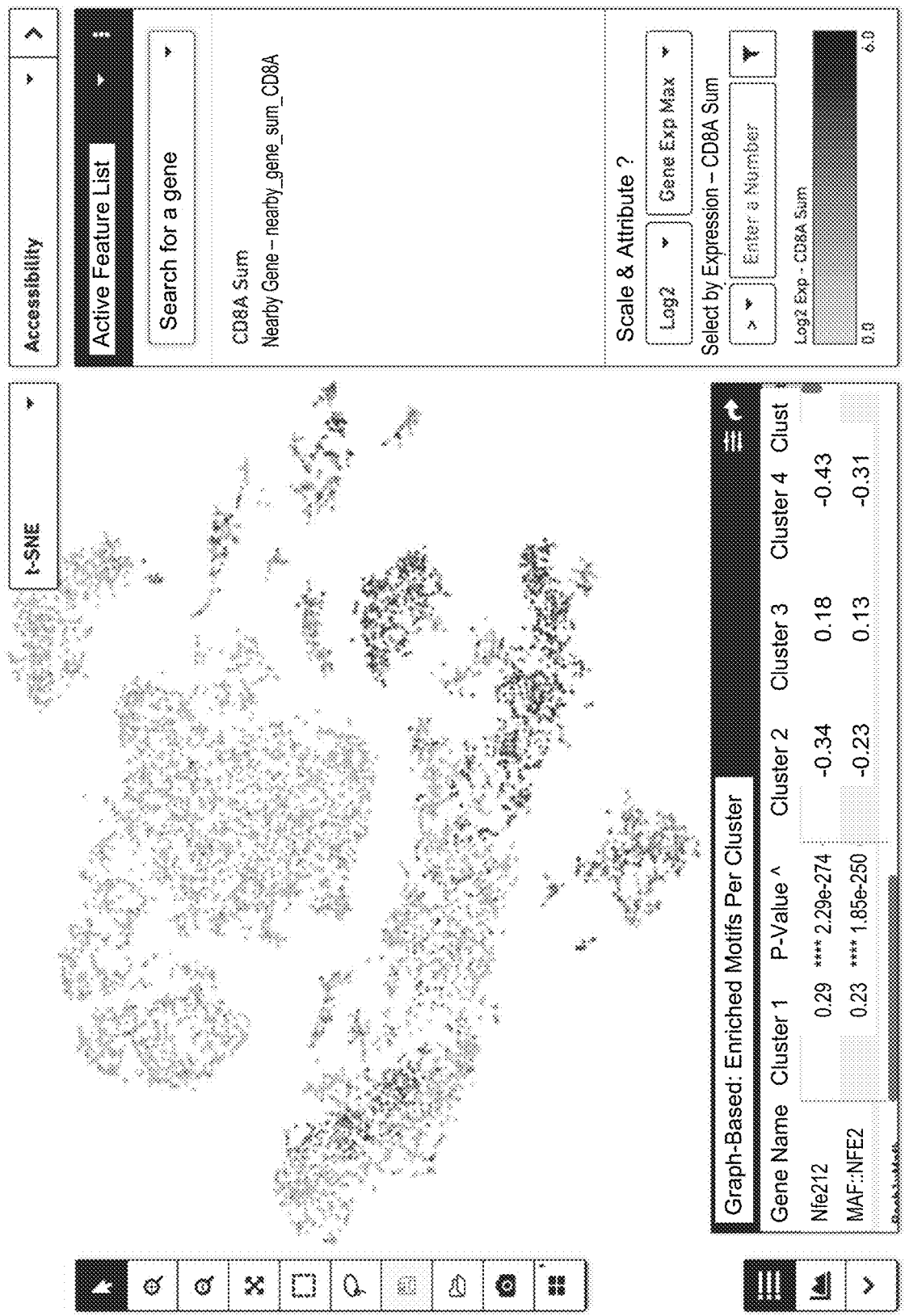
FIG. 30 illustrates an example of a user interface for selectively presenting information from an Assay for Transposase Accessible Chromatin (ATAC) dataset, where a $\log_2$-fold change representation ATAC peaks around the CD8A gene that were combined to form an aggregate feature are shown, in accordance with some embodiments of the present disclosure.

In some embodiments, aggregating feature rows is used to pool single features into a group having similar biological or technical characteristics. For example, in embodiments where ATAC data is obtained from a single cell, the feature is a peak corresponding to an open area of the genome at a particular location. There can be multiple distinct peak locations near a particular gene, or a particular gene transcription start site. Both peaks can be marked as being "nearby" that gene. The aggregate row (e.g., a sum per gene) can be generated, which is a representation of open sites of the genome per cell near that particular gene. FIG. 30 illustrates a representation (a $log_2$ fold change) of peaks around the CD8A gene that were combined to form an aggregate feature ("CD8A Sum"). In this way, the combined number of fragments near each gene per cell can be superimposed on the t-SNE plot.

In some embodiments, as discussed above, a feature metadata module (a label class) can include an additional column, "control type," (also referred to as a tag). Based on the information in this column, the visualization system can classify antibodies (or other features) as either positive or negative controls. As an example, a row in the feature metadata module can include the following columns or fields:

id, name, read, pattern, sequence, feature_type,control_type, and an example of a positive control antibody data stored in such fields may be:

CD3, CD3 UCHT1 TotalC, R2, /\NNNNNNNNNN(BC) NNNNNNNNN CTCATTGTAACTCCT, Antibody Capture, Positive.

An example of a negative control antibody data stored in the fields may be:

isotype_control_IgG1,isotype_control_IgG1 MOPC-21 TotalC, R2, /\NNNNNNNNNN(BC)NNNNNNNNN, GCCGGACGACATTAA, Antibody Capture, Negative.

Data on positive control antibodies can be aggregated into a row separate from an aggregate row aggregating data on negative control antibodies. The aggregate rows can be plotted, used for quantitative coloring, used for filtering cells by aggregate sum expression, and used for various other analyzes in accordance with embodiments of the present subject matter.

A discrete attribute value dataset can include features of multiple types, and differential expression/chromatin accessibility can be segmented by feature type. Accordingly, in some embodiments, the cell browser is configured to receive input indicating selection of a type of a feature with respect to which a differential expression/accessibility is desired to be performed.

FIG. 31 illustrates default options for an antibody dataset. They are "gene" and "antibody capture."

In some embodiments, default options for an ATAC dataset are "peak," "motif," and either a "promoter" or "nearby gene" options.

Since multiple feature types are supported by the cell browser in the described embodiments, in some in embodiments, in any user interface element where a user is entering a feature name to be autocompleted, the feature type is displayed in the autocompletion entry. This would allow a user to distinguish, e.g., between a CD4 gene and a CD4 protein.

In some embodiments, as discussed above, differential attribute values for first entities in each cluster can be computed. In some embodiments, the differential attribute values can be computed for first entities of a first type and/or for the first entities of a second type. For example, once each second entity (e.g., a cell) has been assigned to a respective cluster, the systems and methods of the present disclosure are able to compute, for each respective first entity (e.g., of the first type or of the second type) for each respective cluster, a difference in the discrete attribute value for the respective first entity (e.g., of the second type or of the second type) across the respective subset of second entities in the respective cluster relative to the discrete attribute value for the respective first entity (e.g., of the first type or of the second type) across the plurality of clusters other than the respective cluster, thereby deriving a differential value for each respective first entity (e.g., of the first type or of the second type) in the plurality of first entities (e.g., of the first type or of the second type) for each cluster. In this way, for example, the top expressing genes (e.g., first entities of the first type) that are different between cell classes or other forms of cell labels can be determined. This allows determining which genes are differentially expressed between datasets.

In some embodiments, as discussed above, sSeq is used for testing for differential expression. Each second entity (e.g., a cell) may contain mRNA expression data and various feature data (e.g., antibody data, and more generally first features of the second type) for hundreds, or thousands of different genes and/or analytes. Other single-cell differential expression methods can be used additionally or alternatively.

In embodiments in which a discrete attribute data set includes antibody data (or more generally data for a first plurality of second entities of a second type) stored in multiple features rows corresponding to respective different features, a subset of feature rows matching a particular feature type can be interrogated. The disclosed computation system will reference the feature type label class to identify the subset of rows to iterate over. In some scenarios, the UMI count total entered into the sSEQ calculation module is the aggregate feature type sum row.

In some embodiments of the present disclosure, a cell browser is configured to display ATAC data in an intuitive manner. In some embodiments cell browser 119 includes a set of tools that support representation and analysis of ATAC data and such tools are referred to herein as an ATAC Peak Viewer.

In some embodiments, data structures of a particular type are generated that allow loading ATAC data and generating representations of ATAC peaks, ATAC peak frequencies, ATAC peak shapes, the peaks' locations in a genome, and functional gene structures located in the vicinity of an ATAC peak.

An ATAC peak in accordance with the present disclosure is a representation of a region of open, accessible chromatin determined by analyzing fragments read between transposase cut sites. Unlike gene expression, where a gene is expected at the same location in a genome as per a reference genome, the location of ATAC peaks can vary from run to run as different cells can have different regions of open chromatin accessible to regulatory elements. Accordingly, in the embodiments described herein, each ATAC peak has a name associated therewith, with the name corresponding to the peak's genomic location (e.g., "chr2:237835-238281," in one example). The name of each ATAC peak can be stored a .cloupe file, similar to the manner in which gene names are stored. However, a distinct genomic location of an ATAC peak, including its chromosome index, start position and end position, are stored in a separate module (or object) in a .cloupe file, which can be referred to herein a peak location module (or "a Peak Location object").

Figure 32:
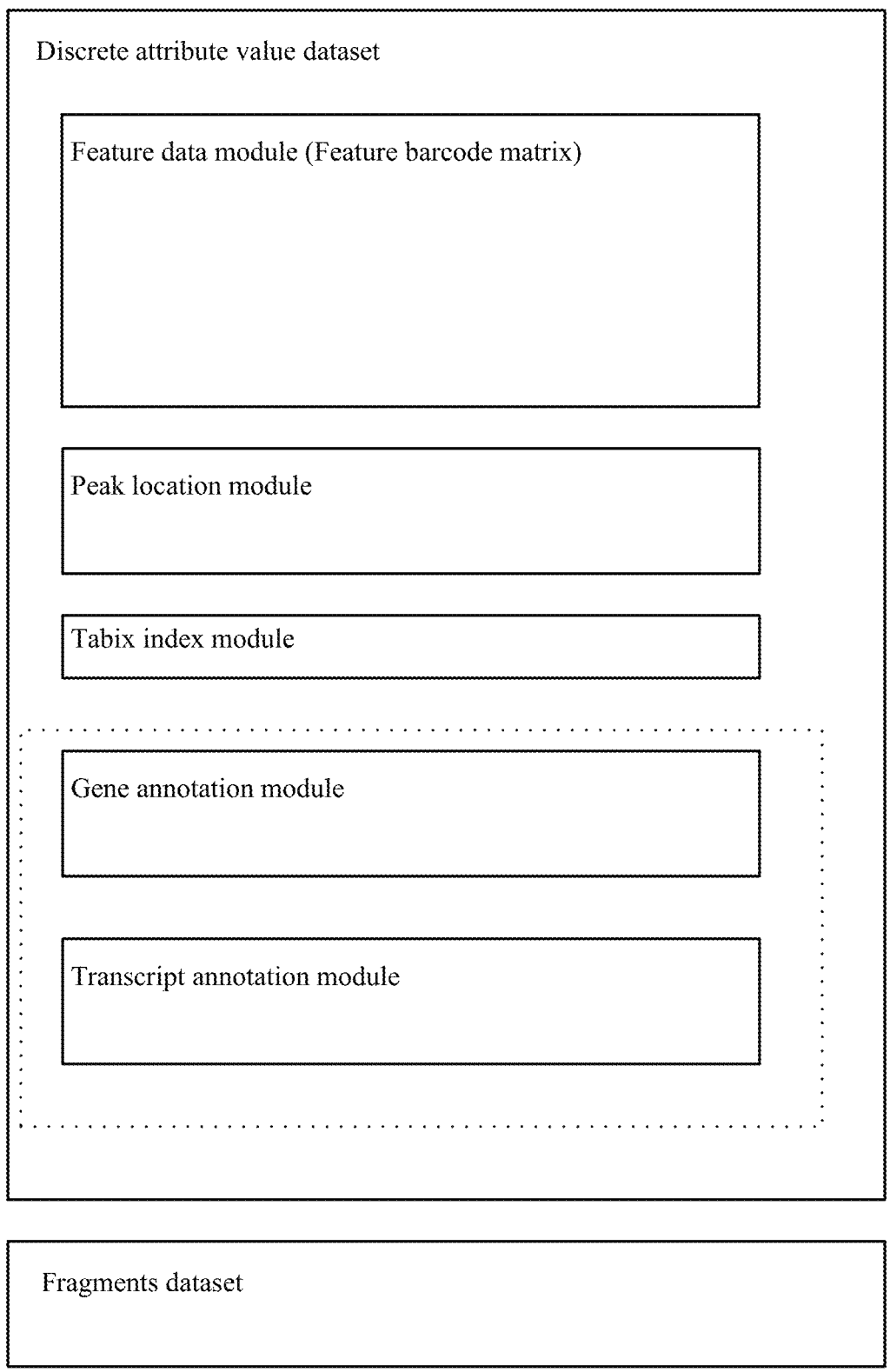
FIG. 32 is a block diagram illustrating a discrete attribute value dataset in accordance with some embodiments of the present disclosure.

As shown in FIG. 32, a discrete attribute value dataset (.cloupe file) includes a feature data module and a peak location module comprising a list of chromosome contig names/lengths, an array of contig indexes per peak, an array of peak start addresses, and an array of peak end addresses. In some embodiments, the contig indices, peak start and peak end data structures are integer arrays that can be stored as gzipped blocks. The arrays are of length P, which is the number of rows in the feature-barcode matrix that refer to peaks. In this way, for a peak n of P, the contig, start position and end position of the peak can be found at location.contigs [n], location.starts[n] and location.ends[n].

The described techniques provide computational visualization of ATAC peaks in a manner that allows identifying each peak's genomic context, including nearby genes, exons, and untranslated regions (UTRs). In some embodiments, gene, exon and UTR information is stored in the discrete attribute value dataset (.cloupe file) in a manner similar to gene annotations. The gene, exon, and UTR transcripts can be derived from genomic reference information. As shown in FIG. 32, the discrete attribute value dataset can include a gene annotation module storing respective arrays for contig indexes, start positions, end positions, gene names, gene IDs, and strandedness. The discrete attribute value dataset also supports annotation of functional regions in a gene and includes a transcript annotation module. In one embodiment, the transcript annotation module includes the following data structures:

array (string) of transcript IDs of length T (distinct transcript IDs for all transcript annotations);

array (uint) of transcript object types of length U+E=A, the total number of annotations, which is made of U UTR annotations and E exon annotations (this indicates whether the information in all subsequent arrays pertains to an exon or a UTR);

array (int) of indices into the gene ID array, of length A (the gene ID of an annotation);

array (int) of indices into the transcript ID array, of length A (the transcript ID of an annotation);

contig index array (int) of length A;

start position array (int) of length A;

end position array (int) of length A;

strand array (int) of length A.

Following these notations, a single transcript annotation is formed from entries at position i for all arrays of length A. In this manner, a transcript annotation is formed from a gene ID, transcript ID, contig index, start position, end position, and strand. Moreover, the locations of multiple exons and UTRs per transcript and multiple transcripts per gene are encoded. Information on one, two, or more than two transcripts per gene can be stored in this way. It should be noted that the feature data module, the peak location module, the gene annotation module and the transcript annotation module are shown in FIG. 32 as "modules" for representation purposes only. The data stored in these data structures in a way that is appropriate for processing of the data by the cell browser in accordance with embodiments of the present disclosure (e.g., the cell browser 119 configured to execute a .cloupe file and access and load into memory appropriate data).

In some embodiments, information stored in the gene and transcript annotation modules is sorted by respective genomic positions. In some embodiments, as schematically shown (by a dotted line) in FIG. 32, the gene annotation module and the transcript annotation modules are stored in a persistent memory (on a disk). When the cell browser is executed, the gene and transcript annotation modules are loaded from the persistent memory into a non-persistent memory (e.g., a RAM) when the attribute value dataset (e.g., an ATAC.cloupe file) is loaded into the non-persistent memory. This combination of an on-disk sorting and in-memory loading allow the cell browser and underlying hardware to respond to queries in a fast and efficient manner. In particular, in some embodiments, in response to a query, such as, e.g., a range query indicating an interval of interest, a server executing the cell browser can perform a binary search by position to find elements within the interval with performance $O(\log A)$. The performance is improved due to the fact that the annotations are grouped by chromosome/contig, such that the search for gene annotations can start within a smaller subset of the data.

ATAC peak locations are also sorted and stored in memory in a similar manner. The ATAC peaks are representations of open chromatin regions that can be determined by identifying an overlap between fragments exposed by two transposase cut sites. Furthermore, analyzing the fragments themselves can reveal additional information and structure. Accordingly, in some embodiments, the ATAC pipeline is configured to generate a fragments module (stored separately from the discrete attribute dataset) that includes the following columns: a cell barcode column storing a barcode of a cell on which the fragment was found, and a contig, start and end position columns storing the contig, start, and end positions of the fragment, respectively. The fragments module can be in the form of a tab delimited data structure, which can be optionally compressed (e.g. gzipped). The ATAC pipeline is configured to compute a tabix index over the compressed (e.g., gzipped) tab-delimited information stored in the fragments module. A tabix index module stores the computed tabix index that allows for faster lookup of the on-disk chunks of fragments within a particular interval. The tabix index can be computed as described, for example, in Li, 2011, "Tabix: fast retrieval of sequence features from generic TAB-delimited files," Bioinformatics, 27(5): 718-719. Other techniques can be used additionally or alternatively. In some embodiments, the tabix file module is embedded into the attribute value dataset (e.g., a .cloupe file), whereas the fragments module, which may be hundreds of megabytes to gigabytes in size, is stored separately from the attribute value dataset.

Figure 33:
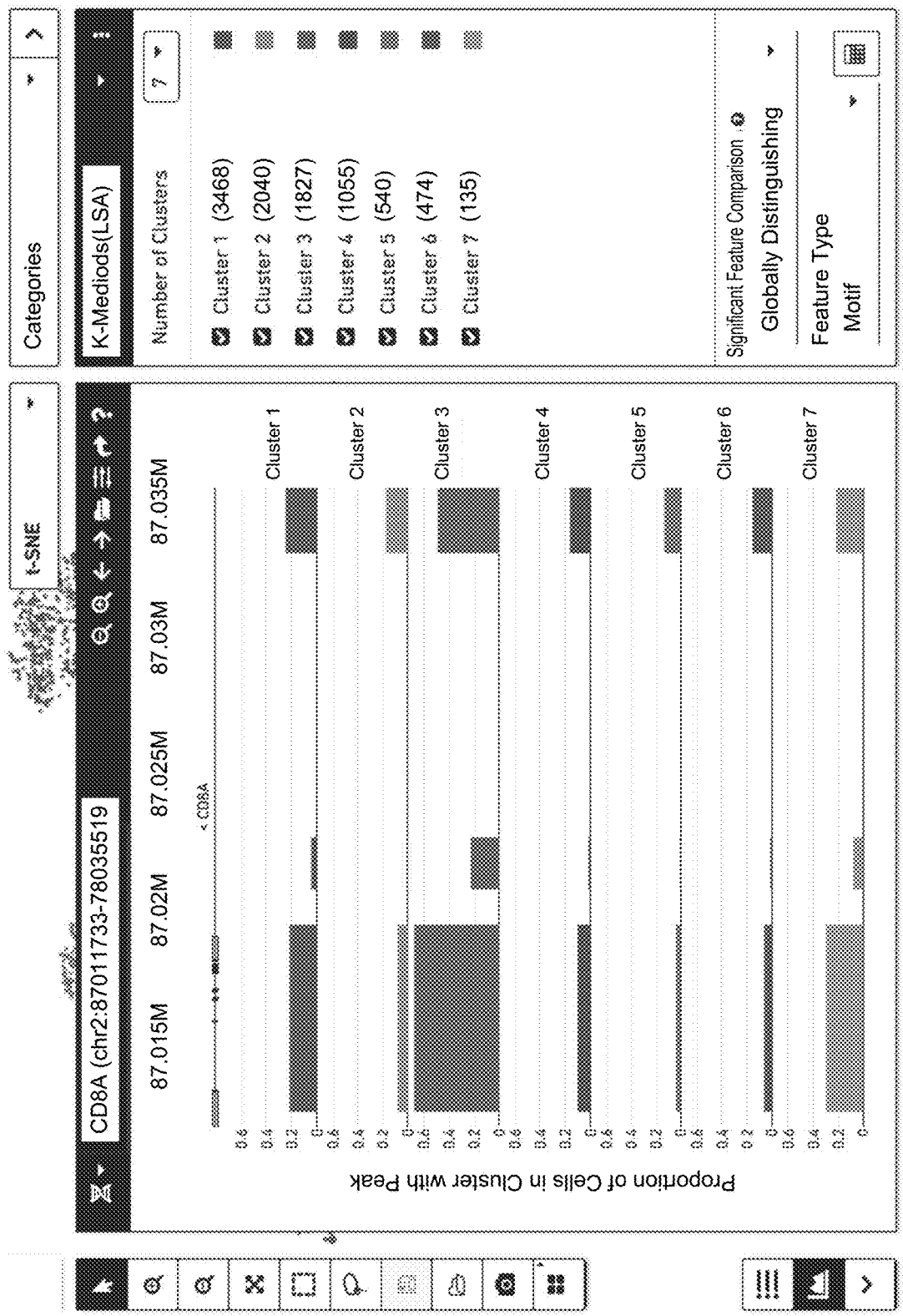
FIG. 33 illustrates an example of a user interface for selectively presenting information from an ATAC dataset, where the "Gene" option is selected and where ATAC peaks per each cluster near the CD8A gene are displayed, in accordance with some embodiments of the present disclosure.
Figure 35:
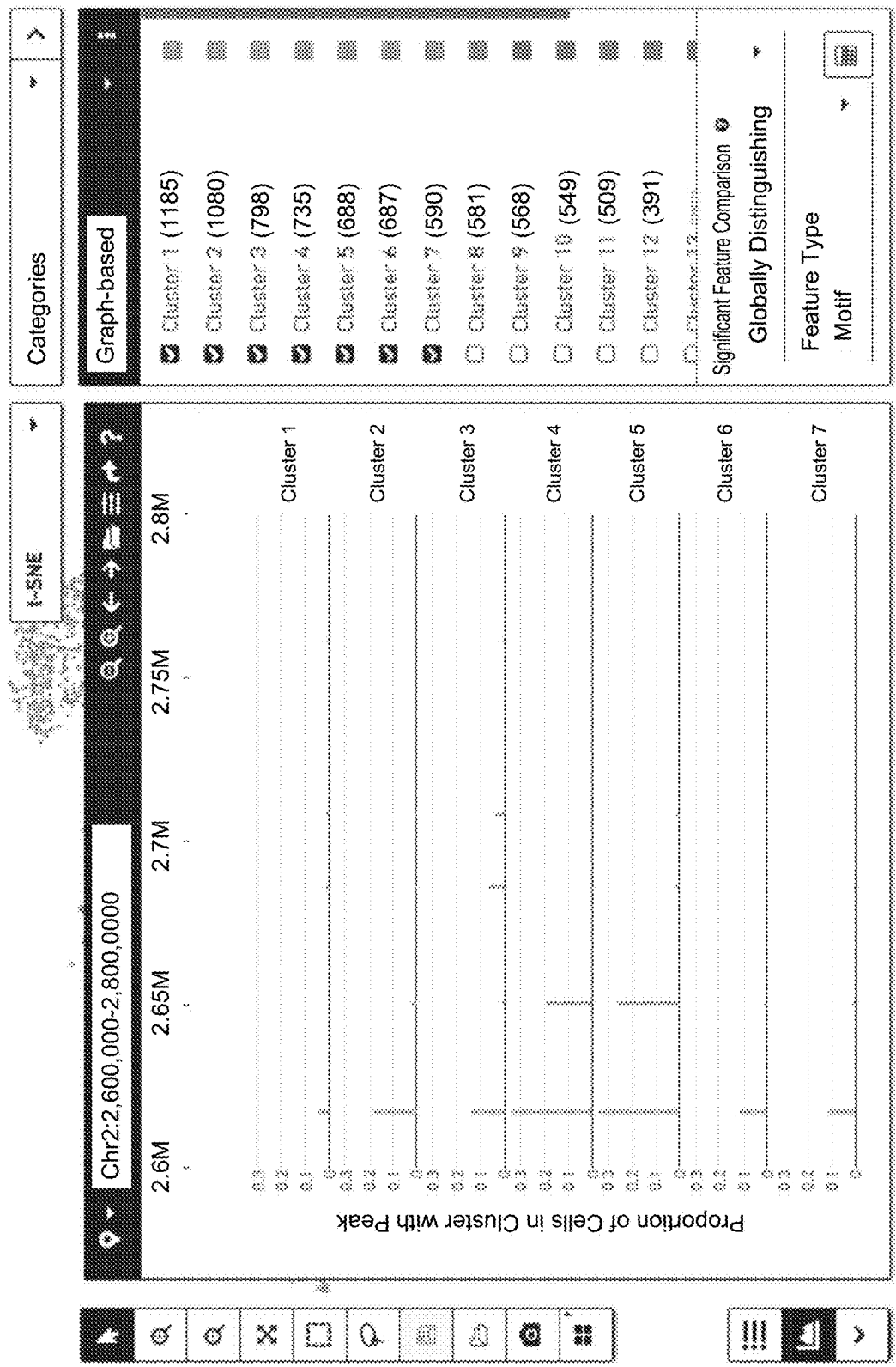
FIG. 35 illustrates an example of a user interface for selectively presenting information from an ATAC dataset, where the "Region" option is selected and where ATAC peaks per each cluster within a selected region are displayed, in accordance with some embodiments of the present disclosure.

Referring back to visual representation of ATAC peaks and associated information, a user interface rendered by the cell browser can include an interactive icon that is configured to receive input indicating a selection of an option to display a peak viewer panel. The peak viewer panel can be configured to display a relative distribution of ATAC peaks and occurrence of fragments between different clusters in a currently-selected category. As shown in FIG. 33, in the upper left portion of the user interface, an icon is displayed that is responsive to an input indicating a selection of gene ("Gene") or a genomic region ("Region"). For example, as shown in FIG. 33, when the "Gene" option is selected, and when the user input includes "CD8A," ATAC peaks per each cluster (seven clusters, in this example) near the CD8A gene are displayed. As another example (FIG. 35), when the "Region" option is selected and the user input includes, e.g., "chr2:2,600,000-2,800,000," all ATAC peaks in the selected 200,000 bp region will be displayed. The peak information is generated by the server, by using the tabix index discussed above, to identify unique peaks for the visible region, and accessing the feature data module to extract information for all ATAC peak rows.

As shown in FIG. 33 illustrating an example of a visual representation of ATAC peaks identified in the CD8A gene in cells from a certain sample, each peak can be represented as a corresponding rectangle that spans a certain genomic region within which the peak was detected. Each "active" (selected) cluster has a track in the visualization. In this example, the height of the peak rectangle within each track is proportional to the percentage of cells within that cluster which have a fragment site within a particular peak for which the peak count for that cell at that peak in the feature dataset (e.g., a peak-barcode matrix) is nonzero. In this example, peak heights are normalized to the highest frequency among all clusters. However, it should be appreciated that the normalization is optional. If an input device (e.g., a computer mouse or another device, including user's finger if the display is a touch screen) is detected over a representation of a peak, information related to the peak, such as, e.g., the peak's position, frequency within the cluster, and whether the peak region either encloses or is near a functional region of the gene, can be displayed.

Figure 34:
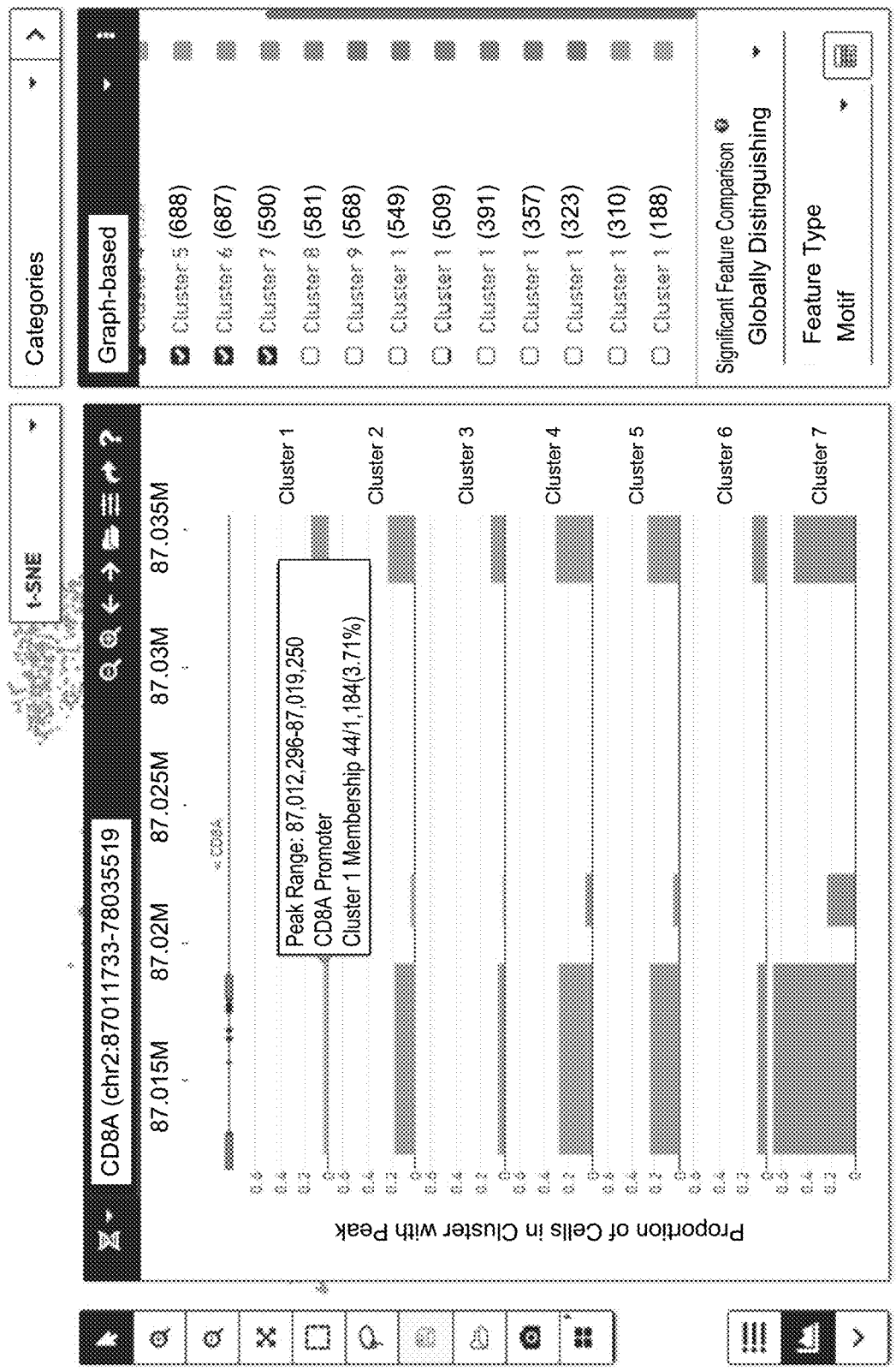
FIG. 34 illustrates an example of the user interface of FIG. 33 where information on a selected peak is displayed in accordance with some embodiments of the present disclosure.

As shown in FIG. 34, if a pointer of an input device (e.g., a computer mouse) is disposed over a peak (or otherwise positioned with respect to the peak, depending on the specific implementation), information on the peak's position, frequency within a cluster, and whether the peak region either encloses or is near a functional region of the gene can be displayed. In the example of FIG. 35, referring again to the example of the CD8A gene, when the mouse is positioned over a rectangle corresponding to a peak, as shown in FIG. 35, the processor instructs the user interface to display the peak's location ("ch2:87,012,296-87,019,250"), the potential function of the peak's region (CD8A Promoter) and the relative frequency within that cluster (3.71%).

As discussed above, embodiments of the present disclosure store and employ gene and transcript annotations. In some implementations of the cell browser, gene annotations for a genomic region are displayed as lines, e.g., above the cluster peak tracks, as illustrated in FIG. 34. In some embodiments, the gene can be represented by a solid line. However, it should be appreciated that various other representations of a gene can be generated additionally or alternatively. For example, in some implementations, a gene boundary may be dashed, and a recorded transcript may be in the form of a solid line. Any other types of representations can be used, including, e.g., vertical lines that indicate gene boundaries.

In the representation of ATAC peaks in accordance with the described techniques, exonic regions and untranslated regions (UTRs) can be represented in the user interface in any suitable manner. For example, in one implementation, exonic regions are shown as solid rectangles (e.g., black or of any other color) adjacent to (e.g., atop) the gene annotation, and UTRs are in the form of unfilled rectangles. Visual representation(s) of one, two, or more than two transcripts per gene in a reference genome can be generated. In some implementations, a strand of a gene is shown by a backward (<) or forward (>) arrow next to the gene annotation. In response to detecting that an input device is positioned such that its pointer hovers over the gene name, gene position, gene ID, and transcript ID (as found in the reference genome) may be displayed in some implementations.

The representation of ATAC peaks and associated information in accordance with embodiments of the present disclosure can be modified in various ways in response to user input. For example, user input can be received indicating an instruction to zoom out, zoom in, pan left and pan right.

In some embodiments, the default representation of ATAC peaks displays the peaks, e.g., as shown in FIG. 33. Furthermore, the cell browser is configured to display representation of the overlap of open fragments. This information can be displayed in in response to input specifying a location of a fragments module (or file) storing the fragment information associated with the ATAC dataset. For example, the fragment information can be acquired (e.g., from a fragments dataset of module of FIG. 32) in response to a user input (e.g., with response to a "folder" icon) including an instruction to load a ".tsv.gz" file. In some embodiments, a user input can indicate a URL indicating a location of the fragments module file. In some embodiments, a backend server performs a "sanity check" to verify that the fragments module is correctly associated with the stored fragments tabix index. If the proper association is verified, the fragment information, together with peak information, can be employed for every range and gene query. On the backend, the server interrogates the tabix index stored in the .cloupe file, which will return the byte offset of the chunks within the block-gzipped fragments file containing fragments within the visible region. Since the beginning and ending chunks may also contain fragment locations outside the visible window, the server may apply overlap filtering to ensure that each fragment is within the visible window.

Figure 36:
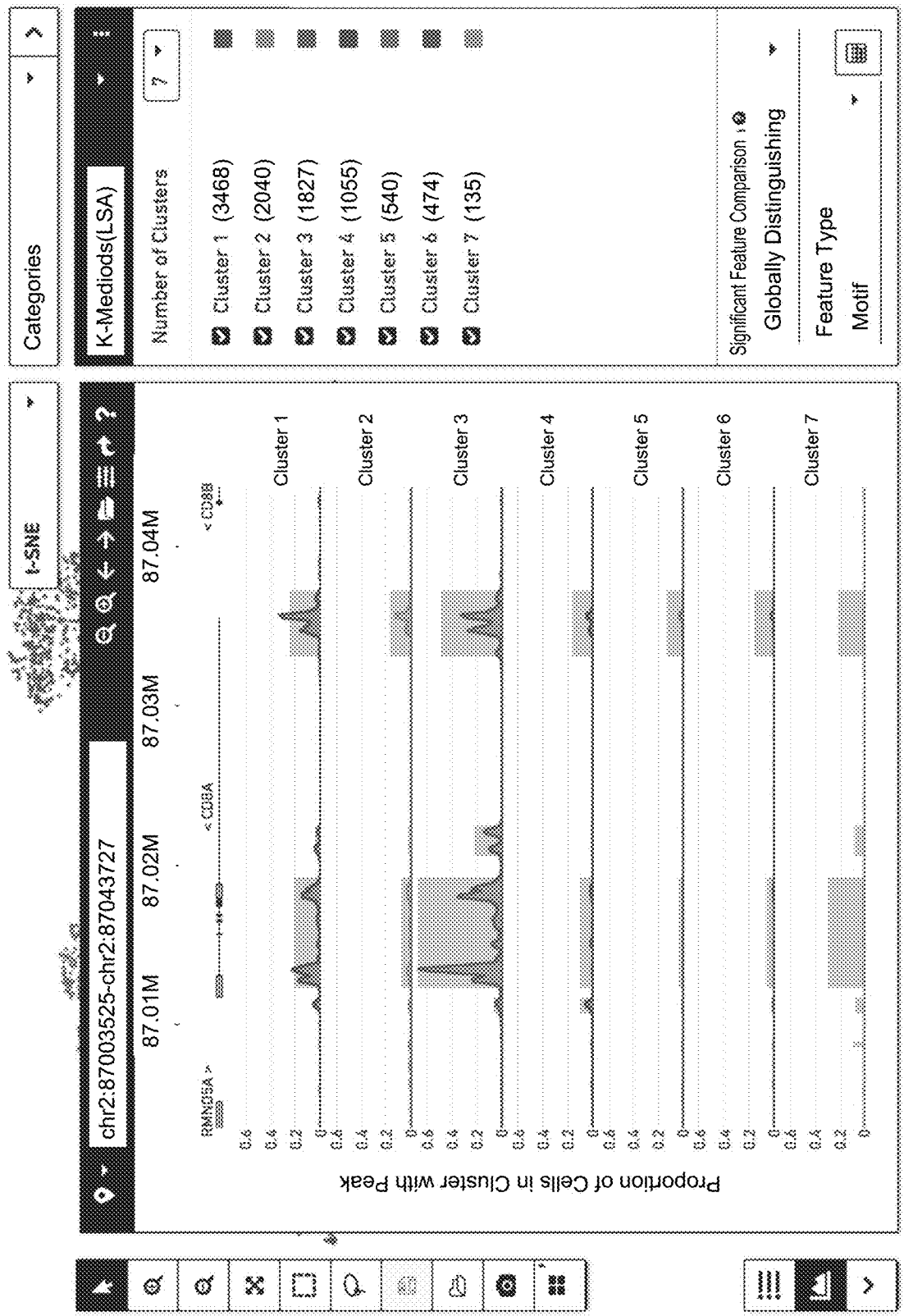
FIG. 36 illustrates an example of a user interface for selectively presenting information from an ATAC dataset, including information on fragments, in accordance with some embodiments of the present disclosure.

In some embodiments, when fragments information is loaded into memory for use by processing core(s) executing the cell browser, a user interface is instructed to present respective fragments information along with a representation of the peaks. For example, as shown in FIG. 36, the user interface can present fragments information in the form of grey (in this example) rectangles "behind" the peaks. This information is generated as rolling window sums of fragment cut sites within a certain distance (e.g., default may be 200 bp or a window of another size) from that spot in the genome. The y-value of each track is the total number of fragments found in cells among that cluster with a start or end position within n base pairs of the underlying genomic location on the x-axis, where n can be user-specified. In the example of the user interface in FIGS. 33 and 35, heights of the grey rectangles representing fragments are normalized to the largest number of cut sites found at any point in any one cluster. In some embodiments, these may be further normalized by cell count per cluster. If a pointer of an input device is detected over the trace, the number of fragment cut sites (either the start or end of the fragment) within a certain distance of that point is displayed. This indicates accessibility of the chromatin of that point. The representation of the fragment peaks in relation to functional elements in the gene allows assessing biological context of those peaks.

Figure 37:
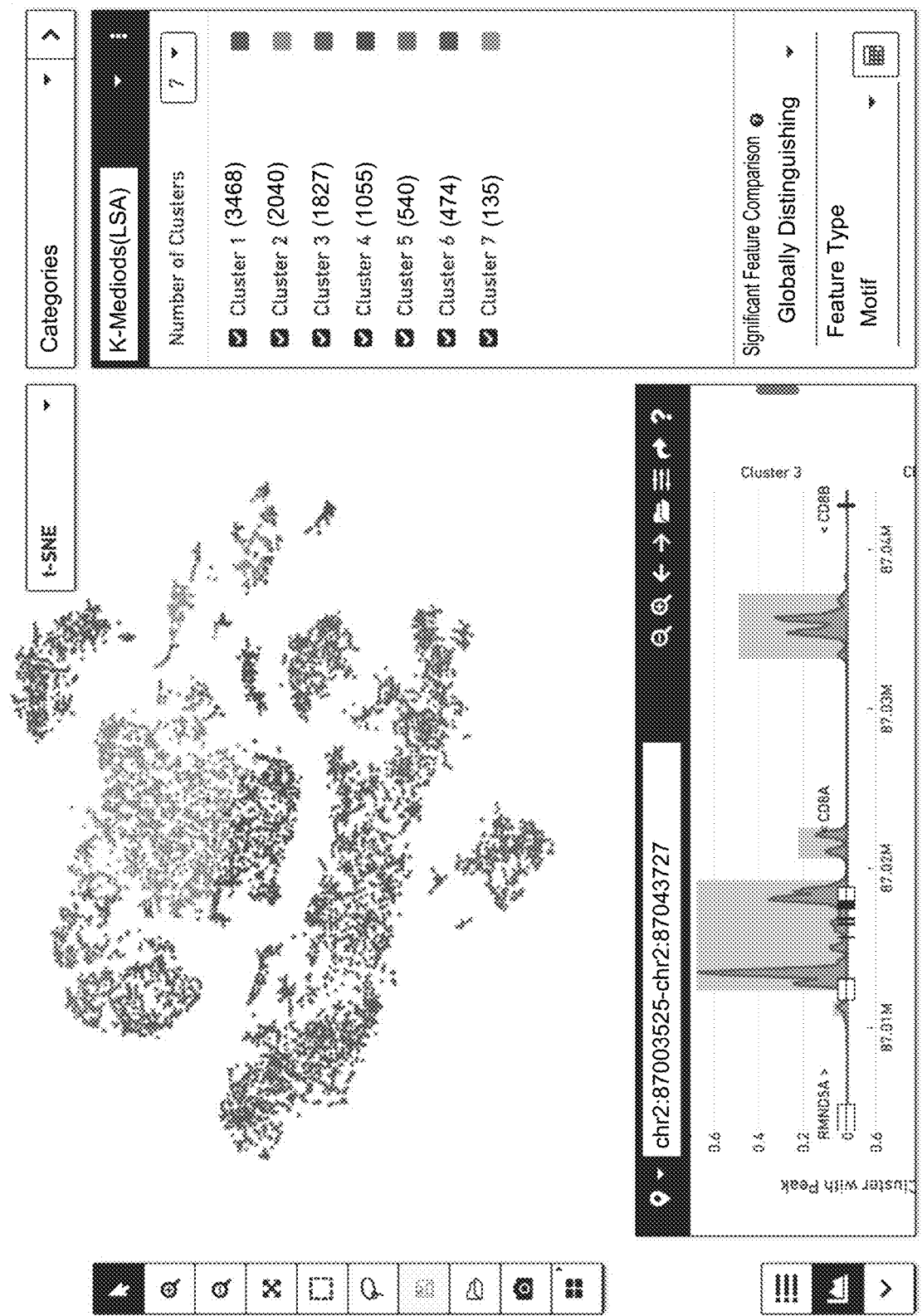
FIG. 37 illustrates an example of a user interface for selectively presenting information from an ATAC dataset, where the user interface present cluster information and ATAC peak information in accordance with some embodiments of the present disclosure.

The ATAC peaks and associated information can be displayed in an interactive manner, such that one or more elements in the user interface can be modified automatically or in response to user input. For example, in some embodiments, user input can be received instructing the server to modify the representation of the peaks. For example, a selection of a "disable auto height" option will result in a change in the allocation for each cluster from a percentage of the peak viewer height to a fixed number of pixels. In this view, the gene annotation track drops from above the clusters to an overlay atop it. As shown in FIG. 37, in response to user input (which can be, for example, moving the scroll bar up and down), cluster representation can be displayed underneath the gene annotation. A user can instruct the user interface to return to the auto height representation by selecting the "enable auto height" option. Furthermore, when peak distribution and fragment cut site location data is loaded, the user interface provides an option to "hide" fragment traces or peaks with the "show/hide peak distribution" and "show/hide cut sites" options displayed on the user interface. Similarly, gene annotations can be displayed or removed from the display.

Furthermore, as mentioned above, values of the fragment traces are functions of the windows around each position in the genome. The described techniques allow a user to vary the "openness" metric, based on the assumption that chromatin may be less accessible downstream from a particular cut site. Thus, the user interface can allow selecting the width of the window used to mark locations as being accessible by choosing, e.g., a value of a "smoothing window size" option. Smaller windows may reveal further nuances in the distribution of cut sites.

In some embodiments, underlying data and/or the graphical representation of the peak information can be stored in a suitable format. For example, in response to an indication that an "export" option is selected, the server hardware can instruct the cell browser to store the information. In this way, the frequency of each currently visible peak within each cluster can be stored, e.g., as a CSV file that is exported as a .bedgraph file representing the windowed cut site sums for each cluster. The graphical representation of the peaks can be stored in PNG, SVG, or any other suitable format. It should be noted that the embodiments of the present disclosure are not limited with respect to a format in which the peak data and peak's graphical representation can be stored.

In some embodiments, a visualization system is provided that includes one or more processing cores (or computing hardware), a persistent memory and a non-persistent memory. The persistent memory and the non-persistent memory collectively store instructions for performing a method for visualizing a pattern in a discrete attribute value dataset. The method includes storing the discrete attribute value dataset in persistent memory, wherein the discrete attribute value dataset comprises a corresponding first discrete attribute value for each first entity of a first type in a plurality of first entities of the first type and a corresponding second discrete attribute value for each first entity of a second type in a plurality of first entities of a second type for each respective second entity in a plurality of second entities. The discrete attribute value dataset redundantly represents the corresponding first discrete attribute value for each first entity the first type and the corresponding second discrete attribute value for each first entity of the second type for each respective second entity in both a compressed sparse row format and a compressed sparse column format in which first entities for a respective second entity that have a null discrete attribute data value are discarded. The discrete attribute value dataset can be compressed in accordance with a blocked compression algorithm. The corresponding second discrete attribute value for each first entity of the second type in the plurality of first entities of the second type is associated with metadata.

The method further includes clustering the discrete attribute value dataset using the first discrete attribute value for each first entity of the first type or the second discrete attribute value for each first entity of the second type in the plurality of first entities, or principal components or other forms of data reduction components derived therefrom, for each respective second entity in the plurality of second entities. In this way, each respective second entity in the plurality of second entities is assigned to a corresponding cluster in a plurality of clusters.

In some embodiments, when performing the clustering, the processing cores of the visualization system load less than the entirety of the discrete attribute value dataset into the non-persistent memory at any given time during the clustering.

In some embodiments, the method for visualizing the pattern in the discrete attribute value dataset further includes, in response to receiving input instructing the visualization system to present first information related to at least one second attribute value for a first entity of the second type in the plurality of first entities of the second type for a respective second entity in the plurality of second entities, presenting on a user interface the first information, wherein the first information is presented in association with second information that is related to a corresponding cluster to which the respective second entity in the plurality of second entities is assigned.

For example, in some embodiments, information related to results of analysis of gene expression counts is presented in association with information related to results of analysis of non-gene feature counts. In other embodiments, as discussed above, information related to results of analysis of open chromatin regions in a genome of each cell in a sample (e.g., ATAC peak information) is presented. The information is presented on a user interface of a computing device in an interactive manner, such that the user interface can receive user input instructing the user interface to modify representation of the information. Various additional information can be displayed in response to user input. Moreover, previously unknown patterns and relationships can be discovered using the presentation of the data on the user interface. In this way, a biological sample can be characterized.

EXAMPLE

Figure 15:
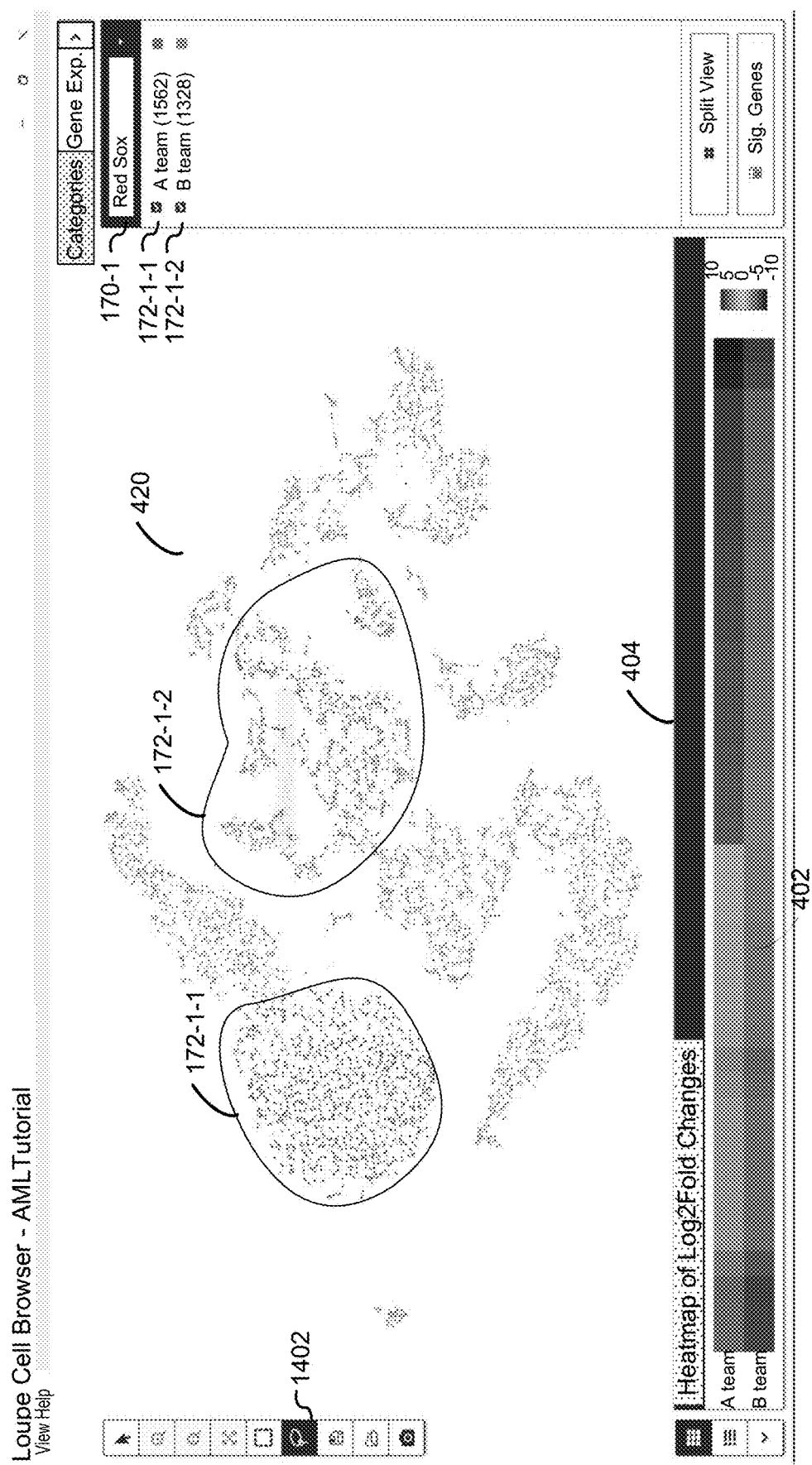
FIG. 15 illustrates the user selection of classes for a user defined category and the computation of a heatmap of $log_2$ fold changes in the abundance of mRNA transcripts mapping to individual genes in accordance with some embodiments of the present disclosure.

Referring to FIG. 15, an example visualization system 100 comprising a plurality of processing cores, a persistent memory and a non-persistent memory was used to perform a method for visualizing a pattern in a dataset. For this Example, the example visualization system 100 was a Lenovo ThinkPad with MICROSOFT WINDOWS 10 PRO, Model 243852U, 16.0 gigabytes of RAM memory, and Intel i7-3740QM CPM operating at 2.70 gigaHerz with 4 cores and 8 logical processors with the cell browser module 150 installed. The discrete attribute value dataset 120, consisting of mRNA whole transcriptome expression data from 8,390 different cells was stored in persistent memory. The dataset consisted of a corresponding discrete attribute value (mRNA transcript abundance) for each first entity in a plurality of first entities for each respective second entity (cell) in a plurality of second entities. The discrete attribute value dataset 120 redundantly represented the corresponding discrete attribute value for each first entity in the plurality of first entities for each respective second entity in the plurality of second entities in both a compressed sparse row format and a compressed sparse column format in which first entities for a respective second entity that have a null discrete attribute data value are discarded. The dataset was compressed in accordance with a blocked compression algorithm. The dataset was clustered prior to loading onto the example computer system 100, using principal components derived from the discrete attribute values for each first entity in the plurality of first entities, for each respective second entity in the plurality of second entities thereby assigning each respective second entity in the plurality of second entities to a corresponding cluster in a plurality of clusters. These cluster assignments were already assigned prior to loading the dataset into the example computer system 100. Each respective cluster in the plurality of clusters consisted of a unique different subset of the second plurality of entities.

There was computed, for each respective first entity in the plurality of first entities for each respective cluster in the plurality of clusters, a difference in the discrete attribute value for the respective first entity across the respective subset of second entities in the respective cluster relative to the discrete attribute value for the respective first entity across the plurality of clusters other than the respective cluster, thereby deriving a differential value for each respective first entity in the plurality of first entities for each respective cluster in the plurality of clusters. These differential values where displayed in a heat map in the upper panel 420. The heat map comprised a representation of the differential value for each respective first entity in the plurality of first entities for each cluster in the plurality of clusters thereby visualizing the pattern in the dataset. This concept has been illustrated above in conjunction with FIG. 4.

Next, referring to FIG. 15, a new category, Red Sox, that was not in the loaded discrete attribute value dataset 120 was user defined by selecting a first class of second entities (cells) 172-1-1 ("A team") using Lasso 1402 and selecting displayed second entities 126 in the upper panel 420. Further, a second class of second entities 172-1-2 ("B team") was user defined using Lasso 1402 and selecting displayed second entities 126 in the upper panel 420 as illustrated in FIG. 15. Next, the first entities whose discrete attribute values 124 discriminate between the identified user defined classes "A team" and "B team" was computed. For this, the locally distinguishing option 1206 described above in conjunction with FIG. 12 was used to identify the first entities whose discrete attribute values discriminate between class 172-1-1 (A team) and class 172-1-2 (B team). The A team consisted of whole transcriptome mRNA transcript counts for 1562 cells. The B team consisted of whole transcriptome mRNA transcript counts for 1328 cells. To do this, the differential value for each respective first entity in the plurality of first entities for class 172-1-1 was computed as a fold change in (i) a first measure of central tendency of the discrete attribute value for the respective first entity measured in each of the second entities in the plurality of second entities in the class 172-1-1 and (ii) a second measure of central tendency of the discrete attribute value for the respective first entity measured in each of the second entities in the class 172-1-2 was computed. Then the heatmap 402 of this computation for each of the first entities was displayed in the lower panel 404 as illustrated in FIG. 15. The heatmap shows which first entities discriminate between the two classes. An absolute definition for what constitutes discrimination between the two classes is not provided because such definitions depend upon the technical problem to be solved. Moreover, those of skill in the art will appreciate that many such metrics can be used to define such discrimination and any such definition is within the scope of the present disclosure. Advantageously, the computation and display of the heatmap 402 only took 8.12 seconds on the example system using the disclosed clustering module 152 (Lenovo ThinkPad with MICROSOFT WINDOWS 10 PRO, Model 243852U, 16.0 gigabytes of RAM memory, and Intel i7-3740QM CPM operating at 2.70 gigaHerz with 4 cores and 8 logical processors).

Had more classes been defined, more computations would be needed. For instance, had there been a third class in this category and this third class selected, the computation of the fold change for each respective first entity would comprise:

for the first class 172-1-1, computing (i) a first measure of central tendency of the discrete attribute value for the respective first entity measured in each of the second entities in the plurality of second entities of the first class 172-1-1 and (ii) a second measure of central tendency of the discrete attribute value for the respective first entity measured in each of the second entities in the second 172-1-2 and third classes 172-1-3 collectively, for the second class 172-1-1, computing (i) a first measure of central tendency of the discrete attribute value for the respective first entity measured in each of the second entities in the plurality of second entities of the second class 172-1-2 and (ii) a second measure of central tendency of the discrete attribute value for the respective first entity measured in each of the second entities in the first class 172-1-1 and the third class 172-1-3 collectively, and for the third class 172-1-3, computing (i) a first measure of central tendency of the discrete attribute value for the respective first entity measured in each of the second entities in the plurality of second entities of the third class 172-1-3 and (ii) a second measure of central tendency of the discrete attribute value for the respective first entity measured in each of the second entities in the first class 172-1-1 and the second class 172-1-2 collectively.

Conclusion

All references cited herein are incorporated herein by reference in their entirety and for all purposes to the same extent as if each individual publication or patent or patent application was specifically and individually indicated to be incorporated by reference in its entirety for all purposes.

Plural instances may be provided for components, operations or structures described herein as a single instance. Finally, boundaries between various components, operations, and data stores are somewhat arbitrary, and particular operations are illustrated in the context of specific illustrative configurations. Other allocations of functionality are envisioned and may fall within the scope of the implementation(s). In general, structures and functionality presented as separate components in the example configurations may be implemented as a combined structure or component. Similarly, structures and functionality presented as a single component may be implemented as separate components. These and other variations, modifications, additions, and improvements fall within the scope of the implementation(s).

It will also be understood that, although the terms first, second, etc. may be used herein to describe various elements, these elements should not be limited by these terms. These terms are only used to distinguish one element from another. For example, a first subject could be termed a second subject, and, similarly, a second subject could be termed a first subject, without departing from the scope of the present disclosure. The first subject and the second subject are both subjects, but they are not the same subject.

The terminology used in the present disclosure is for the purpose of describing particular embodiments only and is not intended to be limiting of the invention. As used in the description of the invention and the appended claims, the singular forms "a", "an" and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the term "if" may be construed to mean "when" or "upon" or "in response to determining" or "in response to detecting," depending on the context. Similarly, the phrase "if it is determined" or "if [a stated condition or event] is detected" may be construed to mean "upon determining" or "in response to determining" or "upon detecting (the stated condition or event (" or "in response to detecting (the stated condition or event)," depending on the context.

The foregoing description included example systems, methods, techniques, instruction sequences, and computing machine program products that embody illustrative implementations. For purposes of explanation, numerous specific details were set forth in order to provide an understanding of various implementations of the inventive subject matter. It will be evident, however, to those skilled in the art that implementations of the inventive subject matter may be practiced without these specific details. In general, well-known instruction instances, protocols, structures and techniques have not been shown in detail.

The foregoing description, for purpose of explanation, has been described with reference to specific implementations. However, the illustrative discussions above are not intended to be exhaustive or to limit the implementations to the precise forms disclosed. Many modifications and variations are possible in view of the above teachings. The implementations were chosen and described in order to best explain the principles and their practical applications, to thereby enable others skilled in the art to best utilize the implementations and various implementations with various modifications as are suited to the particular use contemplated.

What is claimed:

1. A visualization system, the visualization system comprising one or more processing cores, a persistent memory and a non-persistent memory, the persistent memory and the non-persistent memory collectively storing instructions for performing a method for visualizing a pattern in a discrete attribute value dataset, the method comprising:

storing the discrete attribute value dataset in the persistent memory, wherein the discrete attribute value dataset comprises, for each respective second entity in a plurality of second entities, (i) a corresponding first discrete attribute value for each first entity of a first type in a plurality of first entities of the first type and Iii) a corresponding second attribute value for each first entity of a second type in a plurality of first entities of a second type, and the discrete attribute value dataset redundantly represents the corresponding first attribute value for each first entity of the first type in the plurality of first entities of the first type and the corresponding second attribute value for each first entity of the second type in the plurality of first entities of the second type for each respective second entity in the plurality of second entities in both a compressed sparse row format and a compressed sparse column format in which first entities for a respective second entity that have a null discrete attribute data value are discarded, the corresponding second attribute value for each first entity of the second type in the plurality of first entities of the second type is associated with metadata;

clustering the discrete attribute value dataset using the first discrete attribute value for at least one first entity of the first type and/or the second attribute value for at least one first entity of the second type, or a plurality of dimension reduction components derived therefrom, for each respective second entity in the plurality of second entities thereby assigning each respective second entity in the plurality of second entities to a corresponding cluster in a plurality of clusters, wherein the clustering is configured to load less than the entirety of the discrete attribute value dataset into the non-persistent memory during the clustering thereby allowing the clustering of the discrete attribute value dataset having a size that exceeds storage space in the non-persistent memory allocated to the discrete attribute value dataset; and in response to receiving input instructing the visualization system to present first information related to at least one second attribute value for a first entity of the second type in the plurality of first entities of the second type for a respective second entity in the plurality of second entities, displaying in a first panel of a user interface the first information, wherein the first information is presented in association with second information that is related to a corresponding cluster to which the respective second entity in the plurality of second entities is assigned.

2. The visualization system of claim 1, wherein the method further comprises:

computing, for each respective first entity of the second type in the plurality of first entities of the second type for each respective cluster in the plurality of clusters, a difference in the discrete attribute value for the respective first entity of the second type in the plurality of first entities of the second type across the respective subset of second entities in the respective cluster relative to the attribute value for the respective first entity of the second type in the plurality of first entities of the second type across the plurality of clusters other than the respective cluster, thereby deriving a differential value for each respective first entity of the second type in the plurality of first entities of the second type for each respective cluster in the plurality of clusters; and displaying in a second panel of the user interface a representation of the differential value for each respective first entity of the second type in the plurality of first entities of the second type for each cluster in the plurality of clusters.

3. The visualization system of claim 1, wherein each respective cluster in the plurality of clusters consists of a unique different subset of the second plurality of entities.

4. The visualization system of claim 1, wherein at least one second entity in the plurality of second entities is assigned to more than one cluster in the plurality of clusters such that the assignment of the at least one second entity to each of the more than one cluster is associated with a probability value indicating a probability that the at least one second entity belongs to a respective each of the more than one cluster.

5. The visualization system of claim 1, wherein the clustering is performed using discrete attributes values for a portion of first entities of the first type and/or discrete attributes values for a portion of first entities of the second type, for each respective second entity in the plurality of second entities.

6. The visualization system of claim 1, wherein each first entity of the first type in the plurality of first entities of the first type is a respective gene in a plurality of genes;

each discrete attribute value for a first entity of the first type is a count of transcript reads within the second entity that map to a respective gene in the plurality of genes;

each first entity of the second type in the plurality of first entities of the second type is a respective feature in a plurality of features;

each discrete attribute value for a first entity of the second type is a count of transcript reads of features within the second entity that map to a respective feature in the plurality of features; and each second entity is a single cell.

7. The visualization system of claim 6, wherein the discrete attribute value dataset represents a whole transcriptome shotgun sequencing experiment that quantifies gene expression from a single cell in counts of transcript reads mapped to the genes.

8. The visualization system of claim 6, wherein the plurality of features comprises antibody cell-surface markers.

9. The visualization system of claim 6, wherein the plurality of features comprises CRISPR-targeted guide RNA (gRNA) sequences.

10. The visualization system of claim 6, wherein the plurality of features comprises regions in a genome determined using a single cell Assay for Transposase-Accessible Chromatin (ATAC).

11. The visualization system of claim 1, wherein each cluster in the plurality of clusters is assigned a different graphic or color code, and each respective second entity in the plurality of entities is coded in the user interface with the different graphic or color code for the cluster the respective second entity has been assigned.

12. The visualization system of claim 1, wherein the clustering of the discrete attribute value dataset is performed on a remote computer system remote from the visualization system prior to storing the discrete attribute value dataset in the persistent memory of the visualization system, wherein the clustering on the remote computer system loads less than the entirety of the discrete attribute value dataset in a non-persistent memory of the remote computer system during the clustering on the remote computer system.

13. The visualization system of claim 1, wherein the clustering the discrete attribute value dataset comprises hierarchical clustering, agglomerative clustering using a nearest-neighbor algorithm, agglomerative clustering using a farthest-neighbor algorithm, agglomerative clustering using an average linkage algorithm, agglomerative clustering using a centroid algorithm, or agglomerative clustering using a sum-of-squares algorithm.

14. The visualization system of claim 1, wherein the clustering the discrete attribute value dataset comprises application of a Louvain modularity algorithm, k-means clustering, a fuzzy k-means clustering algorithm, or Jarvis-Patrick clustering.

15. The visualization system of claim 1, wherein the clustering the discrete attribute value dataset comprises k-means clustering of the discrete attribute value dataset into a predetermined number of clusters.

16. The visualization system of claim 1, wherein the clustering the discrete attribute value dataset comprises k-means clustering of the discrete attribute value dataset into a number of clusters, wherein the number is acquired based on user input.

17. The visualization system of claim 1, wherein the clustering the discrete attribute value dataset comprises application of a Louvain modularity algorithm to a map, the map comprising a plurality of nodes and a plurality of edges, each node in the plurality of nodes represents a second entity in the plurality of second entities, wherein the coordinates in N-dimensional space of a respective node in the plurality of nodes are a set of principal components of the corresponding second entity in the plurality of second entities, wherein the set of principal components is derived from the corresponding discrete attribute values of the plurality of first entities of the first type and the plurality of first entities of the second type for the corresponding second entity, wherein N is the number of principal components in each set of principal components, and an edge exists in the plurality of edges between a first node and a second node in the plurality of nodes when the first node is among the k nearest neighboring nodes of the second node in the first plurality of node, wherein the k nearest neighboring nodes to the second node is determined by computing a distance in the N-dimensional space between each node in the plurality of nodes, other than the second node, and the second node.

18. The visualization system of claim 17, wherein the distance is a Euclidean distance.

19. The visualization system of claim 1, wherein each first entity of the first type in a particular second entity in the plurality of second entities is barcoded with a first barcode that is unique to the particular second entity, wherein each first entity of the second type in the particular second entity is barcoded with a second barcode that is unique to the particular second entity, and wherein the second barcode is different from the first barcode.

20. The visualization system of claim 1, wherein a discrete attribute value of each first entity of the first type and a discrete attribute value of each first entity of the second type in a particular second entity in the plurality of second entities is determined after the particular second entity has been separated from all the other second entities in the plurality of second entities into its own microfluidic partition.

21. A method for visualizing patterns in a discrete attribute value dataset, the method comprising:

at a computer system comprising a persistent memory and a non-persistent memory:

storing the discrete attribute value dataset in the persistent memory, wherein the discrete attribute value dataset comprises, for each respective second entity in a plurality of second entities, (i) a corresponding first discrete attribute value for each first entity of a first type in a plurality of first entities of the first type and Iii) a corresponding second attribute value for each first entity of a second type in a plurality of first entities of a second type, and the discrete attribute value dataset redundantly represents the corresponding first discrete attribute value for each first entity of the first type and the corresponding second discrete attribute value for each first entity of the second type for each respective second entity in the plurality of second entities in both a compressed sparse row format and a compressed sparse column format;

clustering the discrete attribute value dataset using the first discrete attribute value for at least one first entity of the first type or the second discrete attribute value for at least one first entity of the second type, or data reduction components derived therefrom, for each respective second entity in the plurality of second entities thereby assigning each respective second entity in the plurality of second entities to a corresponding cluster in a plurality of clusters, wherein the clustering is configured to load less than the entirety of the discrete attribute value dataset into the non-persistent memory during the clustering thereby allowing the clustering of the discrete attribute value dataset having a size that exceeds storage space in the non-persistent memory allocated to the discrete attribute value dataset; and in response to receiving input, presenting first information related to at least one second attribute value for a first entity of the second type in the plurality of first entities of the second type for a respective second entity in the plurality of second entities, displaying in a first panel of a user interface the first information, wherein the first information is presented in association with second information that is related to a corresponding cluster to which the respective second entity in the plurality of second entities is assigned.

22. A non-transitory computer-readable medium storing one or more computer programs executable by a computer for visualizing patterns in a discrete attribute value dataset, the computer comprising a persistent memory and a non-persistent memory, the one or more computer programs collectively encoding computer executable instructions for performing a method comprising:

storing the discrete attribute value dataset in the persistent memory, wherein the discrete attribute value dataset comprises, for each respective second entity in a plurality of second entities, (i) a corresponding first discrete attribute value for each first entity of a first type in a plurality of first entities of the first type and (ii) a corresponding second attribute value for each first entity of a second type in a plurality of first entities of a second type, and the discrete attribute value dataset redundantly represents the corresponding first discrete attribute value for each first entity of the first type and the corresponding second discrete attribute value for each first entity of the second type for each respective second entity in the plurality of second entities in both a compressed sparse row format and a compressed sparse column format;

clustering the discrete attribute value dataset using the first discrete attribute value for at least one first entity of the first type or the second discrete attribute value for at least one first entity of the second type, or data reduction components derived therefrom, for each respective second entity in the plurality of second entities thereby assigning each respective second entity in the plurality of second entities to a corresponding cluster in a plurality of clusters, wherein the clustering is configured to load less than the entirety of the discrete attribute value dataset into the non-persistent memory during the clustering thereby allowing the clustering of the discrete attribute value dataset having a size that exceeds storage space in the non-persistent memory allocated to the discrete attribute value dataset; and in response to receiving input, presenting first information related to at least one second attribute value for a first entity of the second type in the plurality of first entities of the second type for a respective second entity in the plurality of second entities, displaying in a first panel of a user interface the first information, wherein the first information is presented in association with second information that is related to a corresponding cluster to which the respective second entity in the plurality of second entities is assigned.

* * * * *